(12) United States Patent
Puri et al.

(10) Patent No.: US 12,178,907 B2
(45) Date of Patent: Dec. 31, 2024

(54) BINARY LIPID BILAYER-CONTAINING VESICLES COMPRISING EMBEDDED CYTOTOXIC AGENTS AND METHODS OF MAKING AND USING THE SAME

(71) Applicant: The USA, as represented by the Secretary, Department of Health and Human Services, Bethesda, MD (US)

(72) Inventors: Anu Puri, Frederick, MD (US); Mathias Viard, Frederick, MD (US)

(73) Assignee: The United States of America, as Represented by the Secretary, Department of Health and Human Services, Bethesda, MD (US)

(*) Notice: Subject to any disclaimer, the term of this patent is extended or adjusted under 35 U.S.C. 154(b) by 941 days.

(21) Appl. No.: 17/259,499

(22) PCT Filed: Jul. 11, 2019

(86) PCT No.: PCT/US2019/041464
§ 371 (c)(1),
(2) Date: Jan. 11, 2021

(87) PCT Pub. No.: WO2020/014522
PCT Pub. Date: Jan. 16, 2020

(65) Prior Publication Data
US 2021/0236424 A1 Aug. 5, 2021

Related U.S. Application Data

(60) Provisional application No. 62/697,287, filed on Jul. 12, 2018.

(51) Int. Cl.
| *A61K 9/127* | (2006.01) |
| *A61K 41/00* | (2020.01) |
| *A61K 47/54* | (2017.01) |
| *A61K 47/60* | (2017.01) |

(52) U.S. Cl.
CPC ........ *A61K 9/1271* (2013.01); *A61K 41/0071* (2013.01); *A61K 47/543* (2017.08); *A61K 47/60* (2017.08)

(58) Field of Classification Search
CPC .............. A61K 9/1271; A61K 41/0071; A61K 47/543; A61K 47/60; A61K 31/4745; A61P 35/00
See application file for complete search history.

(56) References Cited

U.S. PATENT DOCUMENTS

| 5,006,343 | A | * | 4/1991 | Benson ................ A61K 9/0073 514/1.2 |
| 7,169,753 | B2 | | 1/2007 | Scheer et al. |
| 7,354,599 | B2 | | 4/2008 | Albrecht et al. |
| 2010/0056983 | A1 | | 3/2010 | Dougherty et al. |
| 2016/0136289 | A1 | | 5/2016 | Puri et al. |

FOREIGN PATENT DOCUMENTS

| WO | WO 2012/006009 A1 | 1/2012 |
| WO | WO 2013/082702 A1 | 6/2013 |
| WO | WO 2015/006429 | 1/2015 |

OTHER PUBLICATIONS

Yavlovich, A et al J Therm Anal Calorim, vol. 98, pp. 97-104, (2009).*
Chechetka et al., "Light-driven liquid metal nanotransformers for biomedical theranostics," *Nature Communications*, vol. 8, pp. 1-19, May 31, 2017.
Cintenza et al., "Diacyllipid Micelle-Based Nanocarrier for Magnetically Guided Delivery of Drugs in Photodynamic Therapy," *Molecular Pharmaceutics*, vol. 3(4):415-423, 2006 (Abstract only).
Colantonio et al., "Quantitative Analysis of Phospholipids Using Nanostructured Laser Desorption Ionization Targets," *Lipids*, 46(5): 469-477, Feb. 15, 2011.
Gupta et al., "Multifunctional Nanoplatforms for Fluorescence Imaging and Photodynamic Therapy Developed by Post-loading Photosensitizer and Fluorophore to Polyacrylamide Nanoparticles," *Nanomedicine*, 8(6): 941-950, Aug. 2012.
Haynes et al., "Maximizing the Supported Bilayer Phenomenon: Liposomes Comprised Exclusively of PEGylated Phospholipids for Enhanced Systemic and Lymphatic Delivery," *ACS Applied Materials & Interfaces*, vol. 8, pp. 24361-24367, Aug. 31, 2016.
Heidarli et al., "State of the Art of Stimuli-Responsive Liposomes for Cancer Therapy," *Iranian Journal of Pharmaceutical Research*, 16(4): 1273-1304, Dec. 31, 2016.
International Search Report and Written Opinion issued for International Application No. PCT/US2014/045922 on Oct. 20, 2014.
International Search Report and Written Opinion issued for International Application No. PCT/US2019/041464 on Sep. 27, 2019.
Lamparski et al., "Photoinduced destabilization of liposomes," *Biochemistry*, vol. 31, pp. 685-694, Jan. 28, 1992.
Li et al., "A review on phospholipids and their main applications in drug delivery systems," *Asian Journal of Pharmaceutical Sciences*, vol. 10, pp. 91-98, Sep. 28, 2014.
Liu et al., "Influence of Polyethylene Glycol Density and Surface Lipid on Pharmacokinetics and Biodistribution of Lipid-Calcium-Phosphate Nanoparticles," *Biomaterials*, 35(9): 3027-3034, Mar. 2014.
Luo et al., "Doxorubicin Encapsulated in Stealth Liposomes Conferred with Light-Triggered Drug Release," *Biomaterials*, vol. 75, pp. 193-202, Oct. 23, 2015.

(Continued)

*Primary Examiner* — Lezah Roberts
*Assistant Examiner* — Abdulrahman Abbas
(74) *Attorney, Agent, or Firm* — Klarquist Sparkman, LLP

(57) ABSTRACT

Embodiments of vesicles comprising embedded cytotoxic agents are disclosed, as well as methods of making and using the vesicles. Pharmaceutical compositions including the vesicles also are disclosed. The vesicles include a binary lipid bilayer surrounding a cavity, wherein the vesicle binary lipid bilayer includes (i) a non-bilayer forming lipid (or combination of non-bilayer forming lipids) and a PEGylated lipid; and (i) a cytotoxic agent embedded within the vesicle wall.

27 Claims, 25 Drawing Sheets

(56) References Cited

OTHER PUBLICATIONS

Mermut et al., "Effect of liposomal confinement on photothermal and photo-oximetric fluorescence lifetimes of photosensitizers with varying hydrophilicity," *Journal of Biomedical Optics*, 13(4): 041314-1-11, Jul. 1, 2008.

Noiseux et al., "Effect of liposomal confinement on photochemical properties of photosensitizers with varying hydrophilicity," *Journal of Biomedical Optics*, 13(4): 041313-1-11, Jul. 1, 2008.

Puri, "Phototriggerable Liposomes: Current Research and Future Perspectives," *Pharmaceutics*, vol. 6, pp. 1-25, Dec. 19, 2013.

Roy et al., "Ceramic-Based Nanoparticles Entrapping Water-Insoluble Photosensitizing Anticancer Drugs: A Novel Drug-Carrier System for Photodynamic Therapy," *J. Am. Chem. Soc.*, vol. 125, pp. 7860-7865, Jun. 10, 2003.

Sine et al., "Photo activation of HPPH encapsulated in 'Pocket' liposomes triggers multiple drug release and tumor cell killing in mouse breast cancer xenografts," *International Journal of Nanomedicine*, vol. 10, pp. 125-145, Dec. 19, 2014.

Viard et al., "Design and biological activity of novel stealth polymeric lipid nanoparticles for enhanced delivery of hydrophobic photodynamic therapy drugs," *Nanomedicine: Nanotechnology, Biology, and Medicine*, vol. 14, pp. 2295-2305, Oct. 2018.

Wang et al., "Novel Methods to Incorporate Photosensitizers Into Nanocarriers for Cancer Treatment by Photodynamic Therapy," *Lasers in Surgery and Medicine*, vol. 43, pp. 686-695, Aug. 15, 2011.

Yavlovich et al., "A novel class of photo-triggerable liposomes containing DPPC:$DC_{8,9}PC$ as vehicles for delivery of doxorubicin to cells," *Biochimica et Biophysica Acta*, 1808(1): 117-126, Jan. 2011.

Yavlovich et al., "Design of liposomes containing photopolymerizable phospholipids for triggered release of contents," *J. Therm. Anal. Calorim.*, vol. 98, pp. 97-104, Jul. 25, 2009.

Yavlovich et al., "Light-sensitive Lipid-based Nanoparticles for Drug Delivery: Design Principles and Future Considerations for Biological Applications," *Mol. Membr. Biol.*, 27(7): 364-381, Oct. 2010.

Yavlovich et al., "Low-visibility light-intensity laser-triggered release of entrapped calcein from 1,2-bis (tricosa-10,12-diyonyl)-sn-glycero-3-phosphocholine liposomes is mediated through a type I photoactivation pathway," *International Journal of Nanomedicine*, vol. 8, pp. 2575-2587, Jul. 21, 2013.

\* cited by examiner

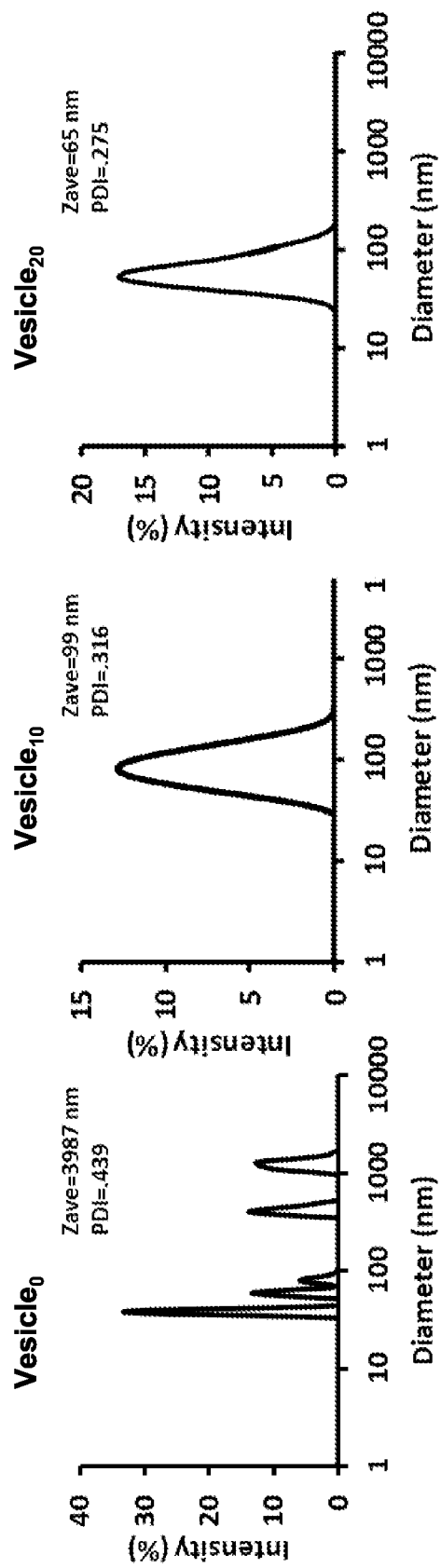
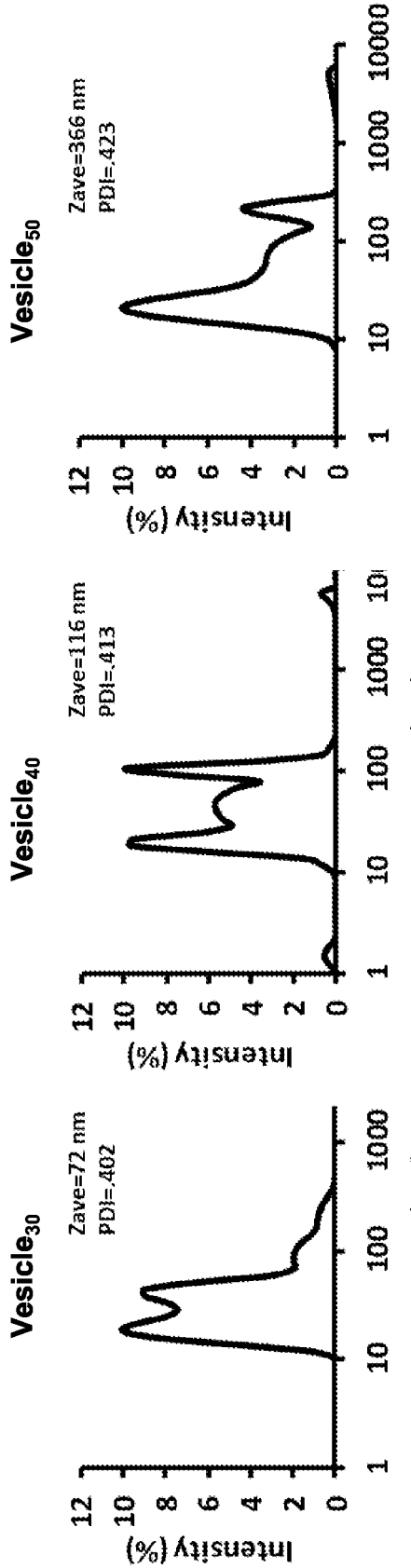

Vesicle$_{20}$

Vesicle$_{20}$ - HPPH

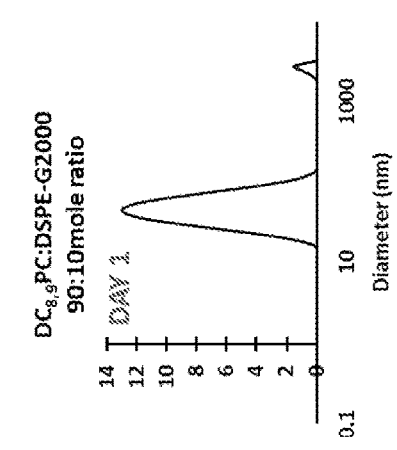
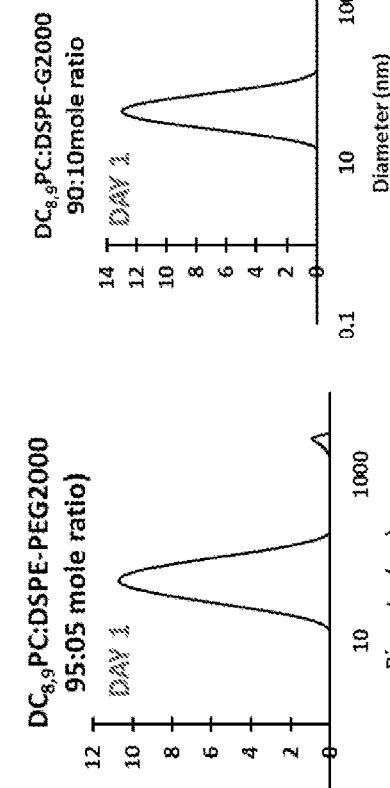
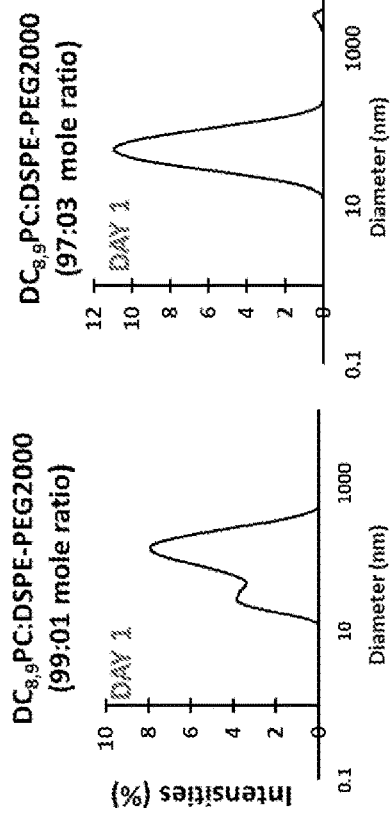
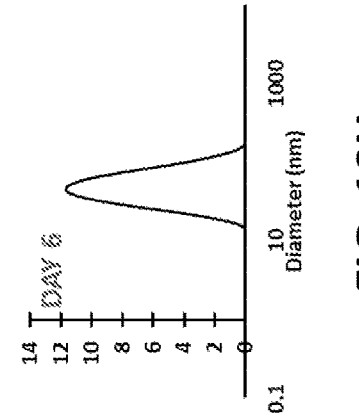
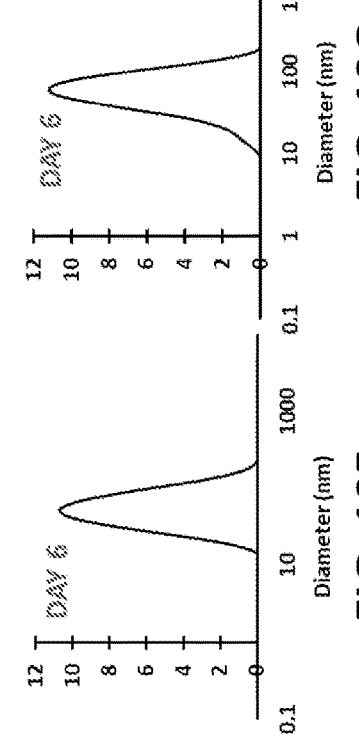
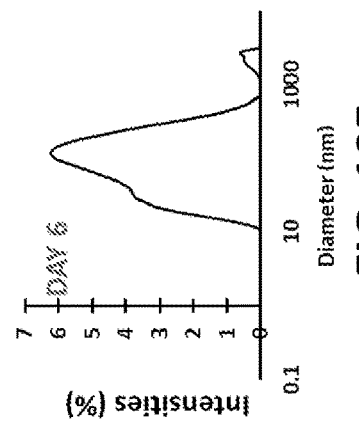

Animal 1

Animal 2

BINARY LIPID BILAYER-CONTAINING VESICLES COMPRISING EMBEDDED CYTOTOXIC AGENTS AND METHODS OF MAKING AND USING THE SAME

CROSS REFERENCE TO RELATED APPLICATION

This is the U.S. National Stage of International Application No. PCT/US2019/041464, filed Jul. 11, 2019, which was published in English under PCT Article 21(2), which application in turn claims the benefit of and priority to the earlier filing date of U.S. Provisional Patent Application No. 62/697,287, filed on Jul. 12, 2018, the entirety of which is incorporated herein by reference.

ACKNOWLEDGMENT OF GOVERNMENT SUPPORT

The invention was made with government support under project number ZIA BC 011061, awarded by the National Institutes of Health, National Cancer Institute. The government has certain rights in the invention.

FIELD

Disclosed herein are embodiments of vesicles that comprise a binary lipid bilayer and a cytotoxic agent embedded within the binary lipid bilayer, and methods of making and using the same.

PARTIES TO JOINT RESEARCH AGREEMENT

The National Cancer Institute, National Institutes of Health and Roswell Park Comprehensive Cancer Center are parties to a joint research agreement related to the technology disclosed herein.

BACKGROUND

Targeted delivery of anti-cancer agents to tumor tissue, with minimum damage to normal cells and tissue, is an important goal in cancer therapy. Cancer nanotechnology platforms, such as photodynamic therapy (PDT) drug delivery platforms, have shown promise; however, conventional PDT platforms have structural features that limit their use in therapeutic settings and also limit their ability to effectively accumulate in tumors. A need in the art exists for PDT platforms that exhibit preferential tumor uptake, plasma stability, and longer shelf lives.

SUMMARY

Disclosed herein are embodiments of a vesicle, comprising a binary lipid bilayer comprising an alkyne-containing phospholipid and a PEGylated lipid; and a cytotoxic agent embedded in the binary lipid bilayer. In particular disclosed embodiments, the binary lipid bilayer is free of, or does not comprise, a lipid other than the alkyne-containing phospholipid or the PEGylated lipid. In some embodiments, the alkyne-containing phospholipid is an alkyne-containing phosphocholine lipid, an alkyne-containing phosphoethanolamine lipid, or a mixture of the alkyne-containing phosphocholine lipid and the alkyne-containing phosphoethanolamine lipid. Exemplary embodiments of the disclosed vesicle comprise a binary lipid bilayer comprising $DC_{8,9}PC$ and DSPE-PEG2000 and HPPH embedded in the binary lipid bilayer; wherein the binary lipid bilayer is free of, or does not comprise, a lipid other than the DSPE-PEG2000 and the $DC_{8,9}PC$ (alone or in combination with $DC_{8,9}PE$). Other exemplary embodiments are described herein.

Also disclosed herein are embodiments of a method, comprising providing a vesicle according to the present disclosure and irradiating the vesicle with targeted application of light having a selected wavelength in the near-infrared range and a selected intensity for an effective period of time to activate at least a portion of the cytotoxic agent. In some embodiments, the method can further comprise identifying a subject as having a condition that may be treated with the cytotoxic agent; and administering the vesicle to the subject; wherein the targeted application of light is directed at a targeted portion of the subject.

Also disclosed are embodiments of a method for impairing growth of a tumor in a subject, comprising: administering to the subject a therapeutically effective amount of a vesicle according to the present disclosure; and irradiating the vesicle by targeted application of light having a selected wavelength in the near-infrared range and a selected intensity to a target area of the subject proximate a location of the tumor for an effective period of time to activate at least a portion of the cytotoxic agent to promote reactive oxygen species formation, thereby impairing growth of the tumor.

The foregoing and other objects and features of the present disclosure will become more apparent from the following detailed description, which proceeds with reference to the accompanying figures.

BRIEF DESCRIPTION OF THE DRAWINGS

FIG. 7A shows results of the amount of vesicle-associated HPPH for the lipid:HPPH ratios that were examined and FIG. 7B shows the percent of HPPH encapsulated vesicles for the different lipid:HPPH ratios examined.

FIGS. 10A-10F are graphs of intensity (%) as a function of diameter (nm), showing the average diameter and polydispersity index of vesicle embodiments disclosed herein having different concentrations of a PEGylated lipid in the binary lipid bilayer; vesicles containing various DSPE-PEG2000 amounts with $DC_{8,9}PC$ were prepared by probe sonication, diluted in HBS at either 1:20 or 1:40 ratios (v/v), and dynamic light scattering measurements were obtained.

FIG. 11A) and a vesicle that does comprise an embedded cytotoxic agent (Vesicle$_{20}$-HPPH; FIG. 11B).

FIG. 16A shows total radiation efficiency of DiR in tumors (±S.D. 4 animals) and FIG. 16B shows relative ratios of DiR in tumors versus liver for each group; tumor to liver ratios obtained for the vesicles containing 4 mol % of the PEG-lipid were taken as 100 and values are expressed as an average from four animals (±S.D.).

FIGS. 19A-19H are graphs of intensity (%) as a function of diameter (nm), showing the average diameter and polydispersity index of certain formulations comprising DSPE-PEG2000 and $DC_{8,9}PC$.

FIGS. 24A and 24B are graphs of intensity (%) as a function of diameter (nm), showing the average diameter and polydispersity index of certain formulations comprising DSPE-PEG2000 and $DC_{8,9}PC$ and Ce6 after 1 day (FIG. 24A) and after 7 days (FIG. 24B) and FIG. 24C shows Ce6 can be incorporated into the vesicles.

FIGS. 26A and 26B show results of DSPE-PEG5000 and $DC_{8,9}PC$ at a ratio of 90:10 $DC_{8,9}PC$:DSPE-PEG5000 after 1 day (FIG. 26A) and after 4 months (FIG. 26B) and FIGS. 26C and 26D show results of DSPE-PEG5000 and $DC_{8,9}PC$ at a ratio of 99:1 $DC_{8,9}PC$:DSPE-PEG5000 after 1 day (FIG. 26C) and after 4 months (FIG. 26D).

FIGS. 27A and 27B are graphs of intensity (%) as a function of diameter (nm), showing the average diameter and polydispersity index of certain formulations comprising DSPE-PEG2000, $DC_{8,9}PC$, and $DC_{8,9}PE$ and further including HPPH at different lipid:HPPH ratios; FIG. 27A shows results for embodiments comprising a (total) lipid-to-HPPH ratio of 20:1 and FIG. 27B shows results for embodiments comprising a (total) lipid-to-HPPH ratio of 100:1.

DETAILED DESCRIPTION

I. Overview of Terms and Abbreviations

Figure 1:
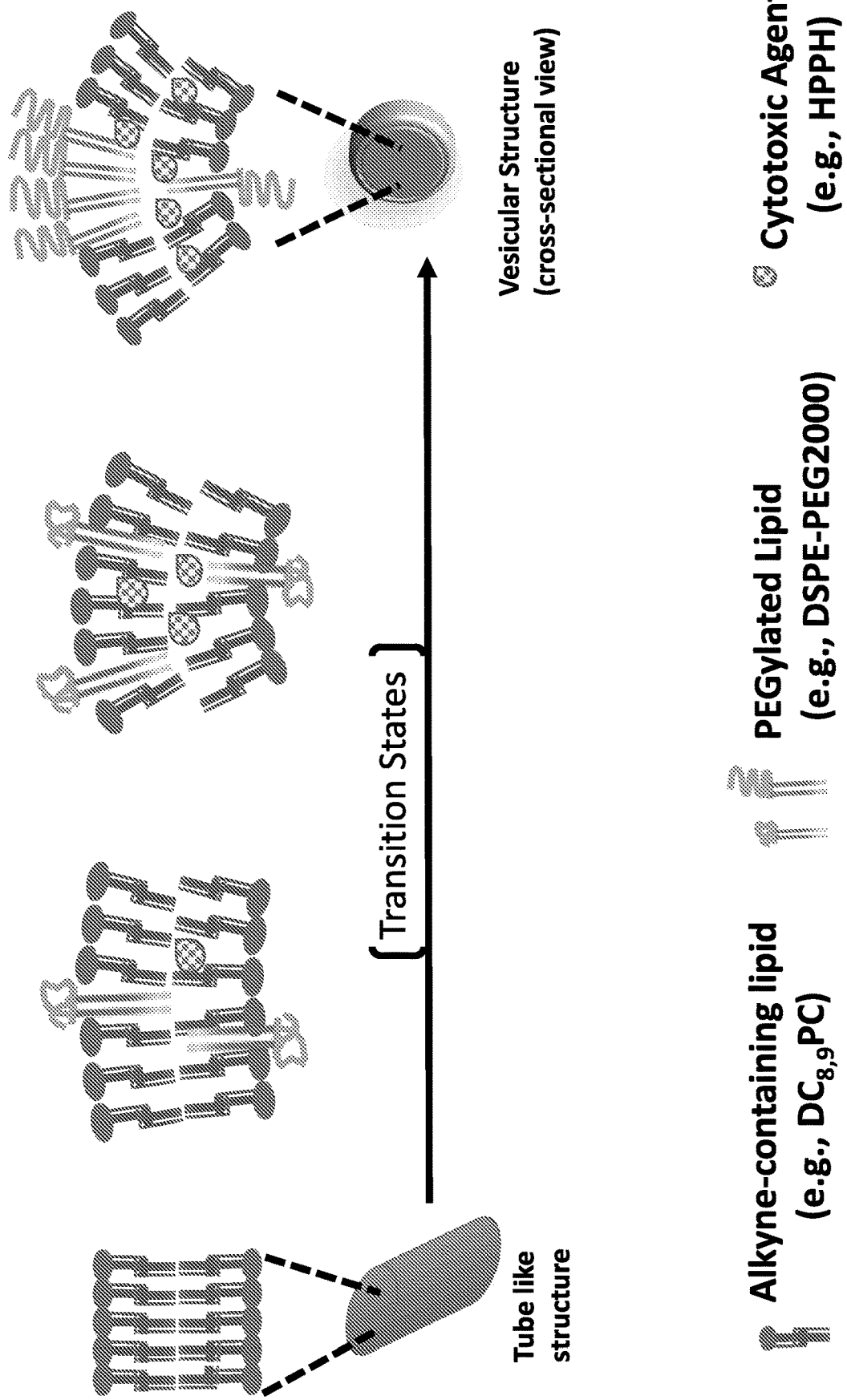
FIG. 1 is a schematic illustration of a proposed model for how a binary lipid bilayer can be formed between a PEGylated lipid and a non-bilayer-forming alkyne-containing phosphocholine lipid.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

All chemical compounds include either or both of the (+) and (−) stereoisomers, as well as any geometric isomers, such as Z and E isomers and cis and trans isomers. Other chemistry terms herein are used according to conventional usage in the art, as exemplified by *Hawley's Condensed Chemical Dictionary*, Richard J. Lewis, Sr. (ed.), published by John Wiley & Sons, Inc., 1997 (ISBN 0-471-29205-2).

A. Explanation of Terms

The following explanations of terms are provided to better delineate the subject matter of the present disclosure and to guide those of ordinary skill in the art in its practice.

Administering: Administration by any route, for example oral, topical, intravenous, intraperitoneal, intramuscular, intralesional, intranasal, or subcutaneous administration, release from a suppository, or the implantation of a slow-release device (e.g., a mini-osmotic pump) to the subject. "Parenteral" administration is by any route other than through the alimentary tract and includes intravascular administration directly into a blood vessel, for example by intravenous or intra-arterial administration.

Alkyne-Containing Phosphocholine Lipid: A lipid comprising a phosphocholine group (i.e., $(CH_3)_3N^+(CH_2)_2$—$OPO_3^-$—) and at least one alkyne moiety within a carbon chain of the lipid, with some embodiments comprising more than one alkyne moiety, which can be in the same carbon chain or different carbon chains of the lipid. In some embodiments, the alkyne-containing phosphocholine lipid can comprise at least one diyne moiety. An exemplary alkyne-containing phosphocholine lipid is $DC_{8,9}PC$.

Alkyne-Containing Phosphoethanolamine Lipid: A lipid comprising a phosphoethanolamine group (i.e., $H_3N^+(CH_2)_2$—$OPO_3^-$—) and at least one alkyne moiety within a carbon chain of the lipid, with some embodiments comprising more than one alkyne moiety, which can be in the same carbon chain or different carbon chains of the lipid. In some embodiments, the alkyne-containing phosphoethanolamine lipid can comprise at least one diyne moiety. An exemplary alkyne-containing phosphocholine lipid is $DC_{8,9}PE$.

Alkyne-Containing Phospholipid: A lipid comprising a phosphate group (e.g., a phosphocholine or phosphoethanolamine) and at least one alkyne moiety within a carbon chain of the lipid, with some embodiments comprising more than one alkyne moiety, which can be in the same carbon chain or different carbon chains of the lipid. In some embodiments, the alkyne-containing phospholipid can comprise at least one diyne moiety. Exemplary alkyne-containing phospholipids include alkyne-containing phosphocholine lipids and alkyne-containing phosphoethanolamine lipids.

Bilayer: A component of a vesicle that defines a core of the vesicle and that comprises at least two lipid layers, wherein each layer comprises at least one non-bilayer-forming lipid (e.g., an alkyne-containing phospholipid (or a combination of alkyne-containing phospholipids)) and a PEGylated lipid.

Carrier: An excipient that serves as a component capable of delivering a compound described herein. In some embodiments, a carrier can be a suspension aid, solubilizing aid, or aerosolization aid. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical formulations to be administered can contain minor amounts of non-toxic auxiliary substances, such as wetting or emulsifying agents, preservatives, and pH buffering agents and the like, for example sodium acetate or sorbitan monolaurate.

Lipid: A term for fats and fat-derived materials. In some embodiments, lipids include esters of fatty acids (simple lipids, such as fats, sterols, waxes, and triglycerides) or closely related substances (compound lipids, such as phospholipids). Lipids generally are insoluble in water but soluble in organic solvents.

Near-Infrared (NIR): A region of the electromagnetic spectrum between the visible region and the infrared region. There is no set definition for the boundaries of the near-infrared region, but definitions include the wavelength ranges from 650-2500 nm, 750-2500 nm, 780-2500 nm, 800-2500 nm, 700-1400 nm, or 780-3000 nm. As used herein, NIR refers to the wavelength region of 650-2500 nm.

Non-Bilayer-Forming Lipid: A lipid that is not, without structural modification or combination with a PEGylated lipid, capable of aggregating and forming a bilayer on its own. Examples of non-bilayer-forming lipids include alkyne-containing phospholipids, such as alkyne-containing phosphocholine lipids (e.g., $DC_{8,9}PC$), alkyne-containing phosphoethanolamine lipids (e.g., $DC_{8,9}PE$), and combinations thereof.

Nucleic Acid Molecule: Includes DNA and RNA. The DNA may be operably linked to a promoter and/or contained with an expression vector, such as a plasmid. The DNA may be genomic (with introns) or consist only of the intron-less cDNA coding sequence. In some examples, the DNA sequence may encode a therapeutic protein, such as an anti-tumor protein. In other examples, the RNA sequence may be an inhibitory RNA (iRNA) that inhibits gene expression. Examples include microRNA (miRNA) and small interfering RNA (siRNA).

PEGylation: With respect to vesicles, PEGylation refers to incorporating surface-bound polyethylene glycol (PEG) to protect vesicles from detection by the reticuloendothelial system and to increase blood circulation time of the vesicle. Polyethylene glycols (PEG) are hydrophilic polymers composed of repeating ethylene oxide subunits with two terminal hydroxyl groups that can be chemically activated. The general structure of PEG is: $HO-(CH_2CH_2O)_n-CH_2CH_2-OH$, wherein n can be 0 or higher, such as 0 to 10,000 (or higher), or 1 to 7,500, or 1 to 5,000, or 1 to 3,000, or 1 to 2,000, or 1 to 1,000. In some embodiments, n is 350 to 10,000, such as 350 to 5,000, or 350 to 2,000, or 350 to 1,000. PEG chains can be linear or branched. PEG conjugation to a pharmaceutically or biologically useful agent typically involves activating the PEG by preparing a PEG derivative having functional groups. The functional group on PEG is chosen based on the reactive group of the molecule to be conjugated. The molecular weight of the PEGs is chosen to avoid rapid clearance by the liver as well as any toxic effects.

PEGylated Lipid: A lipid comprising a polyethylene glycol (PEG) group covalently bound to the lipid, wherein the PEG group is bound directly to a functional group of the lipid or indirectly to the lipid via a linker or other functional group.

Pharmaceutical or Bioactive Agent: A molecule that is capable of providing a therapeutic (including diagnostic) effect. A bioactive agent has an effect on living tissue. Examples include anti-cancer agents, imaging agents, anti-inflammatory agents, and small interfering RNA (siRNA) molecules.

Pharmaceutically Acceptable: The term "pharmaceutically acceptable" refers to substance that can be taken into a subject without significant adverse toxicological effects on the subject.

Pharmaceutically Acceptable Excipient: A substance, other than an active compound (e.g., a compound described herein), that is included in a formulation of the active compound. As used herein, an excipient may be incorporated within particles of a pharmaceutical formulation, or it may be physically mixed with particles of a pharmaceutical formulation. An excipient also can be in the form of a solution, suspension, emulsion, or the like. An excipient can be used, for example, to dilute an active agent and/or to modify properties of a pharmaceutical formulation. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethylene glycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

Phospholipid: A lipid that includes a phosphate group. The phospholipid comprises a glycerol bound to the phosphate group and two fatty acid chains.

Photoactivatable/Photo-triggerable: Capable of being activated (e.g., converted from an inert form to an active form) by light energy.

Photoactivation/Photo-triggering: Activating a vesicle using light energy. As used herein, activating can comprise promoting reactive oxygen species formation from a cytotoxic agent disclosed herein and/or destabilizing a vesicle's binary lipid bilayer wall so that at least a portion of a cytotoxic agent embedded within the vesicle's binary lipid bilayer is released. In some embodiments, photoactivation occurs upon exposure of the vesicle to, for example, targeted application of light of a selected wavelength, intensity, and/or surface area, to a pre-selected target area.

Photosensitizer: A molecular or atomic species that initiates a photochemical reaction. The term "photosensitizer" also refers to a substance that sensitizes an organism, cell, or tissue to light. Photosensitizers may be used, for example, in photodynamic therapy for treatment of cancer. The photosensitizer absorbs light of a particular wavelength or wavelength range and becomes excited. The excited photosensitizer transfers energy to nearby molecules. In photodynamic therapy, the photosensitizer may be taken up by a cancer cell. Upon light absorption, the photosensitizer transfers energy to oxygen present within the cell, thereby producing reactive oxygen species (ROS) which are toxic to cancer cells.

Subject: A mammal and/or other animal, such as humans, companion animals (e.g., dogs, cats, rabbits, etc., utility animals, feed animals and the like; thus, disclosed methods are applicable to both human therapy and veterinary applications.

Therapeutically Effective Amount: A quantity or concentration of a specified compound or composition sufficient to achieve a desired effect in a subject being treated. For example, this may be the amount of a vesicle as disclosed herein, or pharmaceutical composition comprising the vesicle, necessary to cause tumor cell death or inhibition, thereby eliminating a tumor, reducing the size of a tumor, and/or inhibiting tumor growth in a subject. Ideally, a therapeutically effective amount of a compound or composition is an amount sufficient to reduce the desired effect without substantial cytotoxic effect on non-tumor cells. However, the therapeutically effective amount of the vesicle or composition will be dependent on the subject being treated, the size and characteristics of the tumor, and the manner of administration of the therapeutic composition.

Treating/Treatment: Treatment of a disease or condition of interest in a subject, particularly a human or mammal having the disease or condition of interest or that may or may not be prone to developing the disease or condition, and includes by way of example, and without limitation:
  (i) prophylactic administration to prevent the disease or condition from occurring in a subject, or to ameliorate symptoms associated with the condition if required in particular, when such subject is predisposed to the condition but has not yet been diagnosed as having it;
  (ii) inhibiting the disease or condition, for example, arresting or slowing its development;
  (iii) relieving the disease or condition, for example, causing regression of the disease or condition or a symptom thereof; or
  (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

Vesicle: A structural component comprising a lipid bilayer that forms and encloses a cavity, wherein the cavity does not comprise a core material such as core materials found in nanoparticles (e.g., CaP cores, liquid metal cores, and the like). Instead, the cavity within the vesicle is a closed internal space. Vesicles may be characterized by membrane type. Unilamellar vesicles have a single membrane. Oligolamellar vesicles and multilamellar vesicles have multiple, usually concentric, membrane layers and are typically larger than 0.1 μm. Vesicles with several nonconcentric membranes, i.e., several small vesicles contained within a larger vesicle, are termed multivesicular vesicles. In particular disclosed embodiments, the vesicles embodiments of the present disclosure are "unilamellar," and thus have a single binary lipid bilayer membrane.

Z-average Size: An average size determined by analyzing dynamic light scattering data using the technique of cumulants; also referred to as the 'cumulants mean' or the 'harmonic intensity averaged particle diameter' (ISO 22412).

B. Abbreviations $DC_{8,9}PC$: 1,2 bis(tricosa-10,12-diynoyl)-sn-glycero-3-phosphocholine
$DC_{8,9}PE$: 1,2-bis(10,12-tricosadiynoyl)-sn-glycero-3-phosphoethanolamine
DiR: 1,1'-dioctadecyl-3,3,3',3'-tetramethylindotricarbocyanine iodide
DMEM: Dulbecco's Modified Eagle Medium (supplemented with 10% (v/v) heat-inactivated FBS (fetal bovine serum), 100 i.u./ml penicillin and 100 μg/mL streptomycin)
DPPC: 1,2-dipalmitoyl-sn-glycero-3-phosphocholine
DSPE-PEG2000 (18:0 PEG2 PE): 1,2-Distearoyl-sn-Glycero-3 Phosphoethanolamine-N-[Methoxy(Polyethylene glycol)-2000] (Ammonium Salt)
HBS: HEPES buffer, 10 mM HEPES, 140 mM NaCl (pH 7.2-7.5)
HPPH: 2-[1-hexyloxyethyl]-2-devinyl pyropheophorbide-a
PBS: Phosphate buffered saline (2.66 mM KCl, 1.47 mM $KH_2PO_4$, 138 mM NaCl, 8.06 mM $Na_2HPO_4$-$7H_2O$ (pH 7.1))
PDT: photodynamic therapy
PI: polydispersity index II. Introduction Clinical utility of anti-cancer drugs is often limited due their poor solubility, reduced bioavailability, and non-specific toxicity. These limitations can be alleviated by developing suitable carriers for transport of these drugs to desired site(s). Some previously investigated platforms in cancer nanomedicine include lipid-based nanocarriers; however, conventional liposomes are limited in their ability to specifically accumulate in tumors and avoid being taken up by the mononuclear phagocytic system (MPS).

By introducing PEGylated lipids into a liposome, it is possible to create "stealth" liposomes that can partially reduce MPS uptake; however, large fractions of such liposomes are still taken up by the MPS. Furthermore, the degree and extent of PEGylated lipid incorporation into liposomes is often limited due to their structural constraints. Typically, PEG lipid concentrations that can be efficiently incorporated into liposomes are limited by such structural constraints and such liposomes typically require using bilayer-forming lipids, such as 1,2-dioleoyl-sn-glycero-3-phosphocholine (or dioleoyl phosphatidylcholine, "DOPC").

The present disclosure describes embodiments of a novel vesicle that comprises a binary lipid bilayer comprising an alkyne-containing phospholipid and a PEGylated lipid and that further comprises a cytotoxic agent embedded in the lipid layer. In some embodiments, the alkyne-containing phospholipid is an alkyne-containing phosphocholine lipid, an alkyne-containing phosphoethanolamine lipid, or a mixture of the alkyne-containing phosphocholine lipid and the alkyne-containing phosphoethanolamine lipid (such that both types of phospholipids are included in the binary lipid bilayer). The disclosed vesicle embodiments do not require using conventional phospholipids that typically are used in liposome delivery systems, such as phosphatidyl choline lipids, and instead only use two different lipids, reducing the complexity and cost associated with making the vesicles. The disclosed vesicle embodiments can accommodate impressively high amounts of the PEGylated lipid, while also enabling loading of a cytotoxic agent at high concentrations within the binary lipid membrane. The disclosed vesicle embodiments also maintain their stability upon storage at ambient temperatures and further accumulate in tumors at high efficiency, and exhibit remarkably high tumor care, with no recurrence.

III. Vesicle and Composition Embodiments

Disclosed herein are embodiments of a vesicle that comprises a binary lipid bilayer comprising an alkyne-containing phospholipid and a PEGylated lipid and a cytotoxic agent embedded in the lipid layer. In some embodiments, the alkyne-containing phospholipid is an alkyne-containing phosphocholine lipid, an alkyne-containing phosphoethanolamine lipid, or a mixture of the alkyne-containing phosphocholine lipid and the alkyne-containing phosphoethanolamine lipid. In particular embodiments, the alkyne-containing phospholipid is an alkyne-containing phosphocholine lipid or is a mixture of the alkyne-containing phosphocholine lipid and an alkyne-containing phosphoethanolamine lipid. In some embodiments, the binary lipid bilayer can comprise a plurality (e.g., two or more) of cytotoxic agents.

In particular disclosed embodiments, the vesicle can comprise (i) a binary lipid bilayer comprising an alkyne-containing phospholipid and a PEGylated lipid; and (ii) a cytotoxic agent embedded in the binary lipid bilayer, wherein the binary lipid bilayer is free of, or does not comprise, a lipid other than the alkyne-containing phospholipid or the PEGylated lipid. In an independent embodiments, an alkyne-containing phosphoethanolamine lipid is not what is referred to herein as "a lipid other than the alkyne-containing phospholipid or the PEGylated lipid."

In some embodiments, the vesicle can comprise (i) a binary lipid bilayer comprising an alkyne-containing phosphocholine lipid and the PEGylated lipid; and (ii) a cytotoxic agent embedded in the binary lipid bilayer, wherein the binary lipid bilayer is free of, or does not comprise, a lipid other than the alkyne-containing phosphocholine lipid or the PEGylated lipid. In yet additional embodiments, the vesicle can comprise (i) a binary lipid bilayer comprising an alkyne-containing phosphocholine lipid, an alkyne-containing phosphoethanolamine lipid, and the PEGylated lipid; and (ii) a cytotoxic agent embedded in the binary lipid bilayer, wherein the binary lipid bilayer is free of, or does not comprise, a lipid other than the alkyne-containing phosphocholine lipid, the alkyne-containing phosphoethanolamine lipid, or the PEGylated lipid. Lipids other than the alkyne-containing phosphocholine lipid, the alkyne-containing phosphoethanolamine lipid, or the PEGylated lipid can include phosphatidylcholine lipids (such as dipalmitoylphosphatidylcholine, or "DPPC"), non-PEGylated DSPE, cholesterol, a plasmalogen, DPPE-DVBA, bis-azo PC, bis-sorbyl phosphatidylcholine (or "bis-SorbPC"), and the like. In some embodiments, the vesicle can consist essentially of (i) a binary lipid bilayer made of the alkyne-containing phospholipid (e.g., an alkyne-containing phosphocholine lipid and/or an alkyne-containing phosphoethanolamine lipid) and the PEGylated lipid; and (ii) a cytotoxic agent embedded in the binary lipid bilayer. In such embodiments, the vesicle is free of a lipid other than the alkyne-containing phospholipid or the PEGylated lipid and any components that would deleteriously affect the ability of the vesicle to perform its desired function, such as agents or compounds that would disrupt the vesicle's shape and/or stability. In yet additional embodiments, the vesicle can consist of the alkyne-containing phospholipid (e.g., an alkyne-containing phosphocholine lipid and/or an alkyne-containing phosphoethanolamine lipid), the PEGylated lipid, and the cytotoxic agent. In yet additional embodiments, the vesicle can comprise (i) the binary lipid bilayer, which consists of the alkyne-containing phospholipid (e.g., an alkyne-containing phosphocholine lipid and/or an alkyne-containing phosphoethanolamine lipid) and the PEGylated lipid; and (ii) the cytotoxic agent. For certain imaging purposes, e.g., bio-distribution studies, trace amounts of a lipid probe (e.g., 1,1'-dioctadecyltetramethyl indotricarbocyanine iodide (DiR)) may be included in the vesicles. This component does not deleteriously affect the performance of the vesicle and it is not a necessary component of the vesicle embodiments In particular disclosed embodiments, the alkyne-containing phospholipid is a non-bilayer-forming lipid that does not, on its own, form a nanostructure in aqueous solution that is suitable for drug delivery. In some embodiments, the non-bilayer-forming lipid, alone, forms a tubule-like morphology. For example, see FIG. 1, which illustrates the tubule-like structure of an exemplary alkyne-containing phosphocholine lipid, $DC_{8,9}PC$. Other exemplary alkyne-containing phospholipids include, but are not limited to, alkyne-containing phosphoethanolamine lipids, such as $DC_{8,9}PE$ and the like.

The binary lipid bilayer can comprise from 80 mol % (or less, such as 75 mol %) to 97 mol %, such as 85 mol % to 95 mol %, or 85 mol % to 90 mol % of the alkyne-containing phospholipid (or a combination of such phospholipids). In particular disclosed embodiments, the alkyne-containing phospholipid (or combination of such phospholipids) is present at 80 mol %, 85 mol %, or 90 mol %. In embodiments comprising a mixture of an alkyne-containing phosphocholine lipid and an alkyne-containing phosphoethanolamine lipid as the alkyne-containing phospholipid, the alkyne-containing phosphocholine lipid can be present at 45 mol % to 85 mol %, such as 50 mol % to 80 mol %, or 50 mol % to 75 mol %, or 50 mol % to 70 mol %, or 50 mol % to 65 mol %; and the alkyne-containing phosphoethanolamine lipid can be present at 5 mol % to 45 mol %, such as 5 mol % to 40 mol %, or 5 mol % to 35 mol %, or 5 mol % to 30 mol %, or 5 mol % to 25 mol %, or 5 mol % to 20 mol %, or 5 mol % to 15 mol %, or 5 mol % to 10 mol %. In representative embodiments of such mixtures, the alkyne-containing phosphocholine lipid can be present at 65 mol % and the alkyne-containing phosphoethanolamine lipid can be present at 25 mol %. In yet additional embodiments, the alkyne-containing phosphocholine lipid can be present at 45 mol % and the alkyne-containing phosphoethanolamine lipid can be present at 45 mol %.

The non-bilayer-forming lipid is combined with a PEGylated lipid to form a vesicle structure, as illustrated schematically in FIG. 1. The PEGylated lipid can be selected from any PEGylated lipid that is suitable for therapeutic methods, including administration to a subject, and also that does not have too high of a hydrophilicity such that it will not accumulate in cells as desired. In particular disclosed embodiments, the PEGylated lipid comprises a phosphoethanolamine lipid modified with a PEG group. Such lipids can include, but are not limited to, 1,2-distearoyl-sn-glycero-3-phosphoethanolamine (DPSE) lipids comprising a PEG group having a molecular weight ranging from greater than 350 Da to 10,000 Da, such as 350 Da to 5,000 Da (or higher), or 500 Da to 5,000 Da. In some embodiments, the PEG group can have a molecular weight ranging from 1,000 Da to 5,000 Da, or 1,000 Da to 4,000 Da, or 1,000 Da to 3,000 Da, or 1,000 Da to 2,000 Da. In a representative embodiment, DPSE-PEG2000 is used as the PEGylated lipid. Other exemplary PEGylated lipids include, but are not limited to, cholesterol-PEG600, DPSE-PEG1000, DPSE-PEG5000, and the like.

The binary lipid bilayer can comprise 3 mol % to 20 mol % or higher (e.g., 25 mol %), and in particular embodiments can comprise greater than 6 mol % to 20 mol %, such as 8 mol % to 15 mol %, or 10 mol % to 15 mol % of the PEGylated lipid. In particular disclosed embodiments, the PEGylated lipid can be present in an amount of 10 mol %, 15 mol %, or 20 mol %. In an independent embodiment where the PEGylated lipid is DSPE-PEG2000, the PEGylated lipid is used in an amount greater than 6 mol %.

The disclosed alkyne-containing phospholipid and the PEGylated lipid interact to form a vesicle structure that defines an inner cavity (FIG. 1). Embodiments of the disclosed vesicles have a diameter ranging from 50 nm to 200 nm, such as from 60 nm to 150 nm, or 65 nm to 100 nm. In some embodiments, the disclosed vesicles can have a PI ranging from 0.2 to 0.3.

One or more cytotoxic agents can be embedded within the bilayer formed by the alkyne-containing phospholipid and the PEGylated lipid. In some embodiments, the cytotoxic agent is a hydrophobic compound, such as a tetrapyrrollic compound or a camptothecin. Exemplary tetrapyrrollic compounds include, but are not limited to, HPPH or tetrapyrrollic analogs thereof, such as amino diethyl analogs, aminohexane analogs, and other such analogs as disclosed by WO 2012/006009, the relevant portion of which is incorporated herein by reference; chlorin e6 (or "Ce6"); (3S,4S)-9-Ethenyl-14-ethyl-21-(methoxycarbonyl)-4,8,13,18-tetramethyl-20-oxo-3-phorbinepropanoic acid ("Pheophorbide a"); 3,3',3''',3'''-(2,3-dihydroporphyrin-5,10,15,20-tetrayl)tetraphenol (or "Temoporfin"), and 3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1 3,6.1 8,11.1 13,16.0 19,24]octacosa-1,3,5,7,9,11(27),12,14,16,18(25),19,21-dodecaen-9-yl]propanoic acid (or "Verteporfin"). HPPH is a lipophilic compound with a log P of 5.6 at physiological pH, a large molar extinction in the near-infrared region, i.e., $\varepsilon = 47,500$ $M^{-1}$ $cm^{-1}$ at 665 nm, and a singlet oxygen yield of 0.48. HPPH also has anti-cancer properties, and has been used in PDT, e.g., for treatment of esophageal cancer and non-small cell lung cancer. In some embodiments, activated HPPH exerts its therapeutic effect through generating reactive oxygen species (e.g., singlet oxygen) upon photoactivation. Chlorin e6 is another exemplary PDT compound that can be used in embodiments disclosed herein and, like HPPH, can be activated to exert a therapeutic effect. In some embodiments, the vesicle can comprise a camptothecin. Camptothecins are hydrophobic lactone drugs that exhibit chemotherapeutic activity. Exemplary camptothecins include, but are not limited to, camptothecin, silatecan 7-t-butyldimethylsilyl-10-hydroxycamptothecin (DB-67), 7-ethyl-10-hydroxy-20(S)-camptothecin (SN-38), topotecan, irinotecan, 9-nitro-camptothecin, lurtotecan, exatecan, gimatecan, and karenitecin. In additional embodiments, the cytotoxic agent can be selected from paclitaxel, daunorubicin, methotrexate, vincristine, etoposide, sorafenib, erlotinib, imatinib, or any combination thereof. Any combination and any number of cytotoxic agents can be used in the vesicles.

The cytotoxic agent (or combination of cytotoxic agents) can be embedded in the binary lipid bilayer at high concentrations, such as amounts ranging from 0.05 to 0.5 mg cytotoxic agent/mg lipid, such as 0.075 to 0.5 mg cytotoxic agent/mg lipid, or 0.1 to 0.5 mg cytotoxic agent/mg lipid, or 0.25 to 0.5 mg cytotoxic agent/mg lipid. In embodiments comprising a plurality of cytotoxic agents, the total amount of the cytotoxic agents present can range from 0.05 to 0.5 mg cytotoxic agent/mg lipid, such as 0.075 to 0.5 mg cytotoxic agent/mg lipid, or 0.1 to 0.5 mg cytotoxic agent/mg lipid, or 0.25 to 0.5 mg cytotoxic agent/mg lipid. In some embodiments, the cytotoxic agent can be present in an amount that provides a ratio of total lipid content to cytotoxic agent ("lipid:cytotoxic agent") ranging from 5:1 lipid:cytotoxic agent to 100:1 lipid:cytotoxic agent, such as 5:1 lipid:cytotoxic agent to 20:1 lipid:cytotoxic agent. In some embodiments, ratios of 5:1 lipid:cytotoxic agent, 10:1 lipid:cytotoxic agent, or 20:1 lipid:cytotoxic agent are used.

This disclosure includes pharmaceutical compositions comprising at least one vesicle described herein. Some embodiments of the disclosed pharmaceutical compositions, when irradiated with near-infrared energy, are capable of killing or inhibiting tumor cells, thereby eliminating a tumor, reducing tumor size, and/or inhibiting tumor growth. The pharmaceutical compositions may be applied to tumor cells in vitro, or the pharmaceutical composition may be formulated for use in human and/or veterinary medicine and may be applied to tumor cells in vivo by administering a therapeutically or diagnostically effective amount of the pharmaceutical composition to a subject.

Some embodiments of the pharmaceutical compositions include a pharmaceutically acceptable carrier and at least one active ingredient. Useful pharmaceutically acceptable carriers and excipients are known in the art. Active ingredients may comprise, for example, at least one vesicle embodiment as described herein, or any combination of vesicles as described herein (e.g., a combination of vesicles comprising one particular type of cytotoxic agent and vesicles comprising a different type of cytotoxic agent). In addition, other medicinal or pharmaceutical agents, for example, with similar, related or complementary effects on the affliction being treated, may be included as active ingredients in pharmaceutical compositions. These agents include, but are not limited to, pharmaceutical compounds, chemotherapeutic agents, cytokines, and anti-angiogenic agents.

The pharmaceutical compositions comprising one or more vesicles may be formulated in a variety of ways depending, for example, on the mode of administration and/or on the location and type of disease to be treated. For example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

Topical preparations may include eye drops, gels, ointments, creams, suspensions, sprays and the like as are well-known in the art.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the active ingredient may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some vesicle formulations may be dried, e.g., by spray-drying with a disaccharide, to form liposomal powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings that mitigate acid denaturation of the vesicle's binary lipid bilayer. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the active compound, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

For prolonged delivery, the vesicles can be formulated as a depot preparation for administration by implantation or intramuscular injection. Alternatively, transdermal delivery systems manufactured as an adhesive disc or patch which slowly releases the vesicle for percutaneous absorption may be used. To this end, permeation enhancers may be used to facilitate transdermal penetration of the active compound(s).

Certain embodiments of the pharmaceutical compositions comprising vesicles as described herein may be formulated in unit dosage form suitable for individual administration of precise dosages. The pharmaceutical compositions may, if desired, be presented in a pack or dispenser device which may contain one or more unit dosage forms containing the vesicles. The pack may, for example, comprise metal or plastic foil, such as a blister pack. The pack or dispenser device may be accompanied by instructions for administration. The amount of vesicles administered will depend on the subject being treated, the severity of the affliction (e.g., the size, location, and characteristics of a tumor), and the manner of administration, and is known to those skilled in the art. Within these bounds, the formulation to be administered will contain a quantity of the vesicles disclosed herein in an amount effective to achieve the desired effect in the subject being treated.

Embodiments of the disclosed vesicles will generally be used in an amount effective to achieve the intended result, for example in an amount effective to treat or image a tumor. The vesicles may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized. In some embodiments, the vesicles are administered to achieve diagnostic benefit. Diagnostic benefit includes, for example, the ability to image target tissue such as tumor tissue.

The amount administered will depend upon a variety of factors, including, for example, the particular indication being treated, the mode of administration, the severity of the indication being treated, the age and weight of the patient, the bioavailability of the particular bioactive agent included in the cavity of the vesicle, etc. Determination of an effective dosage is well within the capabilities of those skilled in the art.

Effective dosages may be estimated initially from in vitro assays. For example, an initial dosage may be formulated to achieve a tumor tissue concentration of reactive oxygen species produced by the cytotoxic agent embedded within the vesicle's bilayer that is sufficient to cause tumor cell necrosis as determined in an in vitro assay. In additional embodiments, an initial dosage may be formulated to achieve a tumor tissue concentration of a released cytotoxic agent following vesicle disruption that is sufficient to cause tumor cell necrosis as determined in an in vitro assay. Calculating dosages to achieve such concentrations is well within the capabilities of skilled artisans. For guidance, the reader is referred to Fingl & Woodbury, "General Principles," In: Goodman and Gilman's The Pharmaceutical Basis of Therapeutics, Chapter 1, pp. 1 46, latest edition, Pagamonon Press, and the references cited therein.

Initial dosages can also be estimated from in vivo data, such as animal models. Animal models useful for testing the efficacy of compounds to treat tumors are well-known in the art. A person having ordinary skill in the art, along with the benefit of the present disclosure, can adapt such information to determine dosages suitable for human administration.

Preferably, the vesicles will provide therapeutic or prophylactic benefit without causing substantial toxicity. Toxicity of the vesicles may be determined using standard pharmaceutical procedures. The dose ratio between toxic and therapeutic effect is the therapeutic index. Vesicles that exhibit high therapeutic indices are preferred.

Certain embodiments of the pharmaceutical methods and compositions include co-administration of the vesicle as described herein and a therapeutically effective amount of a second agent other than the vesicle. The vesicle and the second agent may be administered either separately or together in a single composition. The second agent may be, for example, an anti-tumor agent or an angiogenesis inhibitor.

IV. Methods of Making Vesicle Embodiments

Disclosed herein are embodiments of a method for making the vesicle embodiments of the present disclosure. The method can comprise using a probe sonication method to produce the vesicles. In some embodiments, the alkyne-containing phospholipid is combined with the PEGylated lipid in chloroform and they are mixed. Different ratios of the lipids can be used as described above, with exemplary ratios being provided by Tables 1 and 2 in the Examples section of the present disclosure.

A desired amount of the cytotoxic agent is added to the lipid mixture as a solution (e.g., a DMSO solution) prior to making a lipid film. Any solvents are removed (e.g., under nitrogen gas) and the resulting lipid films can be stored and/or allowed to further dry under an inert atmosphere. The dried lipid films are re-suspended using a buffer (e.g., 1 ml HBS, pH=7.4). The lipid mixture is vortexed and heated and then sonicated using a probe sonicator in an ice bath. In particular disclosed embodiments, the lipid mixture is vortexed and heated at 45-50° C. for 15-20 minutes and subjected to at least five freeze-thaw cycles. In such embodiments, a probe sonicator can be used, with particular embodiments using 5-10 cycles, with 1 minute per cycle followed by 1 minute of rest. Specific examples of making exemplary vesicles disclosed herein are described in detail in the Examples section of the present disclosure.

V. Methods of Using Vesicle Embodiments

A. Photoactivation

Embodiments of the disclosed vesicles are photoactivated (e.g., the cytotoxic agent is activated and/or lipid conformations in the bilayer are modified to facilitate cytotoxic agent release) by targeted application of light having a desired wavelength, intensity, and/or surface area to a preselected target area for an effective period of time. The wavelength is selected within the near-infrared range, e.g., from 650 nm to 2500 nm. When photoactivatable cytotoxic agents, such as HPPH, are used, the wavelength is selected from 650-670 nm. Suitable light intensities may range from 1 mW to 500 mW depending on the target site and method of application. In some examples, a 90 mW, 660 nm laser was used. Near-infrared light sources can be obtained from commercial sources, including Thorlabs (Newton, N.J.), Laser Components, USA (Hudson, NH), ProPhotonix (Salem, NH) and others.

In some embodiments, photoactivation is performed by externally applying light to a targeted area. NIR light is capable of penetrating transcutaneously into tissue to a depth of several centimeters. In other embodiments, photoactivation may be performed by internally applying light, such as by using an endoscope or a fiber optic catheter. Internal application may be used when the target tissue, such as a tumor, is located at a depth that is unsuitable for external light application. For example, an endoscope may be used for light delivery into the lungs, stomach, or bladder.

The surface area for light application is generally selected to include the target tissue, e.g., a tumor or portion of a tumor, or an area of skin external to the target tissue. When targeted, externally applied light is desired, the surface area can be controlled by using an appropriate light applicator, such as a micro-lens, a Fresnel lens, or a diffuser arrangement. For targeted, internally applied light, a desired endoscope or fiber optic catheter diameter can be used. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

In some embodiments, photoactivation is performed for a period of time effective to activate at least a portion of the cytotoxic agent, such as HPPH or other such photoactivable compounds, within the vesicle's binary lipid bilayer wall, thereby releasing reactive oxygen species that can act on the tumor cells. In yet additional embodiments, photoactivation can be performed for a period of time effective to activate a conformational change and/or oxidative change in a lipid of the binary lipid bilayer such that the binary lipid bilayer wall is destabilized. This destabilization can result in releasing at least a portion of an embedded cytotoxic agent, such as a camptothecin. In some embodiments, the effective period of time ranges from several seconds to several minutes, e.g., from 30 seconds to 15 minutes. In certain examples, photoactivation was performed for 5-10 minutes.

In particular embodiments, HPPH is used as the cytotoxic agent. HPPH is activated with near-infrared light energy, such as NIR light having a wavelength of 650 nm to 680 nm. For example, HPPH can be activated when irradiated for an effective period of time by a laser that produces light having a wavelength of 655 nm to 675 nm, e.g., a 660-nm laser. In certain embodiments, HPPH is activated when irradiated with a continuous wave (cw)-diode 600 nm laser source (90 mV) for several seconds to several minutes.

B. Applications

Embodiments of the disclosed vesicle are suitable for in vitro uses and/or in vivo administration to a subject. As described above, at least a portion of the embedded cytotoxic agent is activated to promote reactive oxygen species formation and/or to promote changes in vesicle morphology so that another embedded cytotoxic agent can be released upon irradiation with light (e.g., near-infrared light energy) for an effective period of time.

Figure 2:
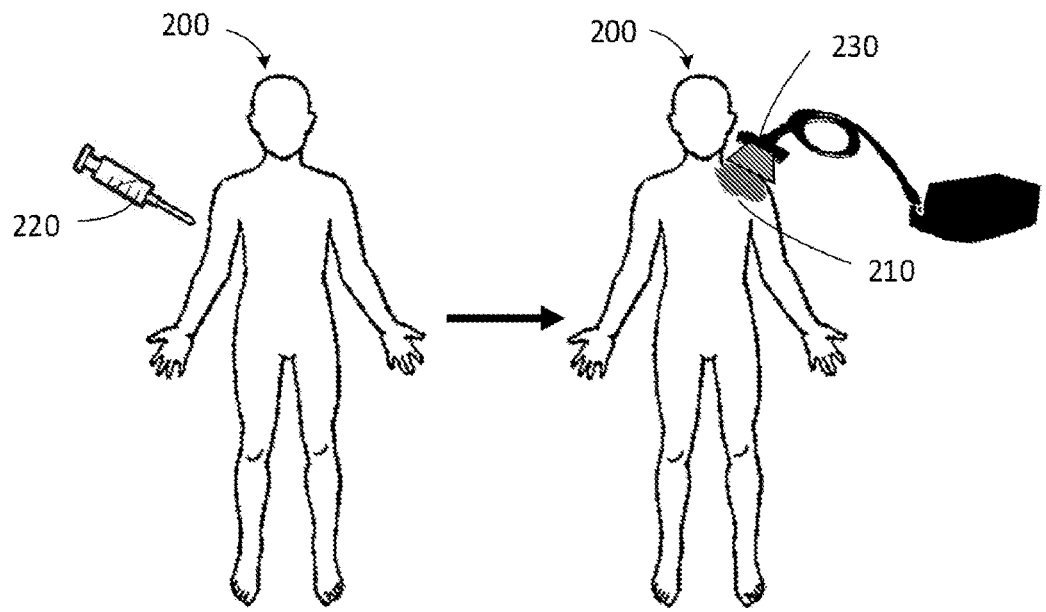
FIG. 2 is a schematic diagram illustrating one embodiment of a method for using the disclosed vesicles to treat a subject having a tumor by injecting the vesicles followed by targeted delivery of light of a desired wavelength to the external surface of the subject's skin.

In particular disclosed embodiments, the disclosed vesicle may be administered to a subject identified as having a condition that may be treated with a cytotoxic agent, such as HPPH (or other tetrapyrrollic compounds, such as chlorin e6) or a camptothecin compound. For example, with reference to FIG. 2, a subject 200 with a tumor may be treated with vesicle embodiments comprising HPPH embedded in the cavity. Administration of the disclosed vesicle to the subject may impair growth of the tumor and/or cause tumor regression. Because the disclosed vesicles have high amounts of a PEGylated lipid, the vesicles preferentially are taken up by and accumulate in the tumor 210. A therapeutically effective amount of the vesicles, or a pharmaceutical composition comprising the vesicles, is administered to the subject by any suitable means including, but not limited to, parenteral, intravenous, subcutaneous, oral, rectal, vaginal, or topical administration. In the example shown in FIG. 2, the vesicles 220 are administered via intravenous injection. A target portion of the subject subsequently is selectively irradiated with NIR light energy of a desired wavelength using an external light applicator 230 for an effective period of time, such as from 1-15 minutes. The light applicator 230 applies the photoactivation energy to a target area limited to the region of the tumor 210, thereby selectively photoactivating the vesicles in and around the tumor 210 and targeting delivery of reactive oxygen species generated from the HPPH.

The embedded cytotoxic agent can inhibit tumor cell growth and/or kill tumor cells, thereby providing combination chemotherapy to the tumor site. Suitable tumor sites include, but are not limited to, the head, neck, skin, bladder, prostate, colon, and lung. Because the cytotoxic agents and/or reactive oxygen species generated by the cytotoxic agents are released directly at the tumor site, the cytotoxic agent's effectiveness may be increased and/or the cytotoxic agent's side effects may be reduced compared to other methods of non-targeted administration.

In a particular disclosed embodiments, colon-26 bearing BALB/c mice, intravenously injected with Vesicle$_{20}$-HPPH showed superior PDT efficacy and animal survival (no tumor recurrence up to 100 days) as compared to a formulation currently used in clinical trials, namely Tween 80-HPPH. Additionally and advantageously, the vesicles exhibited stability for 60 days upon storage at room temperature and also were shown to preferentially accumulate in tumor xenografts in HT29 tumor bearing athymic mice. Similar accumulation confirmation was observed in A549 tumor-bearing mice. Additional details are discussed in the Examples section of the present disclosures.

Embodiments of the disclosed vesicles also may be useful as nano-imaging tools, pathogen diagnostics, oral vaccines, and biomimetics.

VI. Overview of Several Embodiments

Disclosed herein are embodiments of a vesicle for therapeutic use. In some embodiments, the vesicle comprises a binary lipid bilayer comprising an alkyne-containing phospholipid and a PEGylated lipid; and a cytotoxic agent embedded in the binary lipid bilayer; wherein the binary lipid bilayer is free of, or does not comprise, a lipid other than the alkyne-containing phospholipid or the PEGylated lipid.

In any or all of the above embodiments, the binary lipid bilayer comprises greater than 6 mol % to 20 mol % of the PEGylated lipid.

In any or all of the above embodiments, the binary lipid bilayer comprises 10 mol % to 20 mol % of the PEGylated lipid.

In any or all of the above embodiments, the alkyne-containing phospholipid and the PEGylated lipid, taken together, and the cytotoxic agent are present at a ratio of 1:0.05 (total lipid:cytotoxic agent).

In any or all of the above embodiments, the alkyne-containing phospholipid is an alkyne-containing phosphocholine lipid or a mixture of the alkyne-containing phosphocholine lipid and an alkyne-containing phosphoethanolamine lipid.

In any or all of the above embodiments, the alkyne-containing phosphocholine lipid is 1,2-bis(tricosa-10,12-diynoyl)-sn-glycero-3-phosphocholine ($DC_{8,9}PC$) and wherein the alkyne-containing phosphoethanolamine lipid is 1,2-bis(10,12-tricosadiynoyl)-sn-glycero-3-phosphoethanolamine ($DC_{8,9}PE$).

In any or all of the above embodiments, the PEGylated lipid is a PEGylated 1,2-distearoyl-sn-glycero-3-phosphoethanolamine (DSPE) lipid comprising a PEG group having a molecular weight ranging from 500 Da to 5000 Da.

In any or all of the above embodiments, the PEGylated lipid is a PEGylated DSPE lipid comprising a PEG group having a molecular weight ranging from 1000 Da to 3000 Da.

In any or all of the above embodiments, the PEGylated lipid is 1,2-distearoyl-sn-glycero-3-phosphoethanolamine-N-methoxy(polyethylene glycol)-2000 (DSPE-PEG2000).

In any or all of the above embodiments, the cytotoxic agent is a tetrapyrrollic compound, a camptothecin compound, paclitaxel, daunorubicin, methotrexate, vincristine, etoposide, sorafenib, erlotinib, imatinib, or any combination thereof.

In any or all of the above embodiments, the tetrapyrrollic compound is 2-[1-hexyloxyethyl]-2-devinyl pyropheophorbide-a (HPPH), (17S,18S)-18-(2-carboxyethyl)-20-(carboxymethyl)-12-ethenyl-7-ethyl-3,8,13,17-tetramethyl-17,18,22,23-tetrahydroporphyrin-2-carboxylic acid (Ce6), (3S,4S)-9-Ethenyl-14-ethyl-21-(methoxycarbonyl)-4,8,13,18-tetramethyl-20-oxo-3-phorbinepropanoic acid (Pheophorbide a); 3,3',3'',3'''-(2,3-dihydroporphyrin-5,10,15,20-tetrayl)tetraphenol (Temoporfn), 3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1^3,6.1^8,11.1^13,16.0^19,24]octacosa-1,3,5,7,9,11(27),12,14,16,18(25),19,21-dodecaen-9-yl]propanoic acid (Verteporfin), or any combination thereof.

In any or all of the above embodiments, the camptothecin compound is camptothecin, silatecan 7-t-butyldimethylsilyl-10-hydroxycamptothecin (DB-67), 7-ethyl-10-hydroxy-20(S)-camptothecin (SN-38), topotecan, irinotecan, 9-nitro-camptothecin, lurtotecan, exatecan, gimatecan, or karenitecin.

In any or all of the above embodiments, the vesicle comprises a binary lipid bilayer consisting of an alkyne-containing lipid, a PEGylated lipid and a cytotoxic agent embedded within the binary lipid bilayer.

Also disclosed herein are embodiments of a vesicle comprising a binary lipid bilayer comprising (i) DSPE-PEG2000 and (ii) $DC_{8,9}PC$, or a combination of $DC_{8,9}PC$ and $DC_{8,9}PE$; and HPPC, Ce6, and/or camptothecin embedded in the binary lipid bilayer; and wherein the binary lipid bilayer is free of, or does not comprise, a lipid other than the $DC_{8,9}PC$, the $DC_{8,9}PE$, and the DSPE-PEG2000.

Also disclosed herein are methods of using any of the vesicle embodiments disclosed herein. In some embodiments, the method comprises providing a vesicle according to any one or all of the above vesicle embodiments; and irradiating the vesicle with targeted application of light having a selected wavelength in the near-infrared range and a selected intensity for an effective period of time to activate at least a portion of the cytotoxic agent.

In any or all of the above embodiments, irradiating the vesicle with targeted application of light comprises irradiating the vesicle with a laser that produces light having a wavelength of 650-670 nm.

In any or all of the above embodiments, the selected intensity is from 1 mW to 500 mW.

In any or all of the above embodiments, the effective period of time is at least 30 seconds.

In any or all of the above embodiments, the method further comprises identifying a subject as having a condition that may be treated with the cytotoxic agent; administering the vesicle to the subject; and wherein the targeted application of light is directed at a targeted portion of the subject.

In any or all of the above embodiments, the subject has a tumor and the targeted portion of the subject includes an area proximate a location of the tumor.

In any or all of the above embodiments, administering the vesicle to the subject comprises administering an amount of the vesicle effective to induce tumor size regression.

In any or all of the above embodiments, irradiating is performed 4-6 hours after administering the vesicle to the subject.

In any or all of the above embodiments, administering the vesicle to the subject comprises intravenously injecting the vesicle into the subject.

In any or all of the above embodiments, administering the vesicle to the subject comprises administering a pharmaceutical composition comprising the vesicle to the subject.

In any or all of the above embodiments, the targeted application of light occurs by externally applying the light to the targeted portion of the subject for the effective period of time, thereby transcutaneously applying the light to the tumor.

In any or all of the above embodiments, the targeted application of light occurs by internally applying the light to the targeted portion of the subject for the effective period of time.

In any or all of the above embodiments, light is applied internally using an endoscope or a fiber optic catheter.

Also disclosed herein are embodiments of a method for impairing growth of a tumor in a subject. In some embodiments, the method comprises administering to the subject a therapeutically effective amount of a vesicle according to any or all of the above vesicle embodiments; and irradiating the vesicle by targeted application of light having a selected wavelength in the near-infrared range and a selected intensity to a target area of the subject proximate a location of the tumor for an effective period of time to activate at least a portion of the cytotoxic agent to promote reactive oxygen species formation, thereby impairing growth of the tumor.

In any or all of the above embodiments, the effective period of time is at least 30 seconds.

In any or all of the above embodiments, irradiating is performed 4-6 hours after administering the vesicle to the subject.

In any or all of the above embodiments, administering the vesicle to the subject comprises administering an amount of the vesicle effective to induce tumor size regression.

In any or all of the above embodiments, administering the vesicle to the subject comprises intravenously injecting the vesicle into the subject.

In any or all of the above embodiments, administering the vesicle to the subject comprises administering a pharmaceutical composition comprising the vesicle to the subject.

In any or all of the above embodiments, irradiating the vesicle by targeted application of light comprises externally or internally applying the light to the targeted portion of the subject for the effective period of time.

In any or all of the above embodiments, the light is applied internally using an endoscope or a fiber optic catheter.

VII. Examples

Lipids were from Avanti Polar Lipids, Inc. (Alabaster, Ala., USA). PD10 and Sepharose CL-6B were from GE Healthcare (Pittsburgh, Pa., USA). DiR (DiIC18) (7) was from Life Technologies (Grand Island, NY, USA). All other materials were of reagent grade. 2-[1-hexyloxyethyl]-2-devinyl pyropheophorbide-α (HPPH) was synthesized by Dr. Gary Pauly (Chemistry Core, Chemical Biology laboratory, CCR).

Cells—HT29 (human colorectal adenocarcinoma) cells were obtained from the National Cancer Institute 60 cells lines repository. Murine CT-26 colon carcinoma cells were purchased from American Type Culture Collection (ATCC, Manassas, VA). The cells were maintained in DMEM supplemented with 10% FBS, 100 i.u./ml penicillin and 100 μg/mL streptomycin in 5% $CO_2$ at 37° C.

Figure 3A:
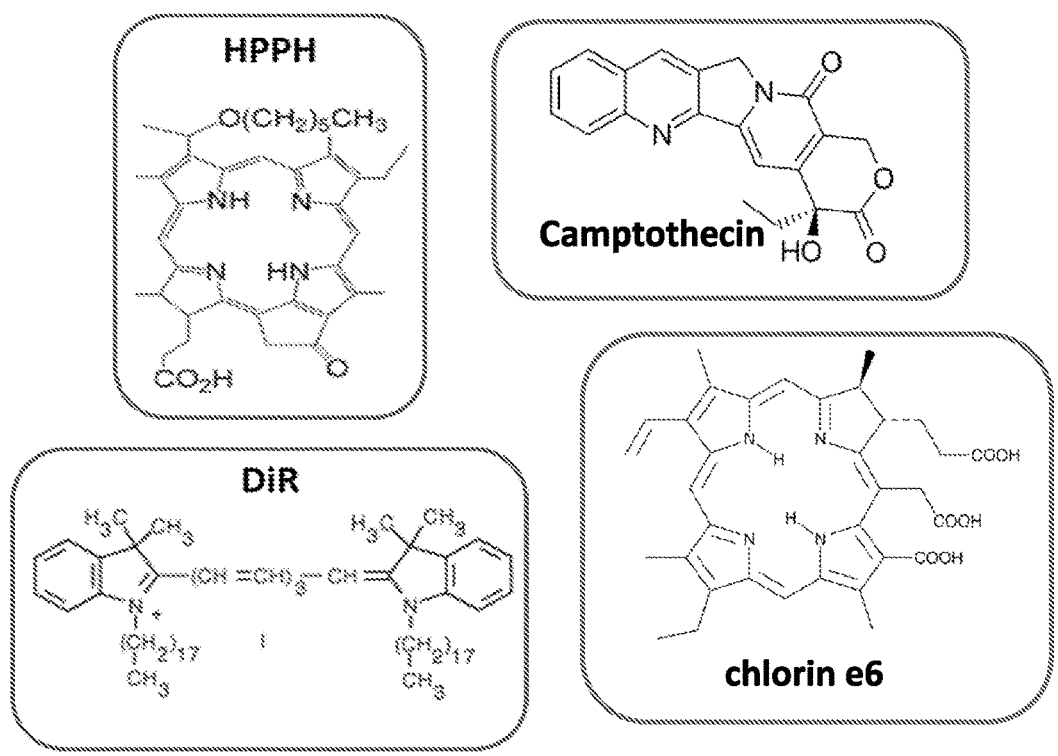
FIGS. 3A and 3B provide chemical structures of 2-[1-hexyloxyethyl]-2-devinyl pyropheophorbide-a (HPPH), (17S,18S)-18-(2-carboxyethyl)-20-(carboxymethyl)-12-ethenyl-7-ethyl-3,8,13,17-tetramethyl-17,18,22,23-tetrahydroporphyrin-2-carboxylic acid (or "chlorin e6" or "Ce6"), 1,1'-dioctadecyl-3,3,3',3'-tetramethylindotricarbocyanine iodide (DiR), and Camptothecin (FIG. 3A); 1,2-bis(tricosa-10,12-diynoyl)-sn-glycero-3-phosphocholine ($DC_{8,9}PC$), dipalmitoylphosphatidylcholine (DPPC), distearoylphosphatidylethanolamine-polyethylene glycol (DSPE-PEG), and 1,2-bis(10,12-tricosadiynoyl)-sn-glycero-3-phosphoethanolamine ($DC_{8,9}PE$) (FIG. 3B).
Figure 3B:
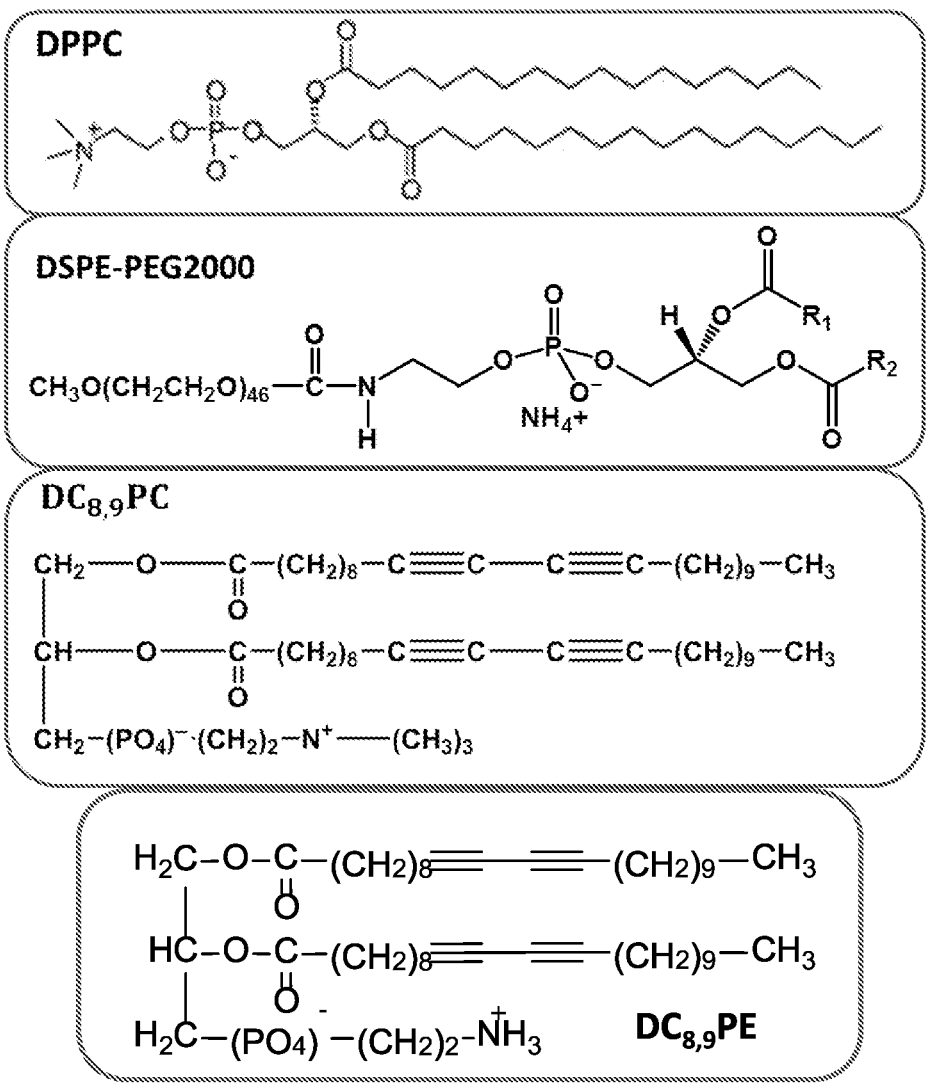

Preparation of Vesicles—Chemical structures of various molecules (see FIGS. 3A and 3B), details of vesicle preparation (FIG. 4), their purification protocol (FIGS. 5 and 6), and characterization (e.g., FIGS. 4, 7A, 7B, 8, 24) are described herein. The following set of vesicles were prepared:

(a) PEGylated lipid-$DC_{8,9}PC$ vesicles: Vesicles containing $DC_{8,9}PC$ and DSPE-PEG2000 at various mole ratios (0-50 mol % PEGylated lipid) were prepared by probe sonication. Various formulations tested in this study are shown in Table 1 ($Vesicle_0$-$Vesicle_{50}$).

Figure 6:
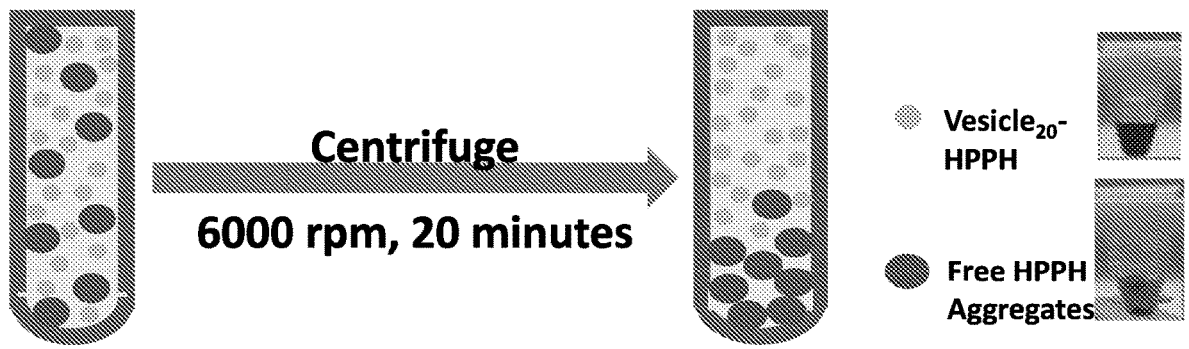
FIG. 6 is a schematic illustration of the centrifugation technique used to generate the data shown by FIG. 5.
Figure 7A:
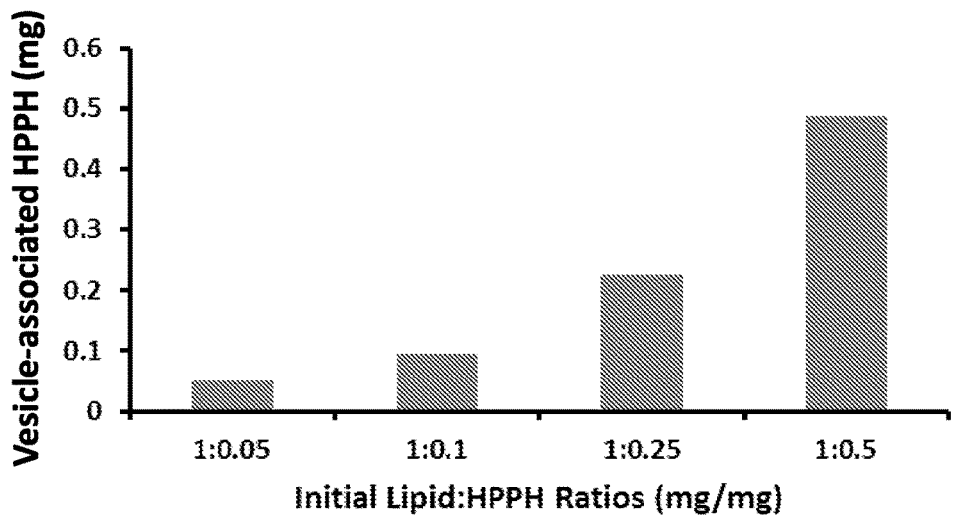
FIGS. 7A and 7B shows results from analyzing HPPH concentration in exemplary vesicle embodiments, wherein HPPH was included at various weight ratios for a known lipid concentration (typically 5 or 10 mg lipids were used) and vesicles were prepared by sonication and unincorporated HPPH were removed by centrifugation.
Figure 7B:
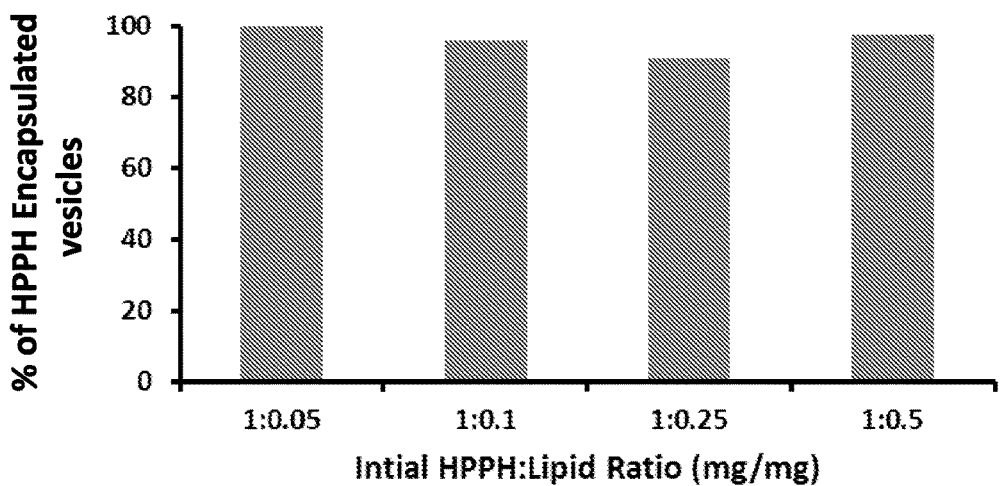

(b) HPPH-Vesicles: Vesicles that contained 10 or 20 mol % of DSPE-PEG2000 ($Vesicle_{10}$ and $Vesicle_{20}$) (Table 1) were used to load HPPH (Table 2). HPPH was included during the formation of lipid films. Various amounts of HPPH (ranging from 0-0.5 mg HPPH/mg lipid) were tested to optimize efficiency of drug incorporation in the vesicles (FIGS. 7A and 7B). A simple and new method for separating unincorporated HPPH based on low speed centrifugation (FIG. 6) also was used. In additional examples, PEGylated lipid-$DC_{8,9}PC$-$DC_{8,9}PE$ vesicles that contained 20:1 (w/w) or 100:1 (w/w) lipid:HPPH were made. In additional examples, vesicles containing HPPH and PEGylated lipids with different PEG groups were prepared by probe sonication: (a) $DC_{8,9}PC$ and DSPE-PEG350 (10 mol % PEGylated lipid, 20:1 w/w lipid:HPPH); (b) $DC_{8,9}PC$ and DSPE-PEG1000 (10 mol % PEGylated lipid, 20:1 w/w lipid: HPPH); (c) or $DC_{8,9}PC$ and DSPE-PEG5000 at various mole ratios (1, 5, and 10 mol % PEGylated lipid, 20:1 w/w lipid:HPPH). These various formulations are summarized in Tables 4 and 5.

(c) HPPH-DiR-Vesicles: For mouse-imaging studies, 0.5 mol % of a near IR mouse imaging lipid, DiR (Ex/Em 750/780 nm) was included in the $Vesicle_{10}$ and $Vesicle_{20}$. HPPH was incorporated at 0.05 mg HPPH per mg total lipid (Table 2, $Vesicle_{10}$-HPPH/DiR and $Vesicle_{20}$-HPPH/DiR). A formulation containing 4 mol % of the PEG lipid (DPPC: $DC_{8,9}PC$/DiR vesicles, Table 2) was used for comparison.

(d) PEGylated lipid-$DC_{8,9}PC$-$DC_{8,9}PE$ vesicles: Vesicles containing $DC_{8,9}PC$, $DC_{8,9}PE$, and DSPE-PEG2000 at a 65:25:10 mole ratio ($DC_{8,9}PC$:$DC_{8,9}PE$:DSPE-PEG2000) were prepared by probe sonication. Exemplary embodiments are summarized in Table 3.

(b) Ce6-Vesicles: Vesicles that contained $DC_{8,9}PC$:DSPE-PEG2000 at a mole ratio of $DC_{8,9}PC$:DSPE-PEG2000 were used to load Ce6 at amounts ranging from 5:1 (w/w), 10:1 (w/w), and 20:1 (w/w) lipid:Ce6. These embodiments are summarized in Table 6.

TABLE 1

| Formulation Designation | $DC_{8,9}PC$:DSPE-PEG2000 Mole Ratio | Vesicle Formation | UV (254 nm)-triggered cross-linking |
|---|---|---|---|
| Vesicle$_0$ | 100:0 | No | Yes |
| Vesicle$_{10}$ | 90:10 | Yes | Yes |
| Vesicle$_{20}$ | 80:20 | Yes | Yes |
| Vesicle$_{30}$ | 70:30 | No | No |
| Vesicle$_{40}$ | 60:40 | No | No |
| Vesicle$_{50}$ | 50:50 | No | No |

TABLE 2

Figure 11A:
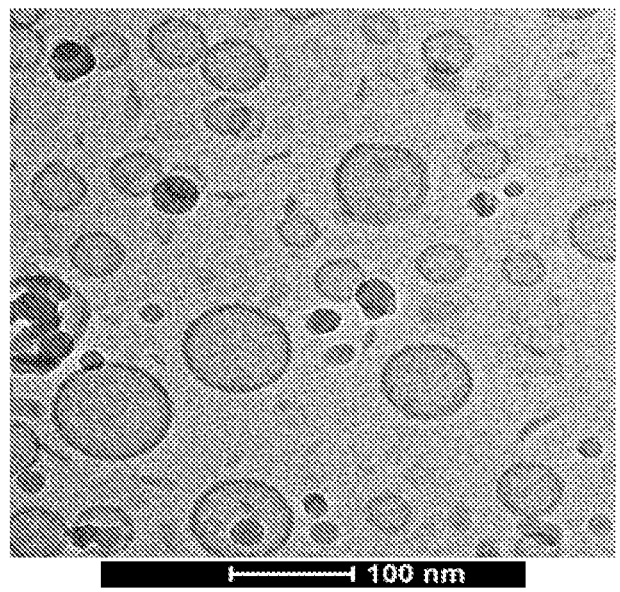
FIGS. 11A and 11B are cryo-electron micrograms of a vesicle that does not comprise an embedded cytotoxic agent (Vesicle$_{20}$.
Figure 11B:
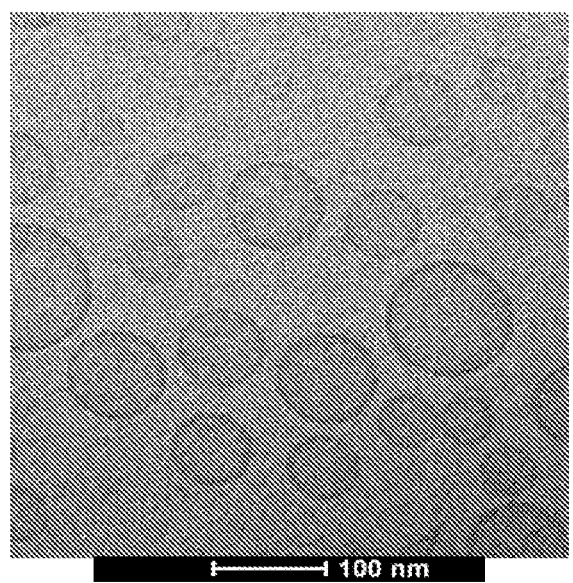
Figure 12A:
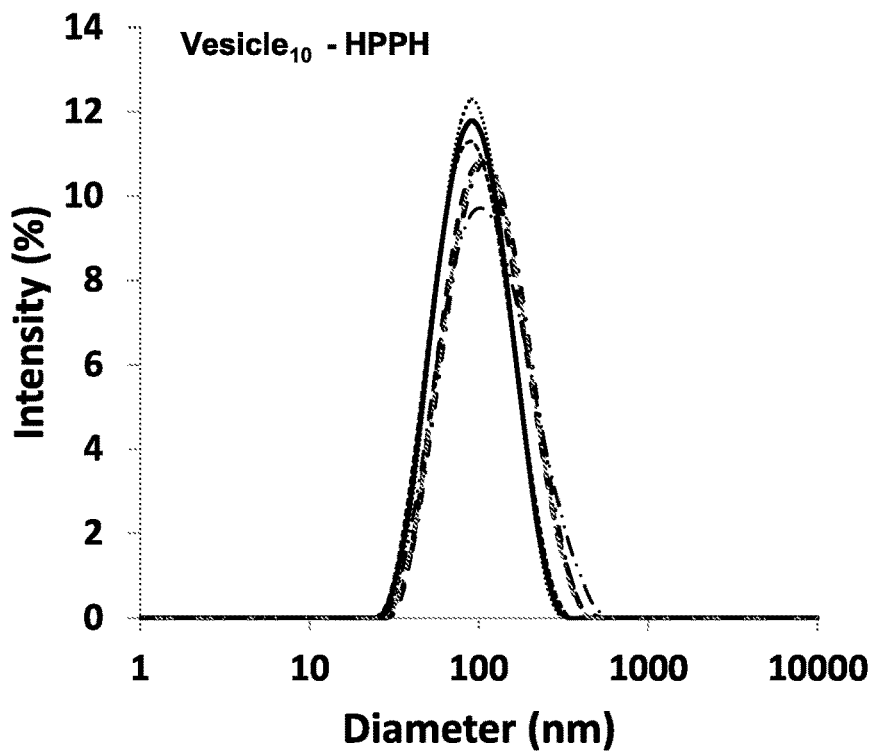
FIGS. 12A and 12B are graphs of intensity (%) as a function of diameter (nm) which show the evolution of hydrodynamic size (as monitored as a function of time using dynamic light scattering) of two representative vesicle embodiments, Vesicle$_{10}$-HPPH (FIG. 12A) and Vesicle$_{20}$-HPPH (FIG. 12B).
Figure 12B:
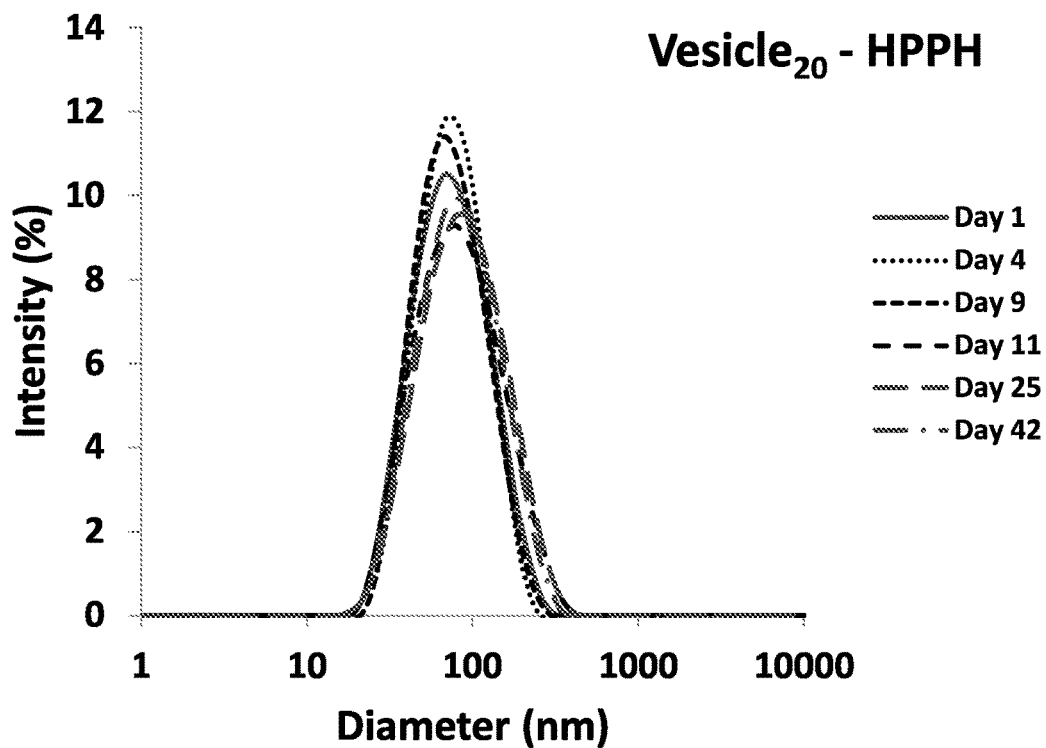
Figure 13:
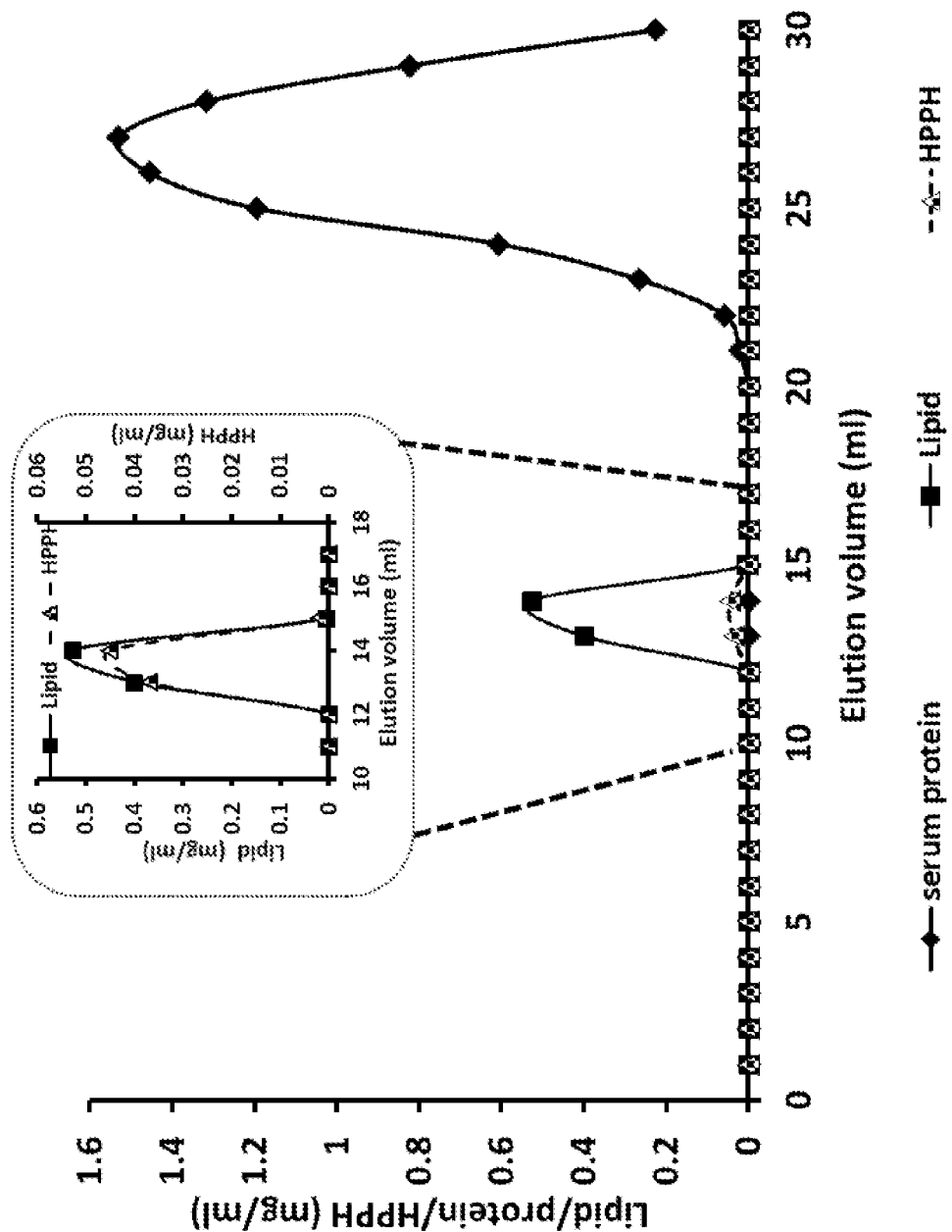
FIG. 13 is a graph showing the relative distribution of vesicles comprising HPPH upon incubation with fetal bovine serum and that illustrates that vesicle embodiments described herein have high serum stability as most of the detectable HPPH remains embedded within the binary lipid bilayer and the lipid:HPPH ratio remains unaffected in the vesicle fractions; Vesicle$_{20}$-HPPH vesicles were prepared at 1:0.1 lipid:HPPH ratios (w/w) and incubated with FBS at 37° C. for 2 hours, fractionated on a Sepharose CL-6B and fractions were collected after which the lipid Pi, HPPH, and protein in each fraction were determined; the inset shows a magnified version for lipid and HPPH (mg/ml) in vesicle fractions (10-18 ml fractions).
Figure 14A:
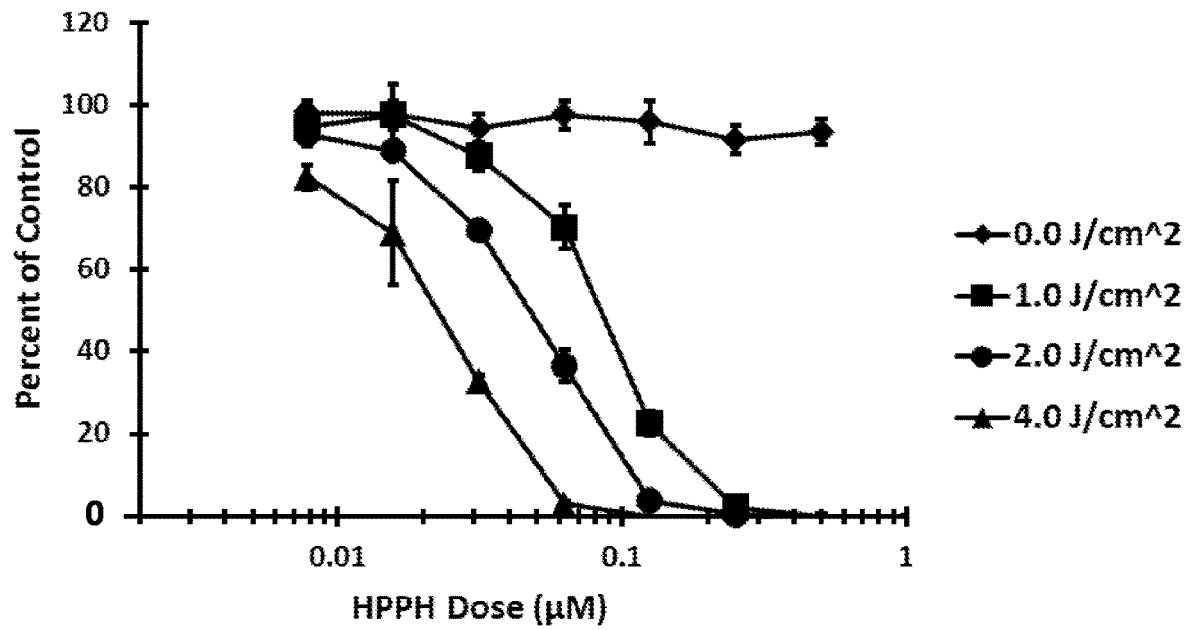
FIGS. 14A and 14B are graphs showing results from evaluating in vitro cytotoxicity of CT-26 cells by a vesicle embodiment, Vesicle$_{20}$-HPPH, after 4 hours (FIG. 14A) and after 24 hours (FIG. 14B) of incubation; cells on 96-well clusters were incubated with various doses of Vesicle$_{20}$-HPPH and laser treatments were done either at 4 hours or 24 hours post incubations; laser treatments doses used were either 0, 1, 2, or 4 J/cm$^2$ and cell viability was done using MTT Assays; results are presented as viability, taking untreated control cells as 100% viable.
Figure 14B:
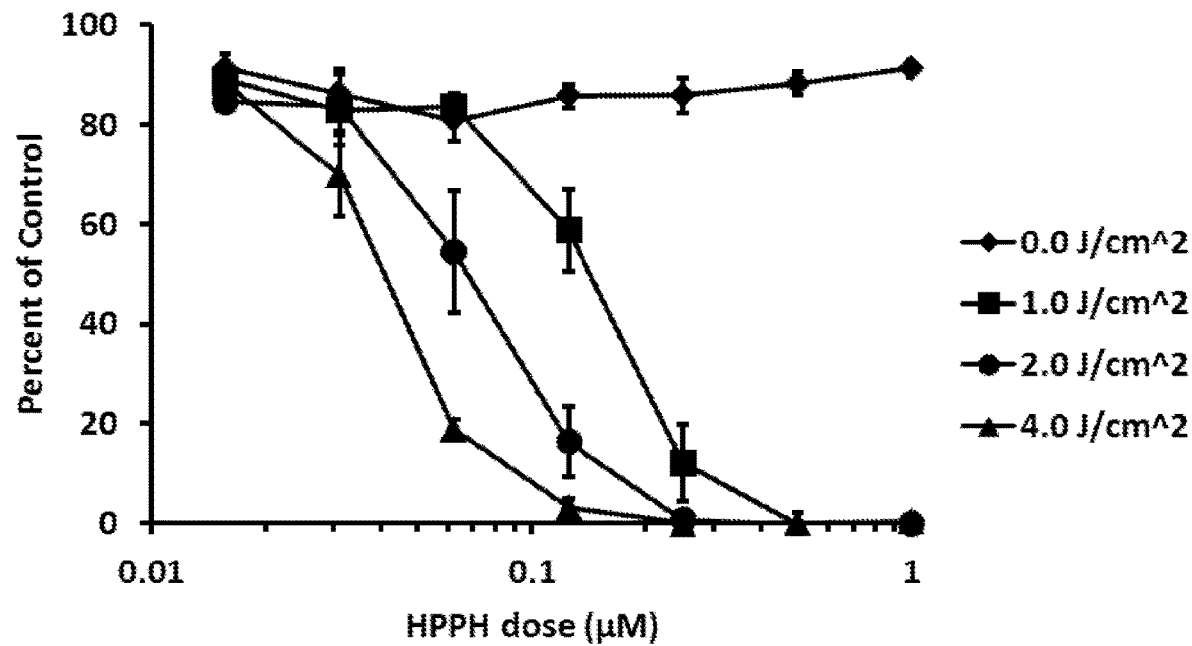
Figure 15:
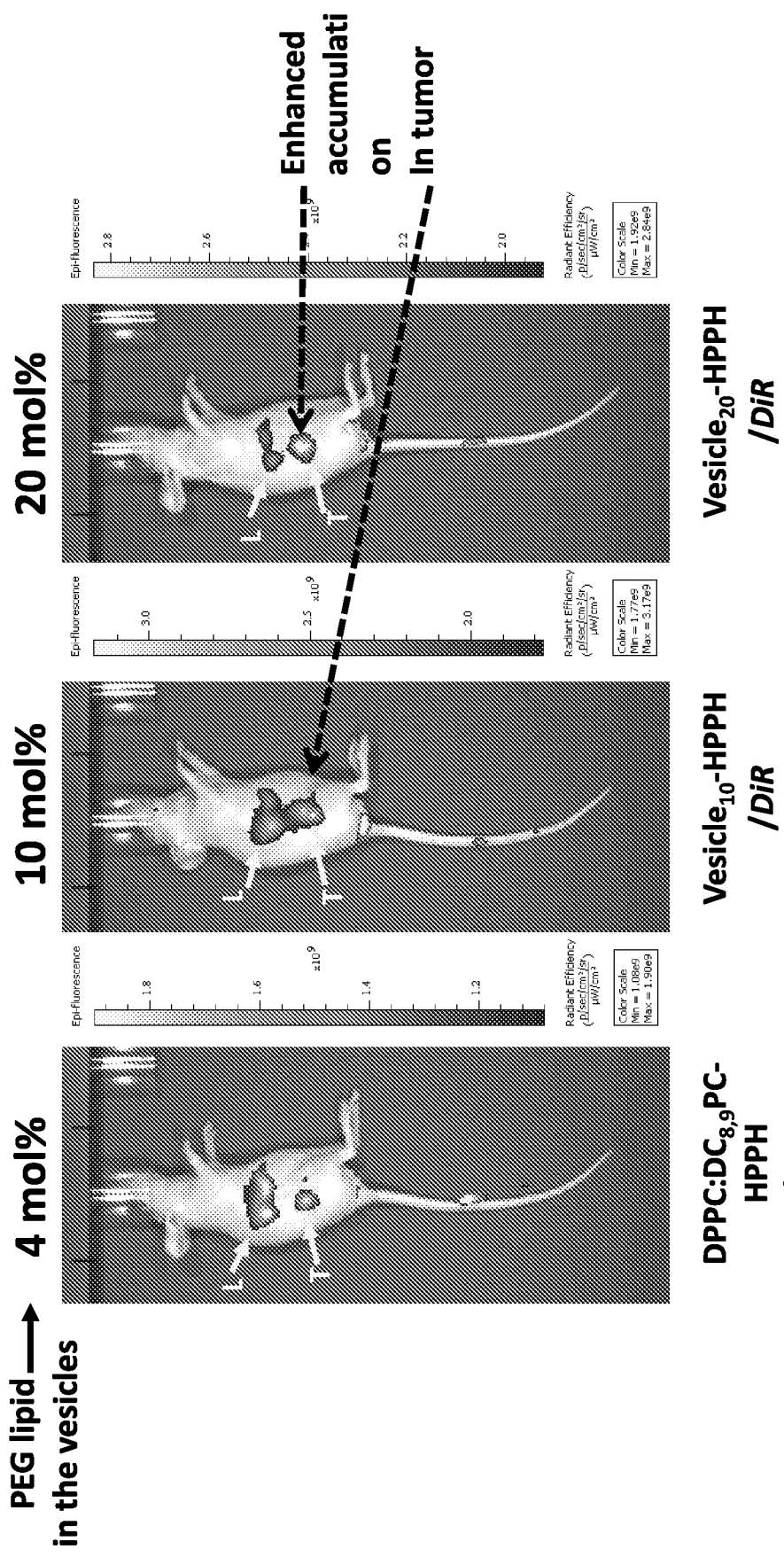
FIG. 15 provides in vivo images of mice (imaged using whole body DiR dorsal 2D-multispectral fluorescence imaging) that were injected with vesicle embodiments comprising DiR and HPPH and which establish that disclosed vesicle embodiments exhibit enhanced accumulation in tumors as compared to a liposome comprising DPPC and $DC_{8,9}PC$ lipids and a low amount of a PEGylated lipid; to generate the results, athymic nu/nu mice were injected in the flank with HT29 cells and upon tumors reaching ~100 mm$^3$, 0.2 ml of the vesicles (containing 1 mg total lipid) were injected intravenously and DiR imaging was performed post 4 hours injections; "L"=liver; "T"=tumor.
Figure 16A:
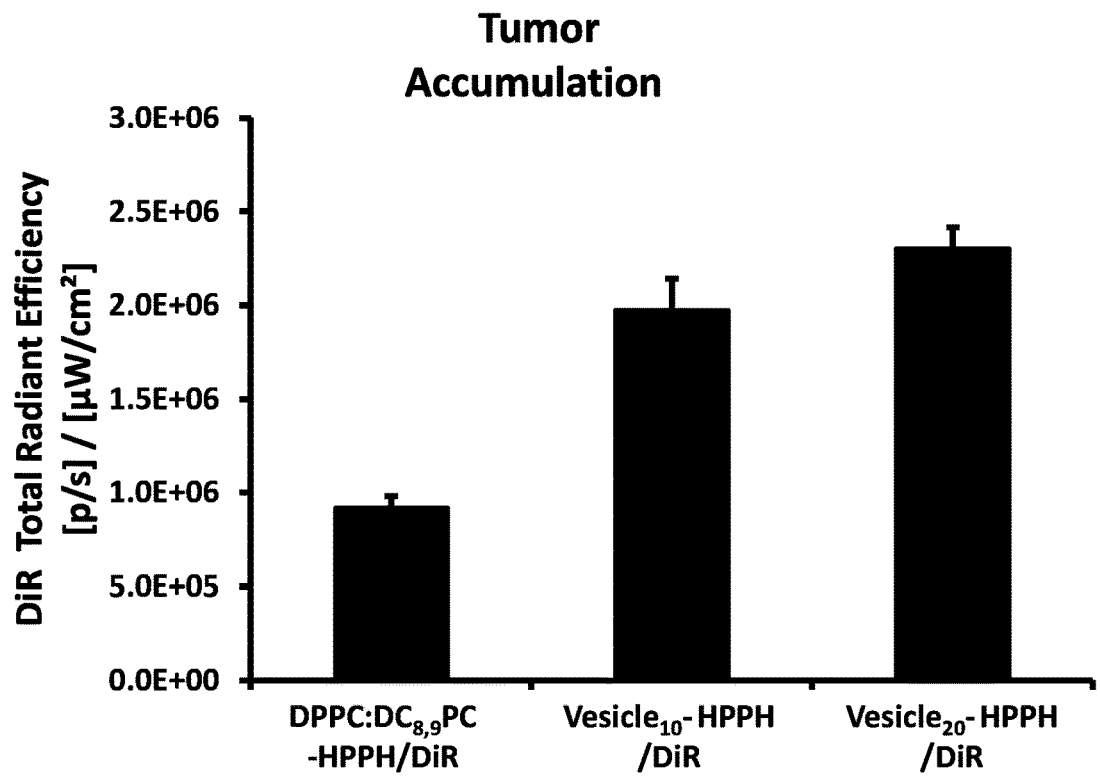
FIGS. 16A and 16B are graphs showing results of tumor accumulation of different vesicle embodiments disclosed herein (as well as a comparative liposome comprising DPPC and $DC_{8,9}PC$ lipids and a low amount of a PEGylated lipid) and relative accumulation of the vesicle embodiments in tumors versus the liver; quantitation of the DiR fluorescence in the tumor or liver was done taking average for the four mice per group.
Figure 16B:
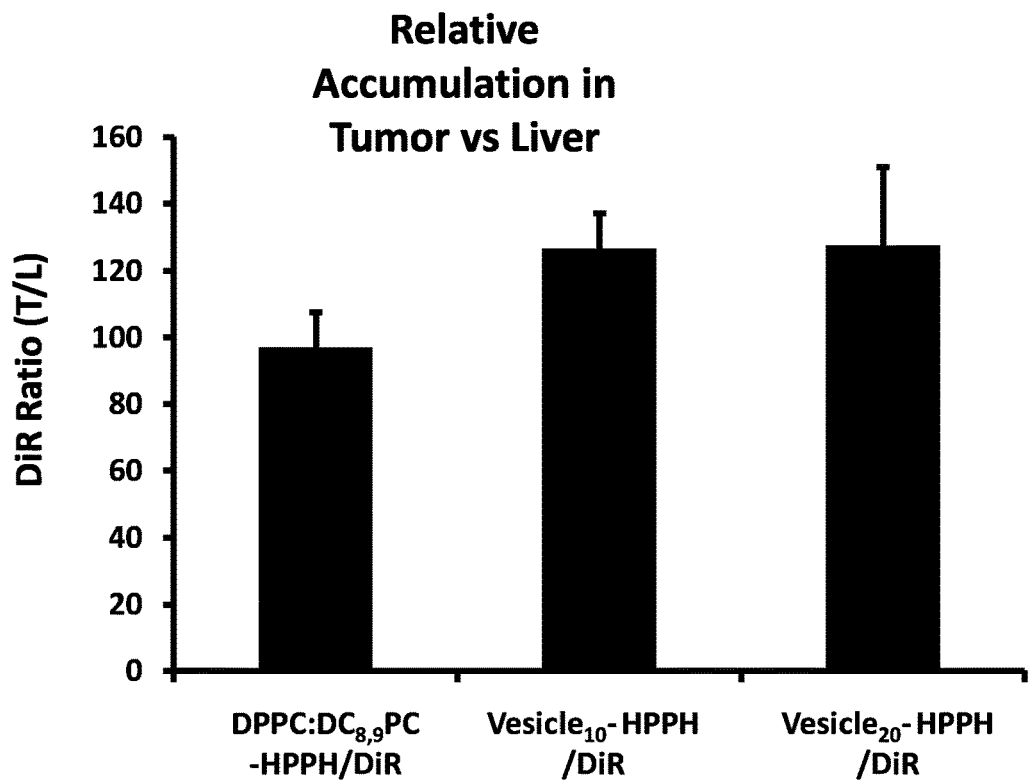

| Formulation Description* | Lipid Composition | Mole ratio of lipids (%) | DIR (mol %) | FIG. Number |
|---|---|---|---|---|
| Vesicle$_{10}$-HPPH | $DC_{8,9}PC$:DSPE-PEG2000 | 90:10 | none | FIGS. 12A, 12B, and 13 |
| Vesicle$_{20}$-HPPH | n/a | 80:20 | none | FIGS. 9A-9C, 11A, 11B, 12A, 12B, 14A, and 14B |
| Vesicle$_{10}$-HPPH/DIR | n/a | 90:10 | 0.5 | FIGS. 15, 16A, and 16B |
| Vesicle$_{20}$-HPPH/DIR | n/a | 80:20 | 0.5 | FIGS. 15, 16A, and 16B |
| DPPC:$DC_{8,9}PC$-HPPH/DIR | DPPC:$DC_{8,9}PC$:DSPE-PEG2000 | 86:10:04 | 0.5 | FIGS. 15, 16A, and 16B |

*Ratio of lipid: HPPH (mg/mg) in all formulations was 1:0.05.

TABLE 3

| Lipid Composition (mole ratios) | Lipid: HPPH ratios) (w/w) | Size/PDI Day 1 | Size/PDI, Day 7 | Size/PDI, 4 months |
|---|---|---|---|---|
| $DC_{8,9}PC$:$DC_{8,9}PE$:DSPE-PEG2000 (65:25:10) | 20:1 | 95.16 ± 0.157 0.192 ± 0.005 | 93.37 ± 0.592 0.183 ± 0.008 | 95.19 ± 0.456 0.191 ± 0.007 |
| $DC_{8,9}PC$:$DC_{8,9}PE$:DSPE-PEG2000 (65:25:10) | 100:1 | 91.67 ± 0.968 0.176 ± 0.009 | 89.15 ± 1.08 0.158 ± 0.006 | 93.41 ± 0.838 0.165 ± 0.011 |

TABLE 4

| Lipid Composition (mole ratios) | Lipid: HPPH ratios) (w/w | Diameter (nm)/PDI Day 1 | Diameter (nm)/PDI Day 7 | Diameter (nm)/PDI 4 months |
|---|---|---|---|---|
| $DC_{8,9}PC$:DSPE-PEG5000 (90:10) | 20:1 | 99.92 ± 1.00 0.218 ± 0.004 | 101.9 ± 0.929 0.230 ± 0.020 | 119 ± 2.27 0.262 ± 0.011 |
| $DC_{8,9}PC$:DSPE-PEG5000 (95:05) | 20:1 | 91.94 ± 0.395 0.217 ± 0.004 | 98.57 ± 1.14 0.225 ± 0.021 | n.d. |
| $DC_{8,9}PC$:DSPE-PEG5000 (99:01) | 20:1 | 97.88 ± 1.24 0.352 ± 0.013 | 164.1 ± 16.9 0.639 ± 0.13 | n.d. |

TABLE 5

| Lipid Composition (mole ratios) | Lipid: HPPH ratios (w/w) | Diameter (nm)/PDI Day 1 | Diameter (nm)/PDI Day 7 | Diameter (nm)/PDI 4 months |
|---|---|---|---|---|
| $DC_{8,9}PC$:DSPE-PEG1000 (90:10) | 20:1 | 90.77 ± 0.308 0.214 ± 0.003 | 94.52 ± 0.809 0.239 ± 0.003 | 110 ± 1.10 0.330 ± 0.031 |
| $DC_{8,9}PC$:DSPE-PEG350 (90:10) | 20:1 | 644.3 ± 28.76 0.682 ± 0.045 | 685.7 ± 151.251 ± 0 | 899.2 ± 39.87 1 ± 00 |

TABLE 6

| Lipid Composition (mole ratios) | Lipid:Ce6 ratios (w/w) | Diameter (nm)/ PDI Day 1 | Diameter nm)/PDI, Day 7 |
|---|---|---|---|
| DC$_{8,9}$PC:DSPE-PEG2000 (90:10) | 5:1 | 80.05 ± 3.95 0.240 ± 0.058 | 153.8 ± 1.27 0.390 ± 0.055 |
| DC$_{8,9}$PC:DSPE-PEG2000 (90:10) | 10:1 | 145.5 ± 0.814 0.386 ± 0.009 | 140.6 ± 1.17 0.402 ± 0.007 |
| DC$_{8,9}$PC:DSPE-PEG2000 (90:10) | 20:1 | 93.49 ± 0.52 0.209 ± 0.006 | 93.72 ± 0.782 0.218 ± 0.014 |

Briefly, lipids (in chloroform) were mixed in glass tubes. For vesicles containing HPPH, desired amounts of HPPH from a DMSO stock (at 10-100 mg/ml) were added to the lipid mixtures prior to making the lipid films. Solvents were removed under nitrogen gas and the lipid films were kept overnight in a desiccator at room temperature to remove traces of the solvent. Typically, vesicles were prepared from 5-10 mg total lipid per sample. Dried films were then resuspended using 1 ml HBS (pH=7.4). The lipid mixture was vortexed and heated at 45-50° C. for 15-20 minutes and subjected to at least five freeze-thaw cycles. The lipid suspensions were sonicated using a Probe sonicator (Branson Sonifier, Microtip probe, Fisher Scientific; 5-10 cycles, 1 minute per cycle followed by 1 minute of rest) in an ice bath.

HPPH-loaded vesicles were placed in microcentrifuge tubes and centrifugations were carried out at 6,000 rpm (~3000 RCF) for 30 minutes at 20-25° C. using a fixed-angle rotor centrifuge. Supernatants containing the vesicle-incorporated HPPH were collected, and any unincorporated HPPH, which aggregates in aqueous environment, was sedimented in the pellet fraction. A sample of an equivalent amount of free HPPH was suspended in HBS (without the lipids), and mixed by vortexing. The free HPPH aggregated in the buffer, which could be sedimented in the pelleted fraction upon centrifugation at low-speed as described above. This protocol presented a simple procedure to remove unincorporated HPPH from the vesicle-associated HPPH.

Characterization of Vesicles

Total Phospholipid Analysis: Phospholipid recovery in the vesicles was determined by analysis of inorganic phosphorus (Pi) according to Ames & Dubin. Typically, >90% lipids were recovered in various formulations.

Quantitation of Vesicle-associated HPPH: HPPH incorporation in the vesicles was determined by the measurement of absorbance. To quantitate initial input of HPPH in the samples, measurements were done in the sonicated samples before and after the centrifugation steps. Typically, 50 µl of the samples were placed in a 96-well plate and mixed with equal volumes of methanol and 1% TX100. The samples were mixed gently using a pipette and absorbance was measured at 665 nm using a micro plate reader (SpectraMax M2, Molecular Devices, Sunnyvale CA, USA).

Size Analysis of Vesicles: Size and population distribution of vesicles was determined by dynamic light scattering (DLS) measurements using a Malvern instrument (NANO ZS, Malvern Instruments, CA, USA). For a typical sizing experiment, 5-10 µl of vesicles were diluted in HBS to a final volume of 0.4 ml and the measurements were done using a microcuvette. Each run consisted of at least three measurements of 12 to 24 acquisitions per sample. HPPH-loaded vesicles were stored at room temperature and remained stable (no change in size analysis by DLS measurements) up to at least 60 days. The morphology of vesicles was further examined by cryo-electron microscope.

Light Treatments of Vesicles—The light treatments of the vesicles were done with two independent defined objectives. First, vesicles prepared without the HPPH were used to assess the effect of the PEGylated lipid on intermolecular packing of DC$_{8,9}$PC. This effect was monitored by 254 nm (UV)-induced DC$_{8,9}$PC photo-crosslinking Second, vesicles loaded with the HPPH were tested for the photoactivation of vesicle-associated HPPH. This effect was monitored using the 661 nm diode laser to assess the HPPH photodamage. HPPH loading in the vesicles was done in the absence of any UV treatments, and these vesicles were used for in vitro and in vivo tests in certain examples disclosed herein. Specifics of light treatment conditions are described below:

254 nm (UV) Treatment of Vesicles (Without HPPH): Vesicles prior to loading with HPPH were used for UV treatments (Table 1A). Vesicles (0.1 ml) were placed in 96-well clusters and were irradiated with a UV lamp (UVP, Short Wavelength Assembly 115V, 60 Hz, 254 nm) at a distance of 0.5 to 1 inch for various time periods (0-40 minutes) at room temperature. Appearance of cross-linked DC$_{8,9}$PC was monitored by measurements at 520 nm (3).

661 nm Laser Treatment of Vesicle$_{20}$-HPPH: Vesicle$_{20}$-HPPH (containing 50-100 µg lipid & 2.5-5 µg HPPH) were placed in a microcentrifuge tube and irradiated horizontally in a box fitted with a diode laser cube at room temperature. Irradiation was done for five minutes using the 661 nm laser (Coherent Cube Part Number 1130061) at a power output of 90 mW (125 mW/cm$^2$, as measured by the Thorlabs PM200 Energy Meter with the S121C Photodiode Power Sensor). Free HPPH dispersed in Tween 80 (Tween 80-HPPH) (4) and DPPC:DC$_{8,9}$PC:DSPEG2000 vesicles (Table 1B) were used as controls to compare the extents of photodamage.

Quantitation of Vesicles and Vesicle-Associated HPPH in Animal Tissues

DiR Quantitation in Tissues: For quantitation, a spectral profile of DiR (Ex/Em 750/780 nm) was taken to unmix the signal from the auto-fluorescence. The unmixed component image of the dye was used for quantitative analysis. A 2D region of interest (ROI) was drawn manually around the different organs to measure the total radiant efficiency within them. The background was measured in an area that did not evidence any uptake, typically around the neck area. The signal was normalized by the area of the ROI and the background was corrected. All the analyses were performed with the Maestro software version 2.10.0 (Perkin Elmer, Waltham, Mass.).

Quantitation of HPPH in Tissues: The multi-spectral imaging system IVIS Spectrum (Perkin-Elmer) along with Living Image (image acquisition and analysis software) was used to assay HPPH (Ex/Em 410/670 nm; Q-band Absorbance$_{max}$=665 nm). IVIS Spectrum has the capability to use either trans-illumination (from the bottom) or epi-illumination (from the top) to illuminate in vivo fluorescent sources. The instrument is equipped with 10 narrow band excitation filters (30 nm bandwidth) and 18 narrow band emission filters (20 nm bandwidth) that assist in significantly reducing autofluorescence by the spectral scanning of filters and the use of spectral unmixing algorithms. ROI are defined for areas of compound accumulation (tumor, liver, skin), and the total and average signal within the region are recorded. Fluorescent intensity is expressed as the total radiant efficiency ([p/s]/[µW/cm$^2$]). Results are expressed as mean total radiant efficiency of three mice±SD.

Serum Stability Assay—Vesicle$_{20}$-HPPH were incubated in 50% FBS for 2 hours at 37° C. To evaluate relative partitioning of HPPH between the vesicles and the serum proteins, the samples were loaded on a 20 ml Sepharose CL-6B column and eluted in HBS. Fractions (0.5 ml) were collected and analyzed for the presence of lipid, HPPH, and protein. Protein was determined through the Bradford assay (Biorad, Hercules CA) following manufacturers recommendations.

Cytotoxicity assays—Cellular toxicity by vesicle-formulated HPPH (upon light activation) was determined using the CT-26 cells. Briefly, cells plated in 96 well plates, were incubated with the samples at various concentrations at indicated times prior to light treatments. PDT treatments were done using the dye lasers (375; Spectra-Physics, Mt. View, CA) pumped by an argon-ion laser (either 171 or 2080; Spectra-Physics). Total light doses ranged from 1.0 to 4.0 $J/cm^2$ at a fluence rate of 3.4 $mW/cm^2$. After 48 hours post PDT treatment, cell viability was determined using the MTT assay (details are provided herein).

Animal Studies—Initially, athymic nu/nu mice were used for in vivo studies to establish relative enhancement of tumor uptake with the disclosed vesicles. Subsequently, immune-competent BALB/c mice were used to quantitate vesicle-associated HPPH and to determine in vivo PDT efficacy/tumor care of the formulated HPPH.

To evaluate the tumor uptake of various vesicles, DiR fluorescence in HT29 tumor-bearing athymic mice was monitored. Mouse imaging studies were performed following the Frederick National Laboratory for Cancer Research (Frederick, MD) Animal Care and Use Committee guidelines.

For quantitation of HPPH, PDT efficacy, and tumor regression, BALB/c mice bearing mouse colon carcinoma (CT-26) were used. These studies were done following the animal protocol approved by RPCI IACUC committee, described below. In additional examples, A549 tumor-bearing mice were used.

Tumor Implantation

HT29 Tumors: Six-week old athymic nu/nu mice, fed on AIN93G diet (Charles River Labs Inc.) were implanted with HT29 tumors for evaluation of DiR-based vesicle biodistribution. Tumor implantation of HT29 cells ($5 \times 10^6$ cells in 0.1 ml PBS per implant) was done subcutaneously in the lower flank of the animals.

CT-26 Tumors: CT-26 cancer cells were suspended at a density of $20 \times 10^6$/ml in serum-free media. 50 µl ($1 \times 10^6$ cells) were injected subcutaneously for tumor transplantation. Treatments were initiated 6-7 days later when tumor sizes reached approximately 4-5 mm in diameter or 32-62.5 $mm^3$ as measured by length×width×½ width.

A549 Tumors: A549 tumor cells were injected subcutaneously for tumor transplantation. Treatments were initiated when tumor sizes reached approximately 100 to 200 $mm^3$ as measured by length×width×½ width.

Tissue Uptake of Vesicles and Vesicle-Associated HPPH

Tumor Uptake of Vesicles in HT29 tumor bearing athymic mice: Vesicle$_{10}$-HPPH/DiR, Vesicle$_{20}$-HPPH/DiR and DPPC:DC$_{8,9}$PC—HPPH/DiR (Table 2) were intravenously injected (0.2 ml containing 1 mg total lipid) in groups of four animals. In addition, two animals were injected with only 0.2 ml HBS to obtain a background signal. Whole-body, 2D-multispectral fluorescence imaging (dorsal+ventral) was performed 4 hours after vesicle injection using the Maestro fluorescence imager (PerkinElmer, Waltham, Mass.) with the 735±25 nm excitation filter and 800 nm longpass LCTF (liquid crystal tunable filter) emission filter. Images were captured from 780-950 nm with a step size of 10 nm and an exposure time of 5 seconds for each wavelength. Details of quantitation of DiR in the tissues are provided herein.

Tissue Uptake of Vesicle-Associated HPPH in CT-26 tumor bearing BALB/c mice: The Vesicle$_{20}$-HPPH (Table 2) formulation was used for tissue uptake of vesicle-associated HPPH by CT-26 tumor bearing BALB/c mice. Tween 80-HPPH formulation (currently in clinical trials, Identifier: NCT01140178) was used for comparison. The formulations, diluted with 5% dextrose solution in water to achieve a dose of 0.47 µmot HPPH/kg body weight, were injected intravenously (0.2 ml). Near-infrared optical imaging was performed at various time periods post-injections. Detailed procedure for quantitation of tissue-associated HPPH is described herein.

Tissue Uptake of Vesicle Embodiments in A549 tumor bearing mice: Vesicles comprising DC$_{8,9}$PC: DSPE-PEG2000 (90:10 mole ratio) were used. 0.1 ml of the formulation containing 1 mg lipid content & trace amounts of DiR was injected intravenously. Imaging was performed at various time periods post-injections.

In Vivo PDT Efficacy and Tumor Regression in CT-26 Tumor Bearing BALB/c Mice:

The Vesicle$_{20}$-HPPH (Table 2) and Tween 80-HPPH, injected in BALB/c mice bearing CT-26 tumors (section 2.5.2ii), were investigated for long-term PDT efficacy (tumor cure). Based on tumor uptake of HPPH (FIGS. 9A-9C), laser treatments were done at 4 hour and 24 hours post injections for Vesicle$_{20}$-HPPH and Tween-80-HPPH, respectively. Mice restrained in acrylic holders were treated with 665 nm laser (375; Spectra-Physics, Mt. View, Calif.) pumped by an argon-ion laser (either 171 or 2080; Spectra-Physics), tuned to 665 nm. The power output from the fiber was 71 mW in a 1.1 cm spot. Total light dose was 135 $J/cm^2$ for a period of 30 minutes, giving a fluence rate of 75 $mW/cm^2$.

Tumor re-growth was monitored up to 100 days post PDT treatment. Tumors which re-grew after treatment were calibrated every other day and tumor volume was recorded as length×width×½ width=volume. When the tumors reached ≥400 $mm^3$, mice were euthanized and the time of tumor re-growth to 400 $mm^3$ was calculated. The tumor responses that were characterized as partial response (PR) indicated a tumor growth inhibition of at least 50% compared with untreated controls. Complete response (CR) was defined as the inability to detect tumor by palpation at the initial site of tumor appearance for up to 100 days post therapy and were considered cures. Tumor regrowth after CR occurrence was observed in less than 5% of mice. Normally, 5 mice per treatment group were included in the experiments.

Example 1

Figure 24A:
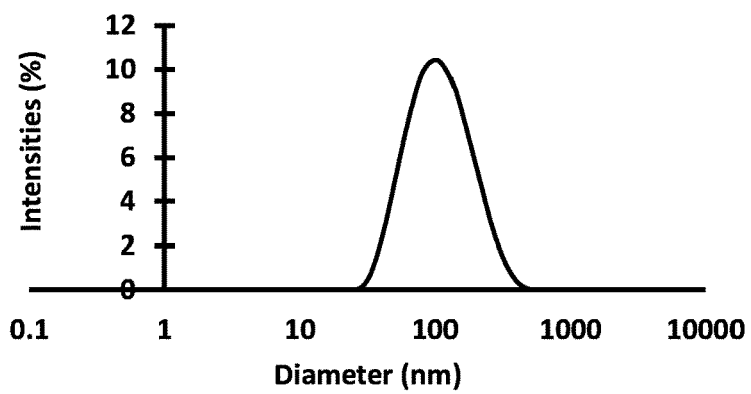
FIGS. 24A-24C provide results obtained from analyzing vesicle embodiments comprising DSPE-PEG2000 and $DC_{8,9}PC$ and Ce6.
Figure 24B:
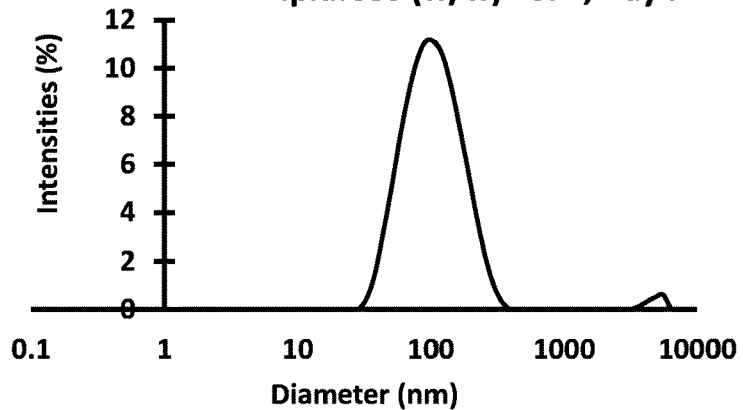
Figure 24C:
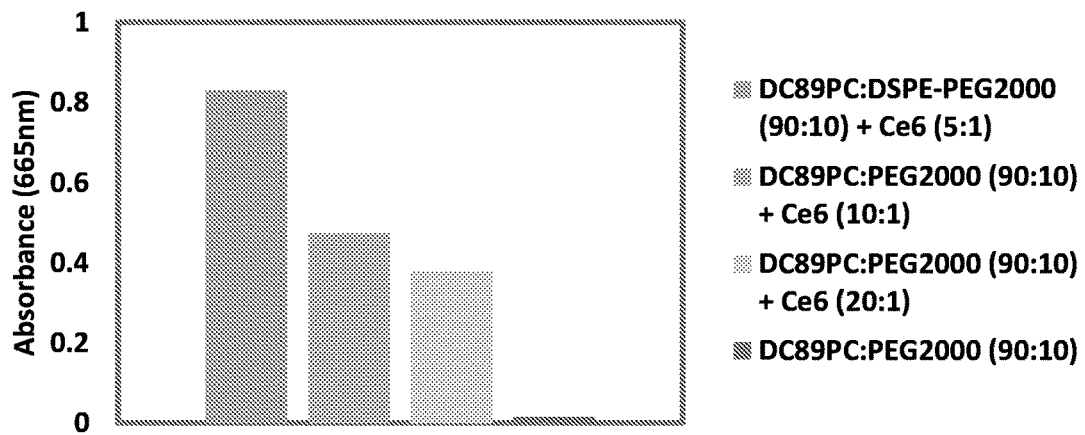

DC$_{8,9}$PC alone assumes tubule-like morphology in aqueous dispersions, not a preferred nanostructure for intended drug delivery applications. It was determined that a lipid molecule with large hydrophilic surface (such as a PEGylated lipid) could associate with DC$_{8,9}$PC and induce a vesicular morphology (FIG. 1). The effect of varying concentrations of DSPE-PEG2000 on the ability of DC$_{8,9}$PC to transition to vesicles prior to incorporation of HPPH was evaluated (Table 1). The vesicle formation was monitored by hydrodynamic size determination of sonicated samples (FIGS. 10A-10F) and visualization by cryo-electron microscopy (FIGS. 11A and 11B). Additional results of hydrodynamic size determination are provided by FIGS. 19A-19H. Also, results of hydrodynamic size determination for vesicles comprising Ce6 are provided by FIGS. 24A-24C. As can be seen by FIG. 24C vesicle embodiments are able to load Ce6 and they exhibit good stability as evidenced by FIGS. 24A and 24B. Details regarding the evaluated formulations are provided in Table 6 herein.

Figure 4:
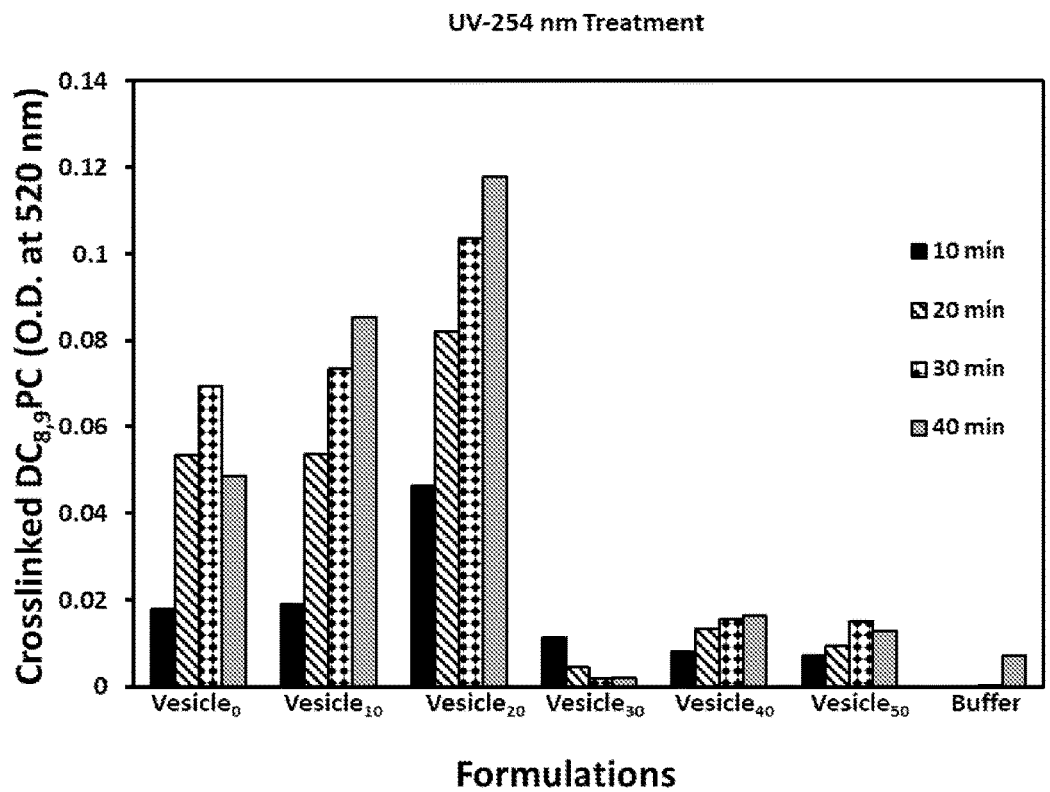
FIG. 4 is a bar graph showing the effect on UV-triggered photocrosslinking of $DC_{8,9}PC$ by including DSPE-PEG2000 in lipid formulations wherein various vesicle embodiments (see Table 1) were placed in a 96-well plate and exposed to UV light (254 nm) for the indicated time periods at room temperature and at the end of each incubation, absorbance was measured at 520 nm to assess photocrosslinking.

In some embodiments, the data demonstrate that inclusion of the PEG-lipid ranging at 10 to 20 mol % (Vesicle$_{10}$ and Vesicle$_{20}$) resulted in the formation of homogeneous vesicles with 65-100 nm hydrodynamic diameter (FIGS. 10B and 10C, respectively) with a polydispersity index (PdI) ranging between 0.2-0.3. As expected, DC$_{8,9}$PC in the absence of PEG-lipid was poly-disperse (see Vesicle$_0$ data in Table 1 and FIG. 10A). PEG-lipid concentrations beyond 20 mol % (Vesicle$_{30}$, Vesicle$_{40}$ and Vesicle$_{50}$) resulted in heterogeneous multiple peaks (average diameter 70-370 nm, FIGS. 10D-10F) with a very high PdI (0.4-0.5). The effect of varying concentrations of DSPE-PEG2000 on intermolecular packing of DC$_{8,9}$PC in the binary lipid bilayer was also examined by quantifying UV-mediated photo-cross-linking (FIG. 4).

Example 2

After optimizing the desired PEG-lipid to DC$_{8,9}$PC ratios required for vesicles formation, the Vesicle$_{10}$ and Vesicle$_{20}$ were tested for their ability to incorporate HPPH (designated as Vesicle$_{10}$-HPPH or Vesicle$_{20}$-HPPH).

Various concentrations of HPPH ranging from the 0.05 to 0.5 mg/mg lipid and were added to the lipid mixture and HPPH-loaded vesicles were prepared. A dose-response curve for efficiency of HPPH incorporation in Vesicle$_{20}$ is shown, for example, in FIGS. 7A and 7B. An impressive dose of HPPH (up to 0.5 mg HPPH/mg lipid) could be included in these vesicles (FIGS. 7A and 7B). To separate unincorporated HPPH from vesicle-entrapped HPPH, we used a simple and novel low speed centrifugation protocol. HPPH in the absence of lipids, when dispersed in aqueous medium, aggregates and can be sedimented as pelleted fraction by low-speed centrifugation. Technical details of the purification procedure used for HPPH-loaded vesicles are provided described herein (also see FIG. 6).

Vesicle$_{20}$-HPPH loaded at 0.05 mg HPPH/mg lipid were further investigated by cryo-EM, serum stability, PDT effects on cellular toxicity, tumor uptake, and tumor regression studies.

Example 3

The Vesicle$_{20}$-HPPH vesicles (loaded with 0.05 mg HPPH/mg lipid) exhibited spherical morphology as visualized by cryo-EM. Inclusion of HPPH in the Vesicle$_{20}$ had no apparent effects on the overall morphology or size of these vesicles (FIGS. 11A and 11B). DLS analysis further confirmed that the average size of Vesicle$_{20}$ and Vesicle$_{20}$-HPPH were similar (68 nm and 78 nm, respectively) (FIGS. 12A and 12B). Without being limited to a single theory of operation, it currently is believed that the slight increase in the average size of the Vesicle$_{20}$-HPPH vesicles is due to the inclusion of HPPH in the vesicles.

To evaluate the stability of these vesicles upon storage, DLS analysis was performed periodically up to at least 60 days. The data, presented in FIGS. 12A and 12B, show results up to 42 days. These vesicles retain their original size distribution during the time tested. This property is likely to be advantageous for future in vivo applications.

Example 4

In vivo utility of lipid-based vesicles is often limited due to their interactions with plasma components that result in untimely and off-target release of encapsulated drugs. Since the disclosed vesicles have significantly higher amounts of PEG-lipids, the vesicles can be stable in the presence of serum proteins. The stability of Vesicle$_{20}$-HPPH (loaded with 0.1 mg HPPH/mg lipid) in the presence of serum at 37° C. for 2 hours was evaluated. The possible exchange of HPPH from the vesicles to serum proteins was determined by fractionation on a size-exclusion column with fractionation range of $1\times10^4$-$4\times10^6$ molecular weight (Sepharose CL6B, Methods section). This method has been previously demonstrated to separate vesicles from the serum as well as plasma proteins of vesicle-injected animals. Column fractions were analyzed for lipid, protein, and HPPH (FIG. 13). As expected the vesicles eluted in fractions 12-15, and major serum proteins (such as albumin) were eluted in later fractions (after fraction 20) as determined by the protein assay. HPPH analysis revealed that most of the detectable HPPH remained associated with the vesicles and the lipid/HPPH ratio remained unaffected in the vesicle fractions, demonstrating that the HPPH did not exchange at least with the bulk serum proteins.

Example 5

To determine the PDT efficacy of HPPH in these formulations, their cytotoxicity upon laser treatment in CT-26 cells was evaluated. The cells were incubated with Vesicle$_{20}$-HPPH at various HPPH doses ranging from 0 to 1 μM for 4 or 24 hours at 37° C. (FIGS. 14A and 14B, respectively). Subsequently, the cells were treated with the laser and cell viability was determined at 48 hours post treatment. As expected, cytotoxicity was observed only upon laser treatment (FIGS. 14A and 14B). The in vitro cytotoxicity data at 4 hours and 24 hours incubations indicate that the Vesicle$_{20}$-HPPH is slightly more effective at the longer incubation time. IC$_{50}$ at 4.0 Joules/cm$^2$ is ~0.03 micromolar at 4 hours and ~0.01 micromolar at 24 hours (FIG. 14B).

Example 6

To monitor the potential benefits of high PEG-lipids in these formulations on tumor accumulation, a near IR lipid probe, DiR, was incorporated in the vesicles. DiR is a widely used molecule for mouse imaging studies due to its absorbance in the near-IR region (Ex/Em 745/845 nm). Vesicle$_{10}$-HPPH/DiR and Vesicle$_{20}$-HPPH/DiR (Table 2) were examined and compared with a formulation containing 4 mol % DSPE-PEG2000. Intravenously-injected mice were imaged at 4 hours post injections and data were analyzed (see FIG. 15). FIG. 15 shows relative uptake of vesicles containing either 4, 10, or 20 mol % PEG-lipid. Tumor accumulation of vesicles is clearly enhanced as a function of increase in PEG-lipid content, confirming that higher PEG-lipid in the vesicles favors tumor accumulation, consistent with our hypothesis. Quantitation of DiR fluorescence showed a 2.2 and 2.6-fold increase in Vesicle$_{10}$ and Vesicle$_{20}$, respectively (see FIG. 16A). The ratios of an average of DiR fluorescence in tumor/liver (T/L) were determined and the data are presented in FIG. 16B. The T/L ratios obtained for DPPC:DC$_{8,9}$PC:DSPE-PEG2000 (86:10:04 mole ratio) were taken as 100 for comparison. An increase in tumor/liver ratios was seen in Vesicle$_{10}$ and Vesicle$_{20}$-injected animals in comparison to vesicles containing 4 mol % PEG-lipid, consistent with enhanced tumor accumulation of vesicles as shown in FIG. 16A. Once it was established that enhanced PEGylation resulted in increased NPs accumulation in the tumors, Vesicle$_{20}$ (containing 20 mol % PEGylated lipid) was used for therapeutic efficacy studies; in these examples HPPH was measured to monitor relative accumulation in various organs including tumors (next section below).

Example 7

Figure 9A:
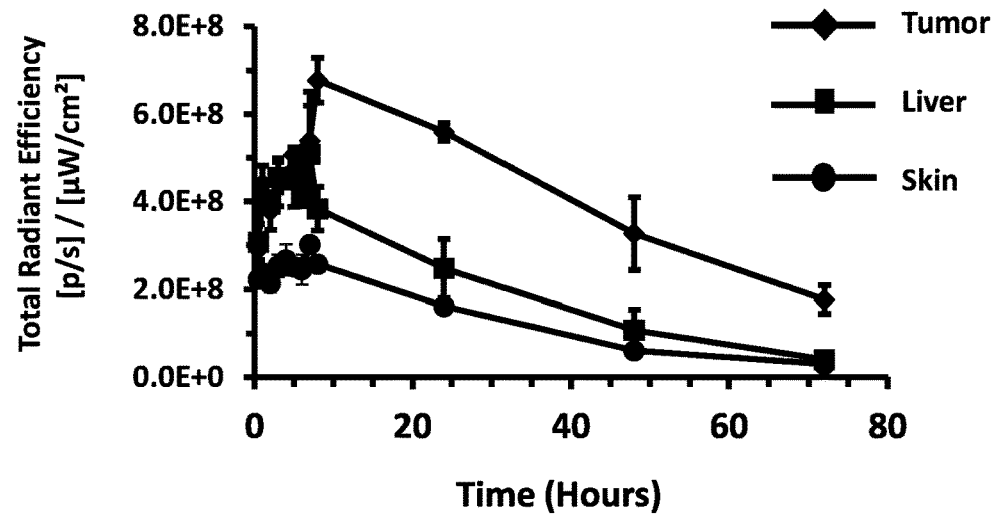
FIGS. 9A-9C show optical imaging results obtained from analyzing the in vivo tissue distribution of vesicle-formulated HPPH in the liver, tumor, and skin of tumor-bearing mice; CT-26 tumor-bearing BALB/c mice were intravenously injected (groups of five) using either Tween 80-HPPH (FIG. 9B) or Vesicle$_{20}$-HPPH (FIG. 9A); a Vesicle$_{20}$ formulation without HPPH (FIG. 9C) was used to obtain background signals and images were collected at various time intervals and average radiant efficiency of HPPH in tumor, liver and skin was determined.
Figure 9B:
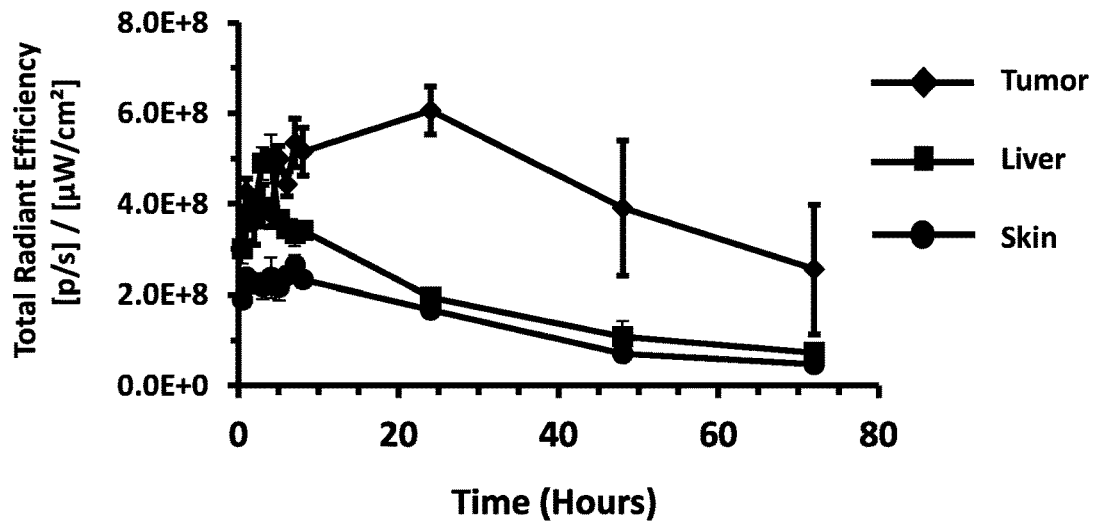
Figure 9C:
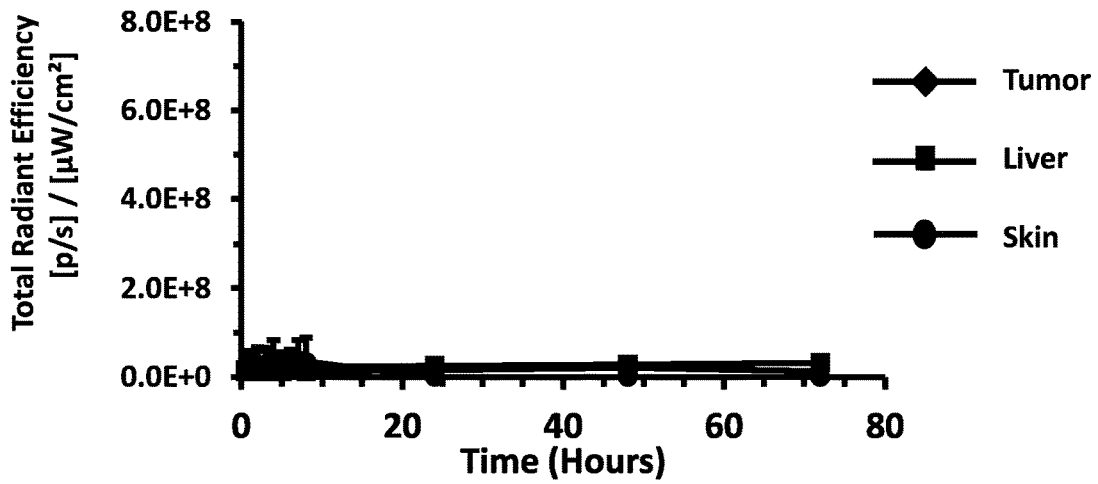

After establishing the tumor uptake of Vesicle$_{20}$-HPPH by DiR imaging, our next experiments were designed to quantitate time-dependent tissue distribution in CT-26 tumor bearing mice. The results were compared with Tween 80-HPPH formulation. BALB/c mice bearing CT-26 tumors were intravenously injected with Vesicle$_{20}$-HPPH or Tween 80-HPPH at equivalent HPPH doses. The animals were imaged for HPPH fluorescence in the tumor, liver and skin at various time intervals post injections (FIGS. 9A-9C). Interestingly, Vesicle$_{20}$-HPPH showed faster kinetics of accumulation with maximal accumulation at 8 hours post injection (FIG. 9A). On the other hand, the Tween 80-HPPH formulation peaked at 24 hours (FIG. 9B). Faster kinetics of tumor uptake by Vesicle$_{20}$-formulation is likely due to its nanoparticulate assembly/EPR effect. Relative distribution of HPPH in the liver and skin was found to be similar (FIGS. 9A-9C). Vesicle$_{20}$ without HPPH containing equivalent lipid doses were used to obtain background fluorescence. (FIG. 9C). No fluorescence above background levels was detected in these animals confirming that the fluorescence observed in Vesicle$_{20}$-HPPH-injected mice indeed was due to the presence of HPPH in various organs.

Example 8

Accumulation of HPPH in tumors occurred with relatively similar efficiency by animals injected with either Tween 80-HPPH or Vesicle$_{20}$-HPPH (preceding section). However, interestingly, the maximal uptake of Vesicle$_{20}$-HPPH occurred at earlier time points as compared to Tween 80-HPPH. Therefore, the PDT efficacy for Vesicle$_{20}$-HPPH at 4 hours post injection and 24 hours post injection for Tween 80-HPPH was evaluated.

Figure 17A:
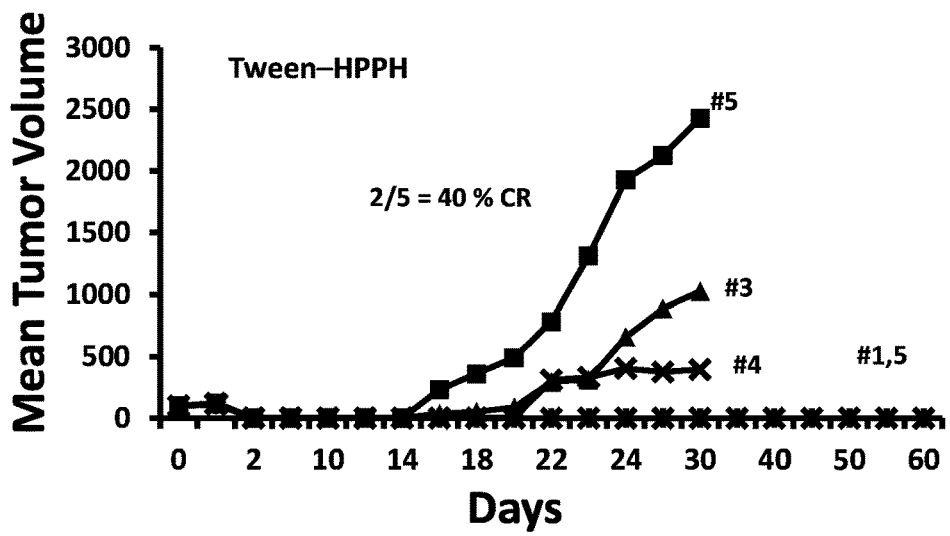
FIGS. 17A-17C show results obtained from analyzing in vivo PDT response and antitumor activity of a vesicle embodiment described herein, Vesicle$_{20}$-HPPH, in CT-26 bearing BALB/c mice; to generate these results, a comparison example, Tween 80-HPPH (FIG. 17A) and an exemplary vesicle embodiment, Vesicle$_{20}$-HPPH (FIGS. 17B and 17C), were intravenously injected in tumor-bearing mice at 0.47 μmot HPPH/kg body weight; laser treatments were done post 4 hours for Vesicle$_{20}$-HPPH-injected animals and post 24 hours injections of Tween 80-HPPH and tumor volumes were measured at indicated days.
Figure 17B:
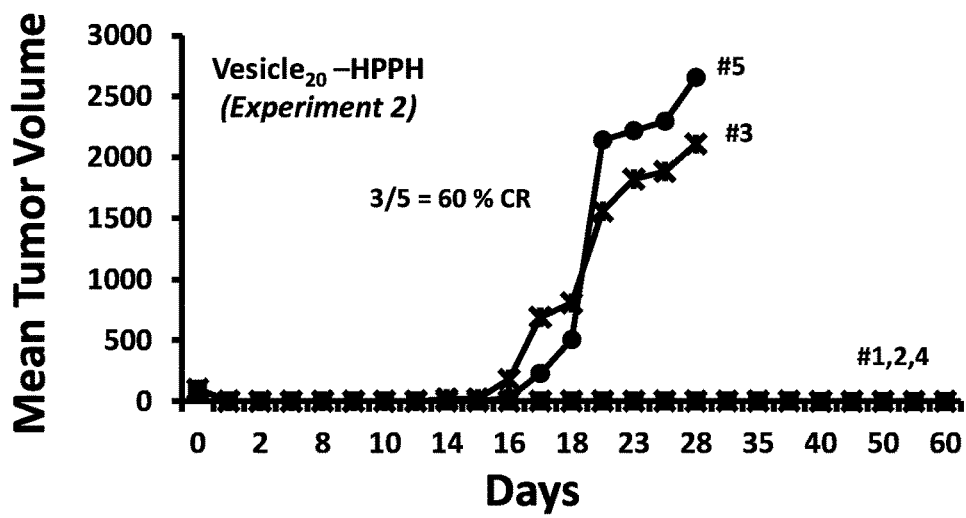
Figure 17C:
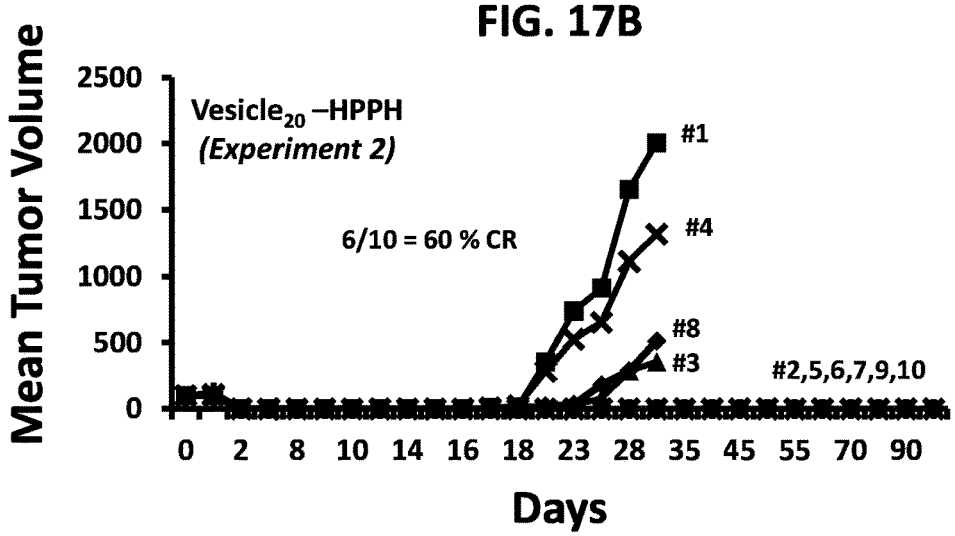

PDT efficacy was evaluated by exposure of tumors to a laser light (665 nm) at a dose of 135 J/cm$^2$ and 75 mW/cm$^2$ for 30 minutes. Subsequently, tumor growth was measured daily up to 100 days post treatment. The effect of the PDT on the tumor surface was evinced by the lack of scabbing as compared to HPPH alone which showed scabbing post PDT treatment (FIGS. 17A-17C). In our first set of experiments, tumor regression in an intravenously injected group of five mice with either Tween 80-HPPH (FIG. 17A) or Vesicle$_{20}$-HPPH (FIG. 17B) was tested. The Vesicle$_{20}$-HPPH-injected mice exhibited excellent animal survival (CR=60%) and tumor response in comparison to Tween 80-HPPH injected animals (CR=40%). These results indicated a clear advantage of vesicle-formulated HPPH for cancer chemotherapy.

Figure 18:
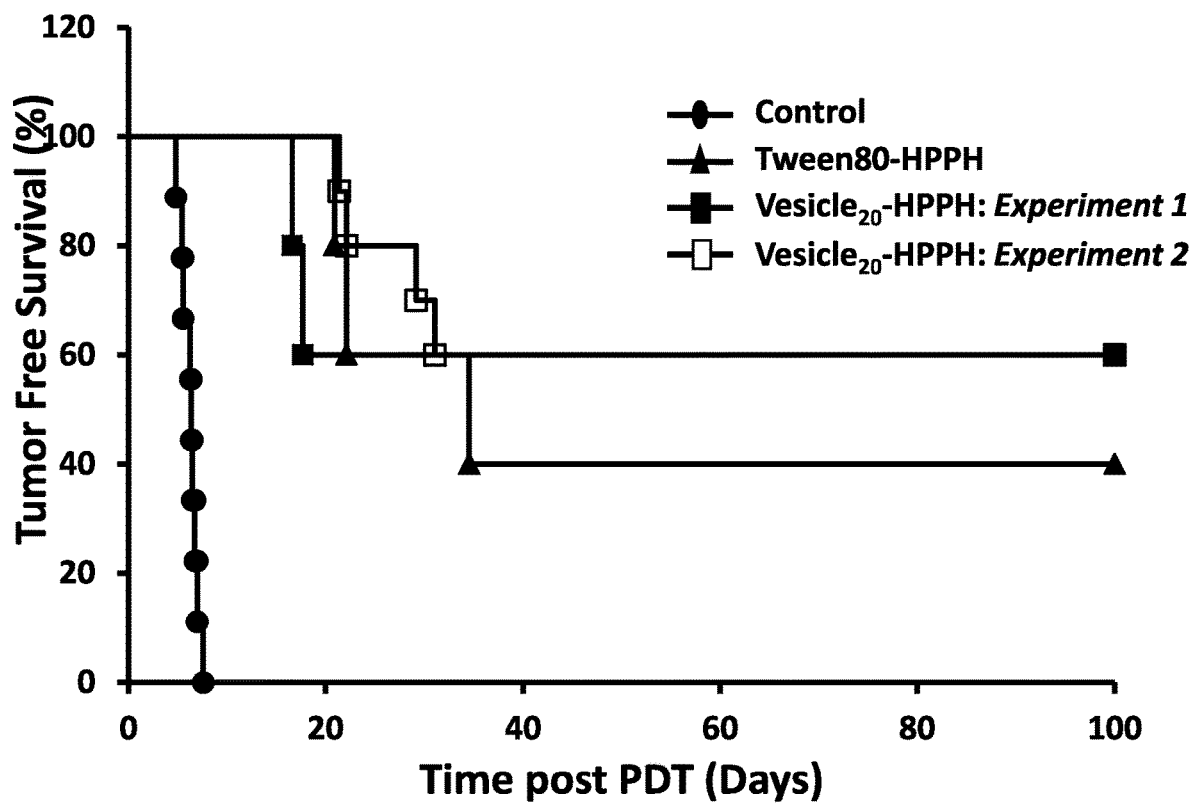
FIG. 18 is a Kaplan Meier graph comparing animal survival data obtained for Vesicle$_{20}$-HPPH (two independent experiments) and Tween 80-HPPH.

To further validate the observed enhanced anti-cancer activity by the Vesicle$_{20}$-HPPH, a second set of animal study was designed (ten animals). Vesicle$_{20}$-HPPH were injected in tumor-bearing mice under identical conditions, treated with the laser, and tumor cure was monitored up to 100 days. The combined results for individual tumor responses by the animals are presented in FIG. 17C. Excellent tumor response was observed, and 9/15 mice (CR=60%) were found to be tumor-free up to 100 days (FIG. 17C). The Kaplan Meier graph showed the statistically significant (a P value of <0.0001) response with tumor-free survival with Vesicle$_{20}$-HPPH (FIG. 18). Therefore, vesicle-formulated HPPH presents a new and efficient nano-delivery platform for this drug. The vesicle embodiments described herein can be used with other PDT drugs, particularly those bearing similar chemical and physical properties to HPPH.

Example 9

To understand the nature of DC$_{8,9}$PC/PEG-lipid nano-assemblies, sonicated samples were treated with UV (254 nm) at room temperature for various time periods (Methods section, supplemental). UV treatments were done in the vesicles that did not include HPPH with the sole purpose of assessing any potential interference in DC$_{8,9}$PC packing properties by the PEGylated lipid. The extent of photo-crosslinking was monitored by a shift in chromogenic properties of the samples (appearance of spectral peaks at 520 nm) as a function of exposure time as indicated. Results are shown in FIG. 4 and are representative of at least two independent experiments. Formulations containing 10 & 20 mol % PEG-lipid (Vesicle$_{10}$ & Vesicle$_{20}$, Table 1) had no effect on DC$_{8,9}$PC packing properties as demonstrated by a time-dependent increase in absorbance at 520 nm. Control samples (Vesicle$_0$, without the PEG-lipid) showed similar photo-crosslinking. On the other hand, in some embodiments, concentrations greater than 20 mol % of the PEG-lipids (Vesicle$_{30}$, Vesicle$_{40}$ and Vesicle$_{50}$, Table 1) interfered with photo-crosslinking indicating that the DC$_{8,9}$PC monomer alignment was disrupted at concentrations of the PEG-lipid that exceed 20 mole % (FIG. 4). It was also determined that the extents of photo-crosslinking in Vesicle$_{10}$ and Vesicle$_{20}$ were increased as compared to that of Vesicle$_0$ at a given time point (FIG. 4). This data confirms that PEG-lipids, at desired mole ratios, assist in enhanced sequestering and alignment of DC$_{8,9}$PC in vesicles as segregated patches in the binary lipid bilayer.

Example 10

Figure 8:
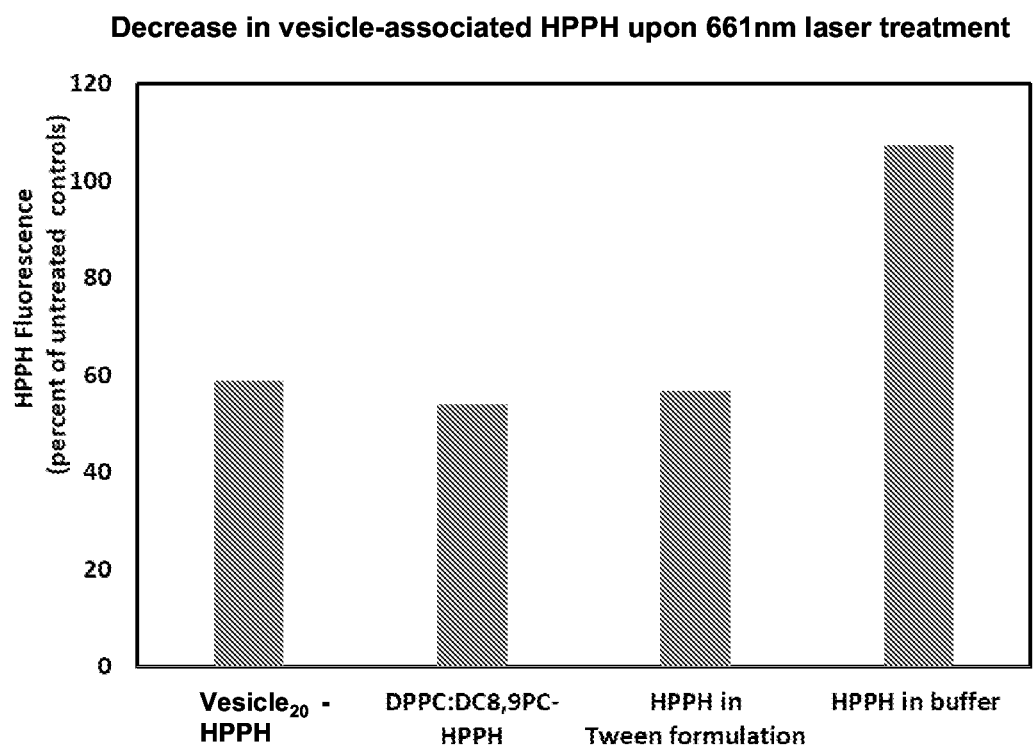
FIG. 8 shows results obtained from analyzing HPPH incorporation in a vesicle embodiment disclosed herein and further illustrates that HPPH's PDT efficiency is not impaired when incorporated in the vesicle's binary lipid bilayer; to generate these results, vesicle-formulated HPPH embodiments and equivalent amounts of HPPH suspended in buffer were treated with a 661 nm laser for five minutes and the fluorescence of HPPH remaining after the laser treatments were assessed, taking the fluorescence of untreated samples as 100%.

The efficiency of photoactivation by HPPH upon laser exposure depends on its environment and aggregation state. Laser treatment of HPPH results in photodamage and serves as an indication of its activity. Therefore, the photodamage of vesicle-formulated HPPH was compared with Tween 80-HPPH and a formulation comprising DPPC and a lower concentration of DSPE-PEG2000 (see Table 2). The extent of photodamage was tested using Vesicle$_{10}$-HPPH containing 1:0.05 Lipid:HPPH ratios (Table 2) upon treatment with 661 nm laser for five minutes. Data in FIG. 8 shows HPPH fluorescence remaining in laser-treated samples, taking 100% as fluorescence of untreated samples. As can be seen in FIG. 8, the extent of photodamage for Vesicle$_{20}$ was similar to the DPPC-containing formulation or Tween 80-HPPH. Laser exposure of HPPH suspended in the buffer did not result in a decrease in fluorescence upon laser treatment under identical conditions due to its insolubility and presumably its aggregated state. The results presented in FIGS. 7A and 7B demonstrate that vesicle-associated HPPH retains its photoactivation potential.

Example 11

Figure 5:
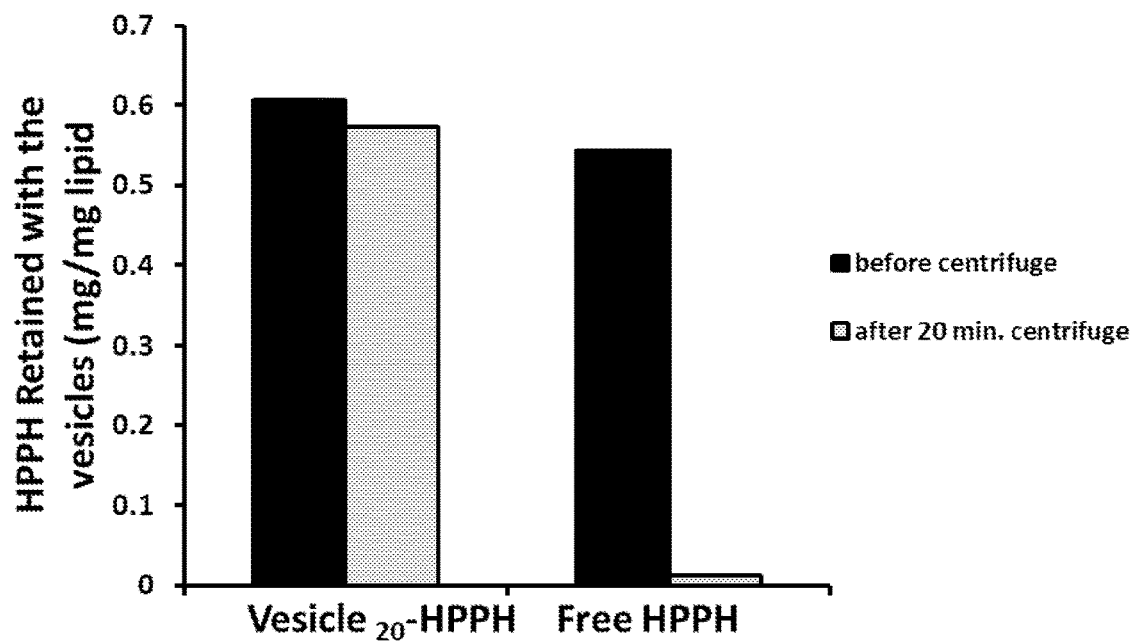
FIG. 5 shows results obtained from using a centrifugation technique disclosed herein to remove unincorporated HPPH from HPPH-embedded vesicles, wherein HPPH-loaded vesicles were placed in microcentrifuge tubes and centrifugations were carried out at 6,000 rpm (~3000 RCF) for 30 minutes at 20-25° C. using a fixed-angle rotor centrifuge, supernatants containing the vesicle-incorporated HPPH were collected, and any unincorporated HPPH was sedimented in the pellet fraction.

Free, unincorporated HPPH aggregates in aqueous buffer due to its insolubility, and can be pelleted upon sedimentation by low-speed centrifugation. Size exclusion chromatography (PD10 columns, GE Scientific) was used to separate unincorporated HPPH from the vesicles; however, in these embodiments, it was observed that sonication of HPPH dispersion in the HBS (in the absence of lipids) generated smaller HPPH aggregates that coeluted (in part)

with vesicle-associated HPPH on the PD10 column. This interfered with separation of liposomal HPPH from the unincorporated HPPH. Therefore, a new, simple centrifugation method was developed to separate unincorporated HPPH from vesicle-associated HPPH. The data using Vesicle$_{20}$-HPPH loaded with the highest concentration of HPPH (0.5 mg HPPH/mg lipid) are shown in FIG. 5. Centrifugation of HPPH-loaded vesicles at 6,000 rpm for 20-30 minutes resulted in effective separation of unincorporated HPPH from the vesicle-associated HPPH (FIG. 6). The HPPH suspended in HBS (in the absence of lipids) remained in suspension prior to centrifugation as determined by absorbance measurements. The centrifugation step resulted in nearly complete sedimentation of the HPPH into the pelleted fraction (FIG. 6). In contrast, when HPPH-loaded vesicles were centrifuged under identical conditions, only a very small fraction of HPPH was pelleted (FIG. 5). Therefore, this centrifugation protocol provides a simple and efficient method to remove any unincorporated HPPH from the vesicle-associated HPPH.

Example 12

Figure 20A:
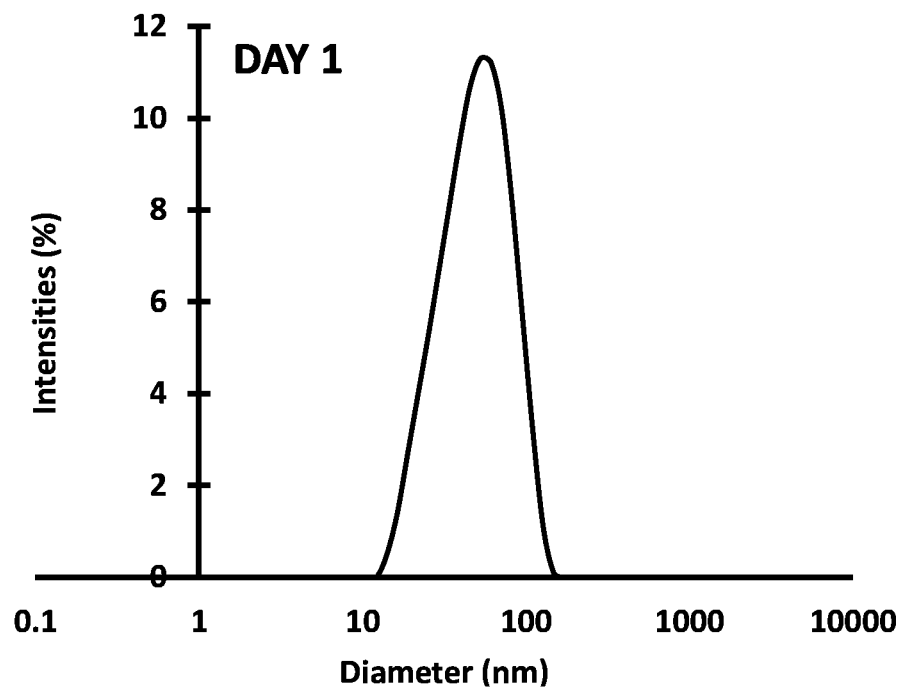
FIGS. 20A and 20B are graphs of intensity (%) as a function of diameter (nm), showing the average diameter and polydispersity index of certain vesicle embodiments comprising camptothecin embedded in the bilayer after 1 day (FIG. 20A) and after 7 days (FIG. 20B).
Figure 20B:
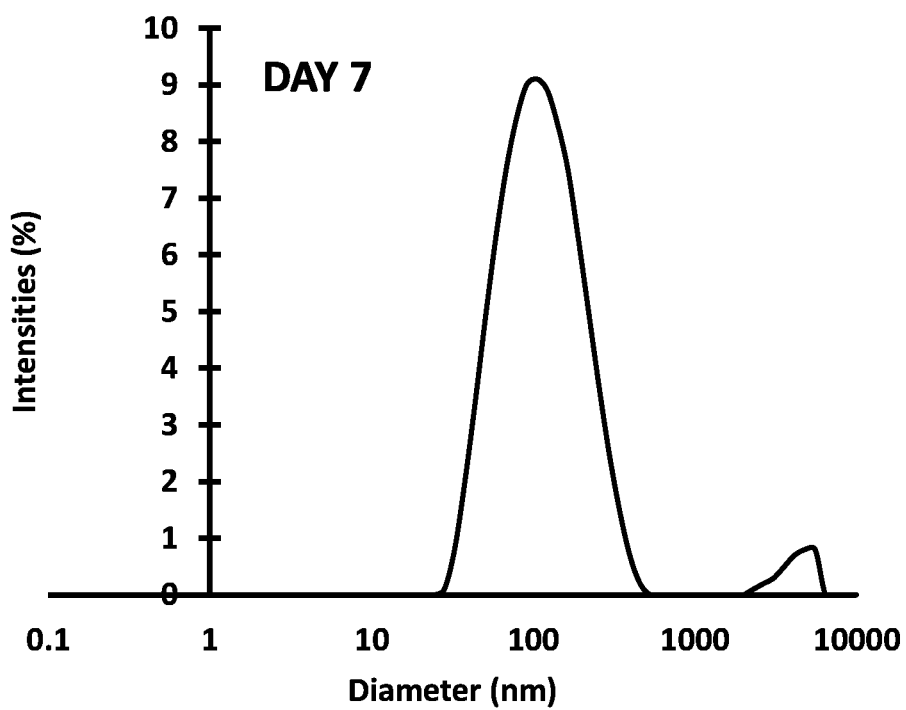
Figure 21A:
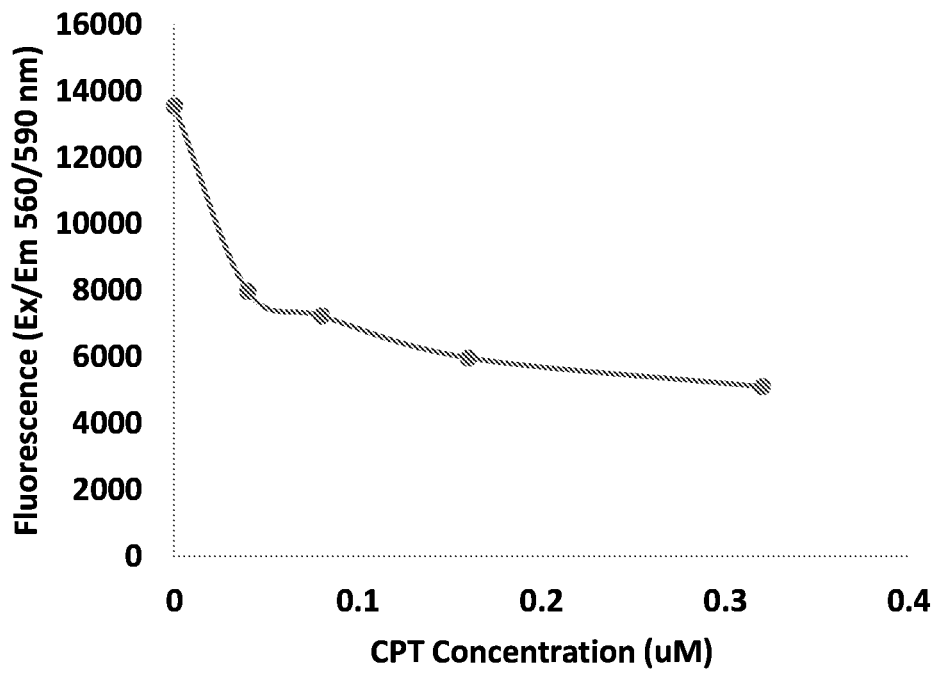
FIGS. 21A and 21B are graphs of fluorescence as a function of camptothecin concentration (uM) showing results from analyzing camptothecin-induced cytotoxicity in human breast cancer cells of camptothecin-formulated vesicles (FIG. 21A) as compared to a free camptothecin dose (FIG. 21B).
Figure 21B:
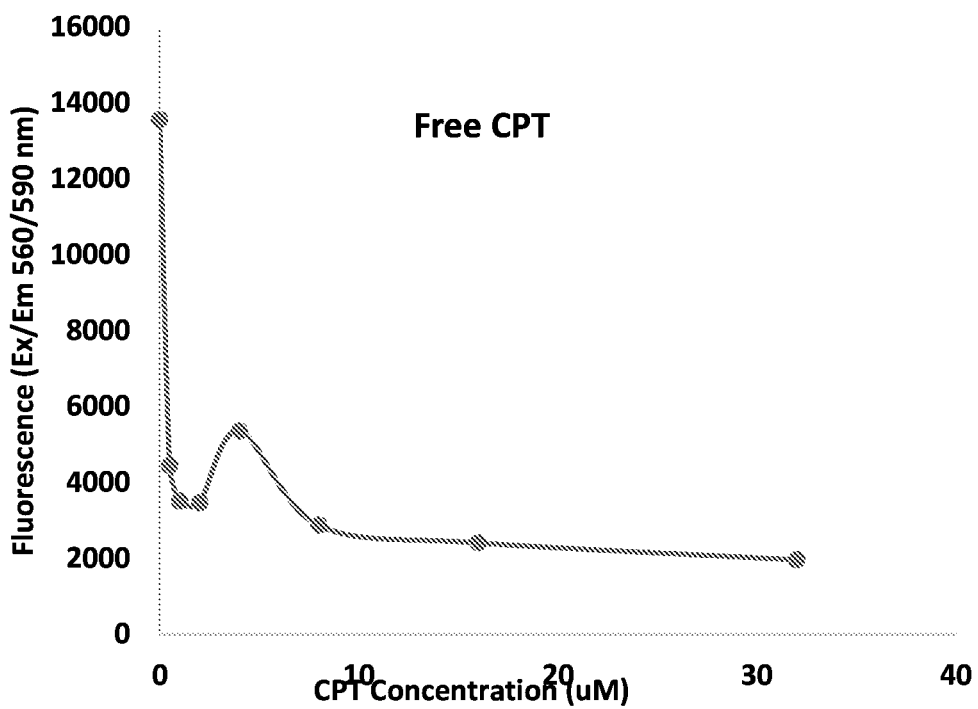

In this example, vesicle embodiments comprising camptothecin were made and evaluated. Vesicle formation and polydispersity was evaluated using dynamic light scattering (FIGS. 20A and 20B). The vesicles were made using a method similar to that disclosed above for the HPPH-containing embodiments. Vesicles were made to include a 90:10 ratio of DC$_{8,9}$PC to DSPE-PEG2000 and were loaded with camptothecin at a weight/weight ratio of 20:1 lipid:camptothecin. MDA-MB-231 (human breast cancer) cells were plated on 96-well clusters at a density of 5×103 per well for cell viability assay. The camptothecin-loaded vesicles or the free camptothecin were diluted to desired concentrations in the cell culture medium. 0.1 ml of the diluted samples were added per well in triplicate, and incubations were continued for 72 hours at 37° C. Cell viability was determined using the Cell Titer Blue Assay Kit (Promega corp. Madison, WI). Results are provided by FIG. 21A (results for camptothecin-formulated vesicles) and 21B (results for free camptothecin).

Example 13

Figure 22A:
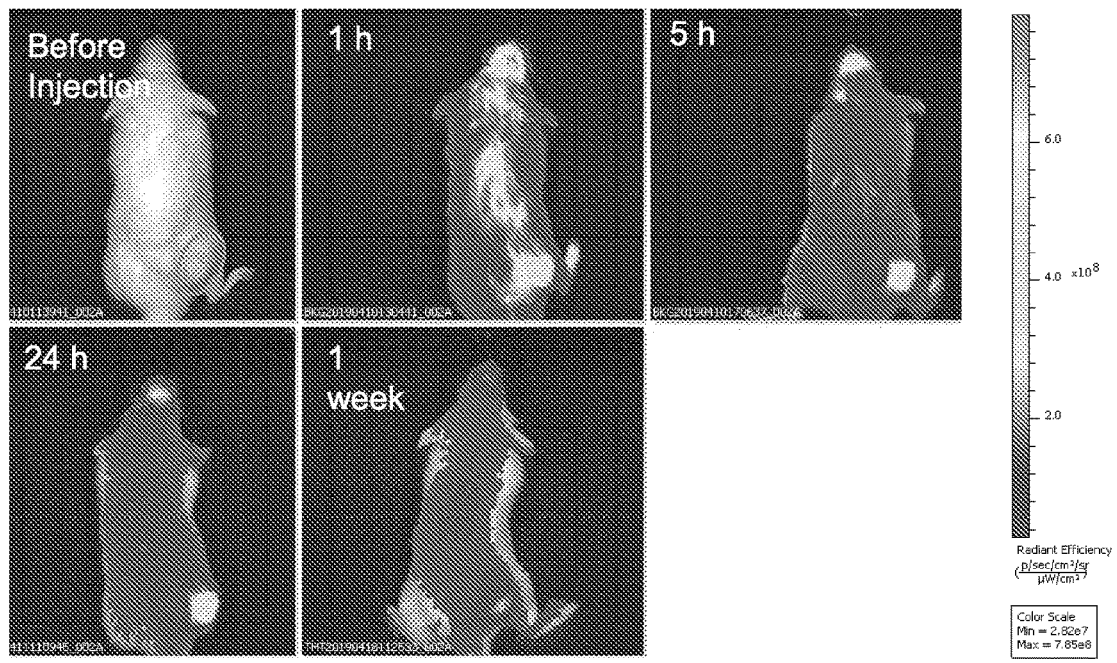
FIGS. 22A and 22B provides in vivo images of two different A549 tumor-bearing mice that were implanted with A549 cells subcutaneously and then injected with vesicle embodiments comprising a binary lipid bilayer without a cytotoxic agent and trace amounts of DiR; these figures show that disclosed vesicle embodiments are able to accumulate in tumors and do not exhibit long-term liver toxicity; to generate the results, mice were injected with A549 cells and upon tumors reaching 100 mm$^3$ to 200 mm$^3$, 0.1 ml of the vesicles (containing 1 mg total lipid) were injected intravenously and DiR imaging was performed.
Figure 22B:
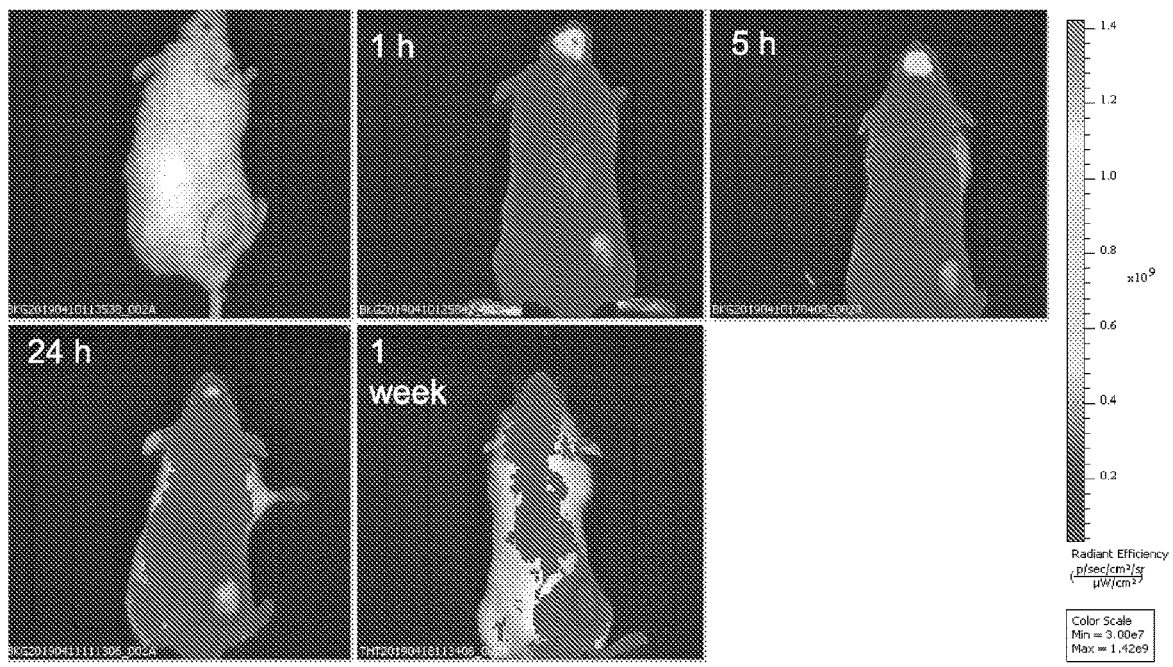
Figure 23:
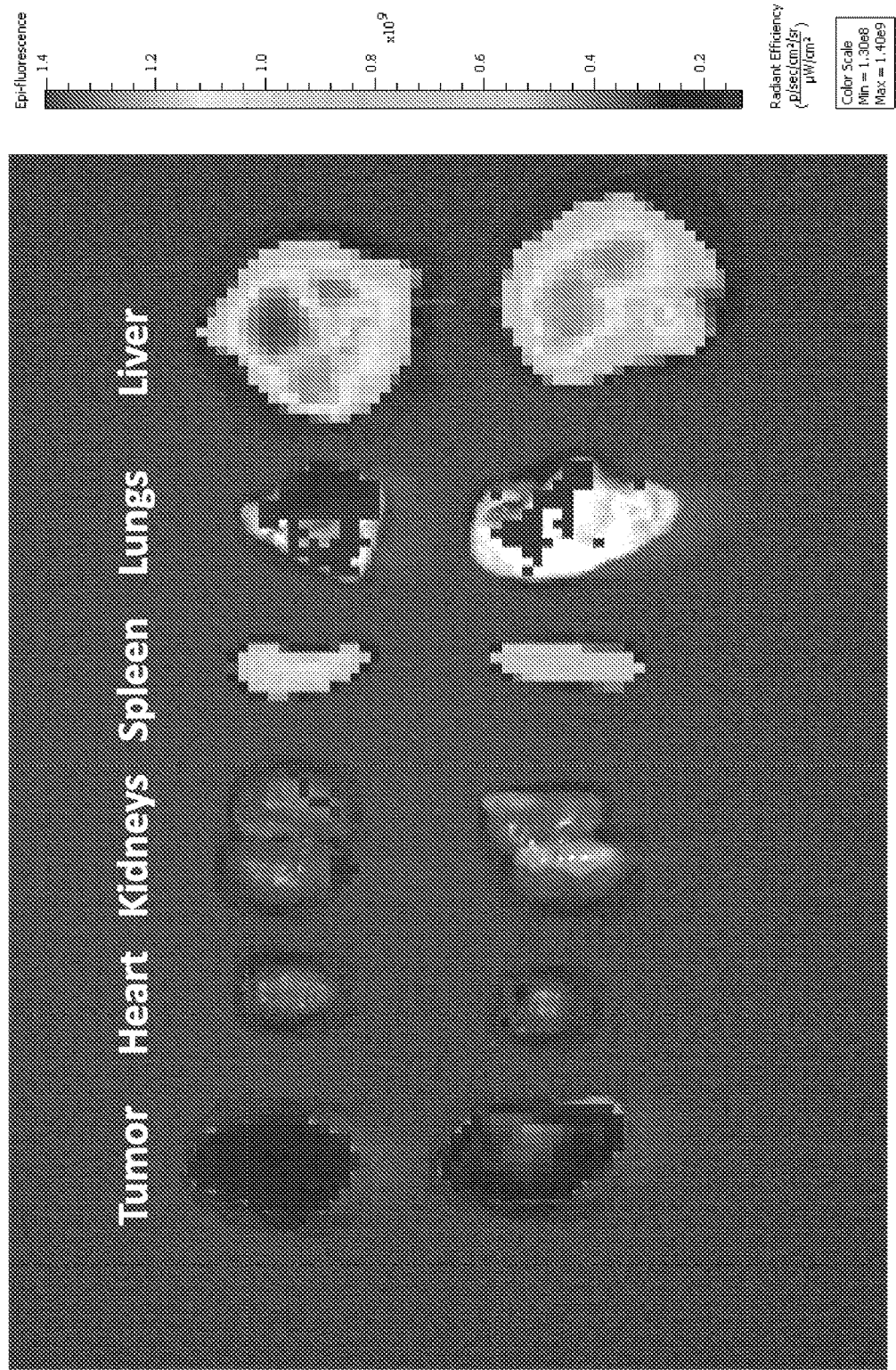
FIG. 23 provides images of various tissues of the mice illustrated in FIGS. 22A and 22B one week after the mice were injected with the vesicle embodiments and wherein there was a reduction in fluorescent signal in the liver, indicating clearance of the vesicles; however, the signals were relatively sustained in the tumors and there was little to no fluorescence in the heart or lungs, establishing that the vesicles exhibit organ-specific accumulation in tumors, but do not accumulate in the heart or lung and thus do not contribute to toxicity in these organs.

In this example, two A549 tumor bearing mice were evaluated after being injected with a formulation comprising vesicles comprising DC$_{8,9}$PC and DSPE-PEG2000 at a 90:10 mole ratio (DC$_{8,9}$PC:DSPE-PEG2000). In particular, 0.1 ml of the vesicle formulation containing 1 mg lipid content & trace amounts of DiR was injected in each mouse. Results are shown in FIGS. 22A, 22B, and 23. As can be seen in FIGS. 22A and 22B, a high intensity signal was observed to be localized in the tumor of each mouse. Also, a rapid decrease of the liver signal was observed therefore establishing that the vesicles should not exhibit liver toxicity. FIG. 23 also establishes that organ-specific accumulation can be achieved with the vesicles after one week post injection.

Example 14

Figure 25A:
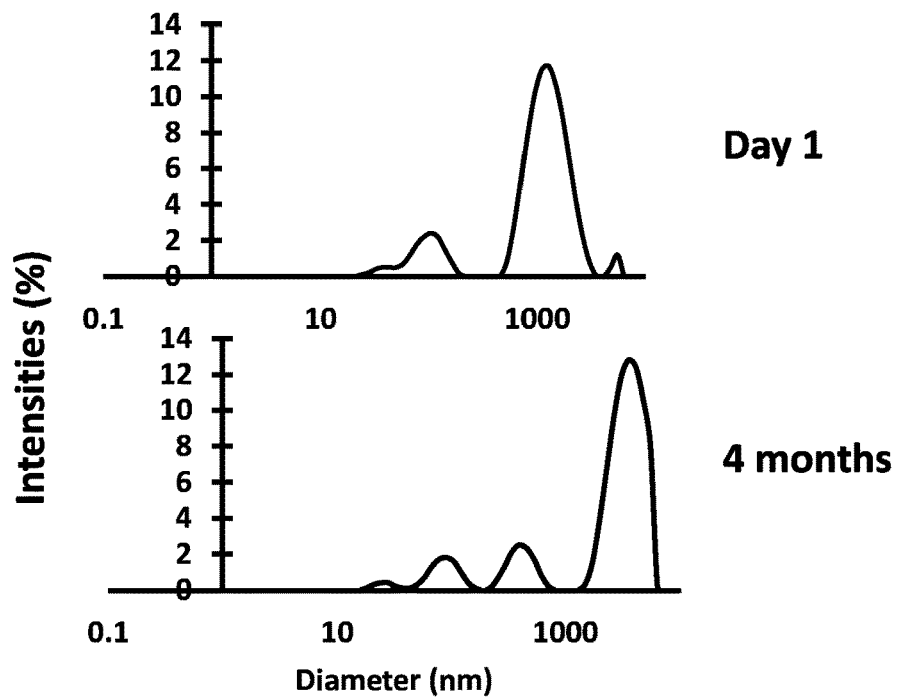
FIGS. 25A and 25B are graphs of intensity (%) as a function of diameter (nm), showing the average diameter and polydispersity index of certain formulations comprising DSPE-PEG350 and $DC_{8,9}PC$ (FIG. 25A) and DSPE-PEG1000 and $DC_{8,9}PC$ (FIG. 25B) after 1 day (top graphs of FIGS. 25A and 25B) and after 4 months (bottom graphs of FIGS. 25A and 25B).
Figure 25B:
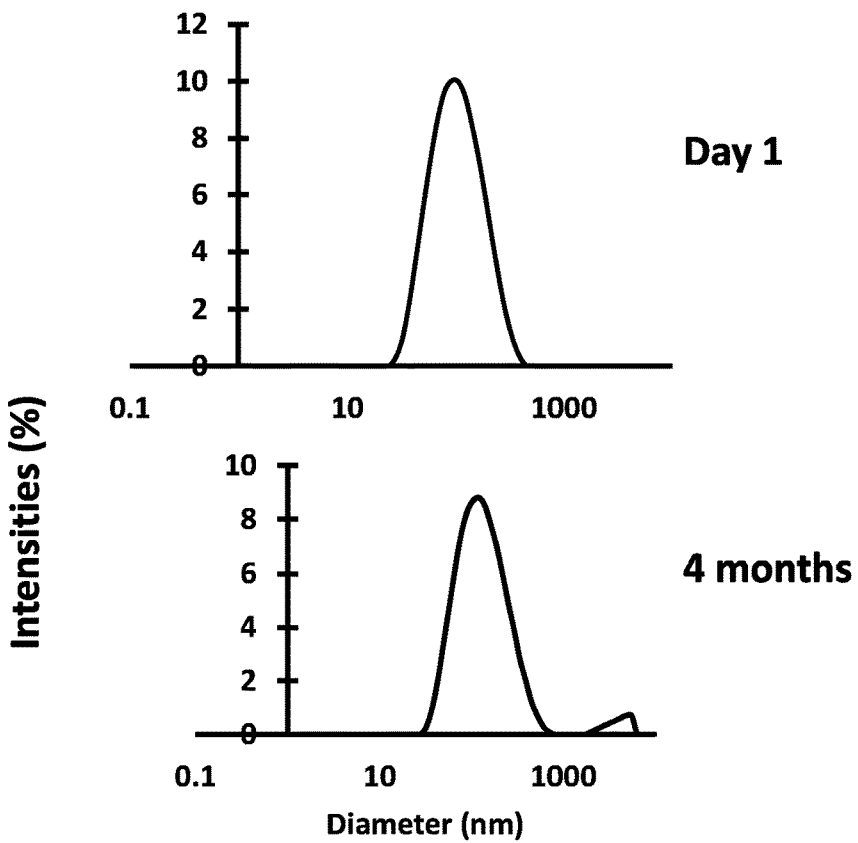

In this example, the effect of PEG chain length variations on vesicle formation was evaluated. A vesicle embodiment comprising DSPE-PEG350 was compared to a vesicle embodiment comprising DSPE-PEG1000. Details regarding the specific formulations are provided in Table 5. As can be seen by comparing the hydrodynamic size and stability results shown in FIGS. 25A and 25B, the vesicles comprising lipids with shorter PEG chains (e.g., DSPE-PEG350) (see FIG. 25A) exhibited lower stability after 4 months than vesicles comprising lipids with longer PEG chains (e.g., DSPE-PEG1000) (see FIG. 25B).

Example 15

Figure 26A:
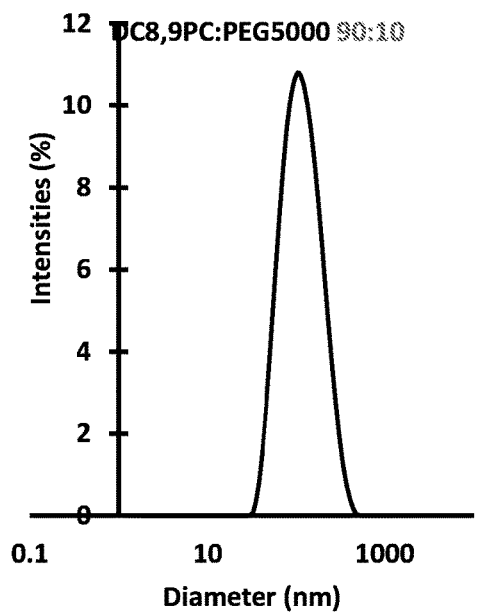
FIGS. 26A-26D are graphs of intensity (%) as a function of diameter (nm), showing the average diameter and polydispersity index of certain formulations comprising DSPE-PEG5000 and $DC_{8,9}PC$ at different ratios and for different time periods.
Figure 26B:
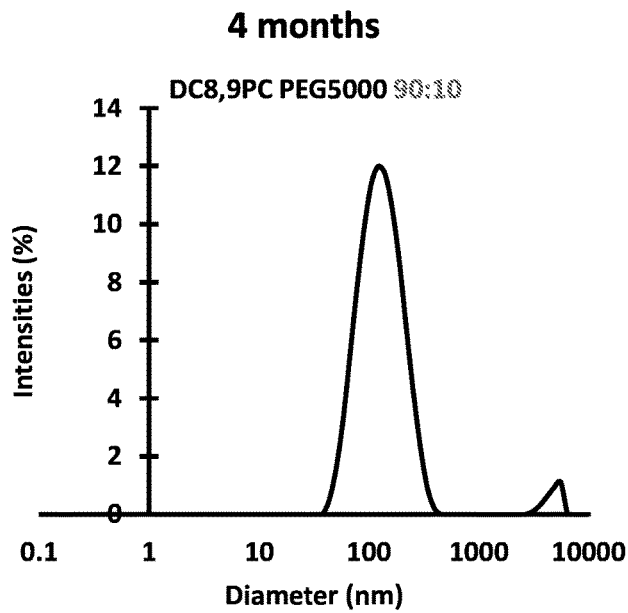
Figure 26C:
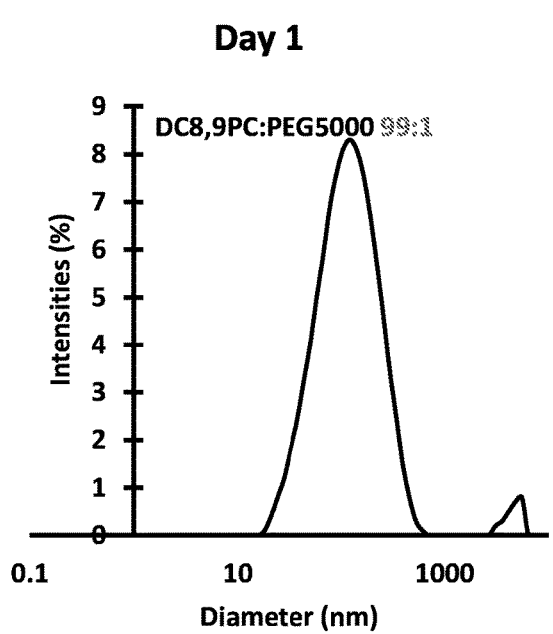
Figure 26D:
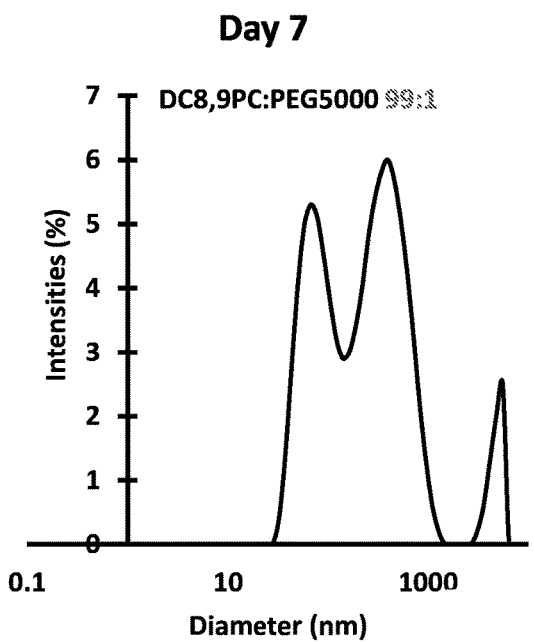

In this example, the hydrodynamic size, stability, and HPPH-loading efficiency of vesicle embodiments comprising a DC$_{8,9}$PC:DSPE-PEG5000 binary lipid bilayer were evaluated. Details regarding the specific formulations are provided in Table 4. As can be seen by comparing FIGS. 26A and 26B with FIGS. 26C and 26D, vesicles comprising the DC$_{8,9}$PC:DSPE-PEG5000 binary lipid bilayer exhibited good stability over an extended period of time, particularly for embodiments comprising a 90:10 ratio of DC$_{8,9}$PC:DSPE-PEG5000.

Example 16

Figure 27A:
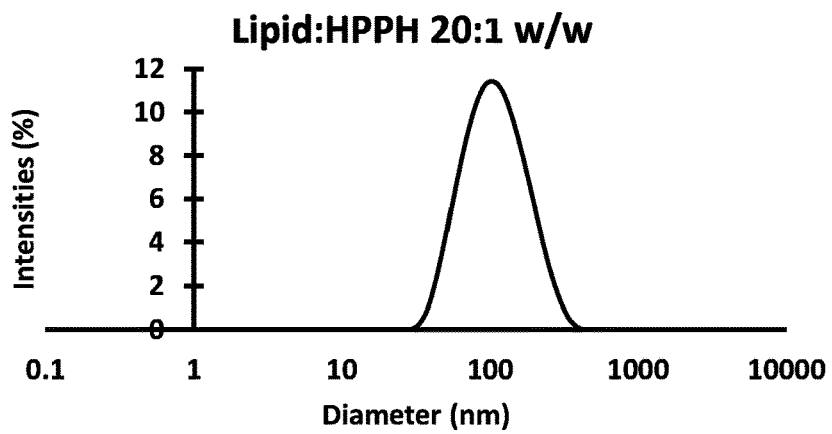
FIGS. 27A-27C provide results obtained from analyzing vesicle embodiments comprising (i) DSPE-PEG2000, $DC_{8,9}PC$, and $DC_{8,9}PE$ (FIGS. 27A and 27B) and (ii) DSPE-PEG2000 and $DC_{8,9}PE$ (FIG. 27C) and further including HPPH.
Figure 27B:
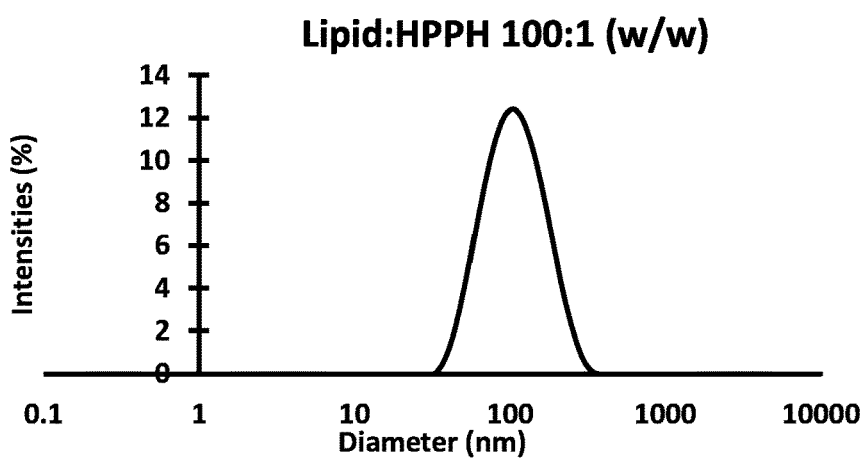
Figure 27C:
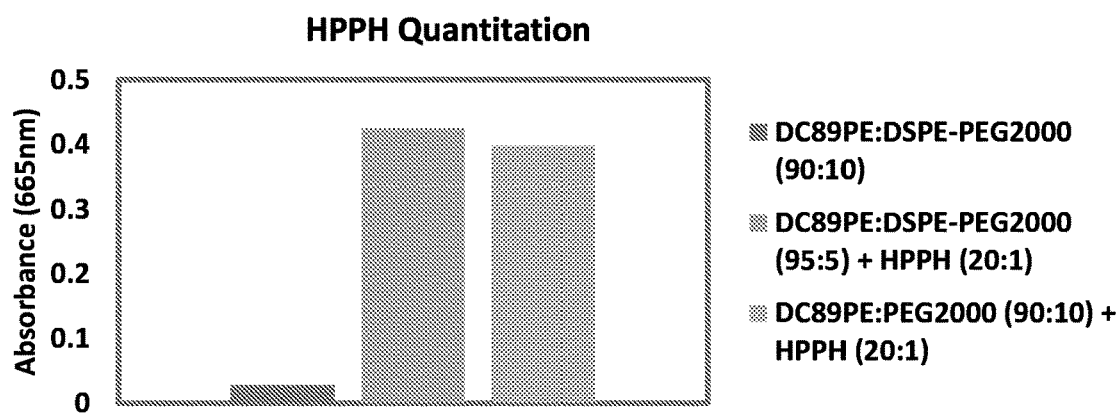

In this example, the effect of including an alkyne-containing phosphoethanolamine lipid in a vesicle (along with the alkyne-containing phospholipid and the PEGylated lipid) was evaluated. Details about the specific formulations are provided in Table 3. As can be seen in FIGS. 27A-27C, vesicle embodiments comprising the alkyne-containing phosphoethanolamine lipid exhibited good stability at different ratios of total lipid content to HPPH content.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A vesicle, comprising:
   a binary lipid bilayer comprising an alkyne-containing phospholipid and a PEGylated lipid; and
   a cytotoxic agent embedded in the binary lipid bilayer;
   wherein the binary lipid bilayer is free of, or does not comprise, a lipid other than the alkyne-containing phospholipid or the PEGylated lipid.

2. The vesicle of claim 1, wherein the binary lipid bilayer comprises greater than 6 mol % to 20 mol % of the PEGylated lipid.

3. The vesicle of claim 1, wherein the binary lipid bilayer comprises 10 mol % to 20 mol % of the PEGylated lipid.

4. The vesicle of claim 1, wherein the alkyne-containing phospholipid and the PEGylated lipid, taken together, and the cytotoxic agent are present at a ratio of 1:0.05, total lipid:cytotoxic agent.

5. The vesicle of claim 1, wherein the alkyne-containing phospholipid is an alkyne-containing phosphocholine lipid or a mixture of the alkyne-containing phosphocholine lipid and an alkyne-containing phosphoethanolamine lipid.

6. The vesicle of claim 5, wherein the alkyne-containing phosphocholine lipid is 1,2-bis(tricosa-10,12-diynoyl)-sn-glycero-3-phosphocholine (DC$_{8,9}$PC) and wherein the alkyne-containing phosphoethanolamine lipid is 1,2-bis(10,12-tricosadiynoyl)-sn-glycero-3-phosphoethanolamine (DC$_{8,9}$PE).

7. The vesicle of claim 1, wherein the PEGylated lipid is a PEGylated 1,2-distearoyl-sn-glycero-3-phosphoethanolamine (DSPE) lipid comprising a PEG group having a molecular weight ranging from 500 Da to 5000 Da.

8. The vesicle of claim 1, wherein the PEGylated lipid is a PEGylated DSPE lipid comprising a PEG group having a molecular weight ranging from 1000 Da to 3000 Da.

9. The vesicle of claim 1, wherein the PEGylated lipid is 1,2-distearoyl-sn-glycero-3-phosphoethanolamine-N-methoxy (polyethylene glycol)-2000 (DSPE-PEG2000).

10. The vesicle of claim 1, wherein the cytotoxic agent is a tetrapyrrollic compound, a camptothecin compound, paclitaxel, daunorubicin, methotrexate, vincristine, etoposide, sorafenib, erlotinib, imatinib, or any combination thereof.

11. The vesicle of claim 10, wherein the tetrapyrrollic compound is 2-[1-hexyloxyethyl]-2-devinyl pyropheophorbide-a (HPPH), (17S,18S)-18-(2-carboxyethyl)-20-(carboxymethyl)-12-ethenyl-7-ethyl-3,8,13,17-tetramethyl-17,18,22,23-tetrahydroporphyrin-2-carboxylic acid (Ce6), (3S,4S)-9-Ethenyl-14-ethyl-21-(methoxycarbonyl)-4,8,13,18-tetramethyl-20-oxo-3-phorbinepropanoic acid; 3,3',3",3"'-(2,3-dihydroporphyrin-5,10,15,20-tetrayl)tetraphenol, 3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24] octacosa-1,3,5,7,9,11 (27),12,14,16,18 (25), 19,21-dodecaen-9-yl]propanoic acid, or any combination thereof.

12. The vesicle of claim 10, wherein the camptothecin compound is camptothecin, silatecan 7-t-butyldimethylsilyl-10-hydroxycamptothecin, 7-ethyl-10-hydroxy-20(S)-camptothecin, topotecan, irinotecan, 9-nitro-camptothecin, lurtotecan, exatecan, gimatecan, or karenitecin.

13. The vesicle of claim 1, comprising a binary lipid bilayer consisting of an alkyne-containing lipid, a PEGylated lipid and a cytotoxic agent embedded within the binary lipid bilayer.

14. A vesicle, comprising:
a binary lipid bilayer comprising (i) DSPE-PEG2000 and (ii) $DC_{8,9}PC$, or a combination of $DC_{8,9}PC$ and $DC_{8,9}PE$; and
HPPH, Ce6, and/or camptothecin embedded in the binary lipid bilayer; and wherein the binary lipid bilayer is free of, or does not comprise, a lipid other than the $DC_{8,9}PC$, the $DC_{8,9}PE$, and the DSPE-PEG2000.

15. A method, comprising:
providing a vesicle according to claim 1; and
irradiating the vesicle with targeted application of light having a selected wavelength in the near-infrared range and a selected intensity for an effective period of time to activate at least a portion of the cytotoxic agent.

16. The method of claim 15, wherein irradiating the vesicle with targeted application of light comprises irradiating the vesicle with a laser that produces light having a wavelength of 650-670 nm.

17. The method of claim 15, wherein the selected intensity is from 1 mW to 500 mW and/or the effective period of time is at least 30 seconds.

18. The method of claim 15, further comprising:
identifying a subject as having a condition that may be treated with the cytotoxic agent;
administering the vesicle to the subject; and
wherein the targeted application of light is directed at a targeted portion of the subject.

19. The method of claim 18, wherein the subject has a tumor and the targeted portion of the subject includes an area proximate a location of the tumor and wherein administering the vesicle to the subject comprises intravenously injecting an amount of the vesicle effective to induce tumor size regression.

20. The method of claim 18, wherein irradiating is performed 4-6 hours after administering the vesicle to the subject.

21. The method of claim 18, wherein administering the vesicle to the subject comprises administering a pharmaceutical composition comprising the vesicle to the subject.

22. The method of claim 18, wherein the targeted application of light occurs by (i) externally applying the light to the targeted portion of the subject for the effective period of time, thereby transcutaneously applying the light to the tumor or (ii) internally applying the light to the targeted portion of the subject for the effective period of time using an endoscope or a fiber optic catheter.

23. A method for impairing growth of a tumor in a subject, comprising:
administering to the subject a therapeutically effective amount of a vesicle according to claim 1; and
irradiating the vesicle by targeted application of light having a selected wavelength in the near-infrared range and a selected intensity to a target area of the subject proximate a location of the tumor for an effective period of time to activate at least a portion of the cytotoxic agent to promote reactive oxygen species formation, thereby impairing growth of the tumor.

24. The method of claim 23, wherein the effective period of time is at least 30 seconds and irradiating is performed 4-6 hours after administering the vesicle to the subject.

25. The method of claim 23, wherein administering the vesicle to the subject comprises administering an amount of the vesicle effective to induce tumor size regression and/or wherein the vesicle is administered via intravenous injection.

26. The method of claim 23, wherein administering the vesicle to the subject comprises administering a pharmaceutical composition comprising the vesicle to the subject.

27. The method of claim 23, wherein irradiating the vesicle by targeted application of light comprises externally or internally applying the light to the targeted portion of the subject for the effective period of time using an endoscope or a fiber optic catheter.

* * * * *